US009370629B2

(12) United States Patent
Damani et al.

(10) Patent No.: US 9,370,629 B2
(45) Date of Patent: Jun. 21, 2016

(54) SELF-CONTAINED HEATING UNIT AND DRUG-SUPPLY UNIT EMPLOYING SAME

(71) Applicant: Alexza Pharmaceuticals, Inc., Mountain View, CA (US)

(72) Inventors: Ramesh Damani, Sunnyvale, CA (US); Ron L. Hale, Sandia Park, NM (US); Daniel J. Myers, Mountain View, CA (US); Reynaldo J. Quintana, Redwood City, CA (US); Dennis W. Solas, San Francisco, CA (US); Soonho Song, Seoul (KR); Pravin Soni, Sunnyvale, CA (US); Curtis Tom, San Mateo, CA (US); Krishnamohan Sharma, Milpitas, CA (US)

(73) Assignee: ALEXZA PHARMACEUTICALS, INC., Mountain View, CA (US)

( * ) Notice: Subject to any disclaimer, the term of this patent is extended or adjusted under 35 U.S.C. 154(b) by 0 days.

(21) Appl. No.: 14/675,275

(22) Filed: Mar. 31, 2015

(65) Prior Publication Data
US 2015/0265783 A1 Sep. 24, 2015

Related U.S. Application Data

(63) Continuation of application No. 13/783,508, filed on Mar. 4, 2013, now Pat. No. 8,991,387, which is a continuation of application No. 12/485,704, filed on Jun. 16, 2009, now Pat. No. 8,387,612, which is a
(Continued)

(51) Int. Cl.
*A61M 11/00* (2006.01)
*A61M 11/04* (2006.01)
(Continued)

(52) U.S. Cl.
CPC .............. *A61M 11/00* (2013.01); *A61M 11/041* (2013.01); *A61M 11/042* (2014.02);
(Continued)

(58) Field of Classification Search
CPC ......................................................... F24J 1/00
USPC .................................. 126/263.1; 128/203.26
See application file for complete search history.

(56) References Cited

U.S. PATENT DOCUMENTS

| 802,256 A | 10/1905 | Bamberger et al. |
| 1,239,634 A | 9/1917 | Stuart |

(Continued)

FOREIGN PATENT DOCUMENTS

| CA | 2152684 | 1/1996 |
| CH | 436 297 | 5/1967 |

(Continued)

OTHER PUBLICATIONS

Office Action mailed Jan. 26, 2007 with respect to U.S. Appl. No. 10/057,198.
(Continued)

*Primary Examiner* — Avinash Savani
(74) *Attorney, Agent, or Firm* — Swanson & Bratschun, L.L.C.

(57) ABSTRACT

Heating units, drug supply units and drug delivery articles capable of rapid heating are disclosed. Heating units comprising a substrate and a solid fuel capable of undergoing an exothermic metal oxidation reaction disposed within the substrate are disclosed. These heating units can be actuated by electrical resistance, by optical ignition or by percussion. Drug supply units and drug delivery articles wherein a solid fuel is configured to heat a substrate to a temperature sufficient to rapidly thermally vaporize a drug disposed thereon are also disclosed.

13 Claims, 23 Drawing Sheets

Related U.S. Application Data continuation-in-part of application No. 10/850,895, filed on May 20, 2004, now abandoned, and a continuation-in-part of application No. 10/851,429, filed on May 20, 2004, now abandoned, and a continuation-in-part of application No. 10/851,883, filed on May 20, 2004, now abandoned, and a continuation-in-part of application No. 10/851,432, filed on May 20, 2004, now abandoned.

(60) Provisional application No. 60/472,697, filed on May 21, 2003.

(51) Int. Cl.
  A61M 15/06 (2006.01)
  B01B 1/00 (2006.01)
  C06B 33/00 (2006.01)
  C06B 45/14 (2006.01)
  C09K 5/18 (2006.01)
  F24J 1/00 (2006.01)
  A61M 16/00 (2006.01)

(52) U.S. Cl.
  CPC ............ *A61M 11/047* (2014.02); *A61M 15/06* (2013.01); *B01B 1/005* (2013.01); *C06B 33/00* (2013.01); *C06B 45/14* (2013.01); *C09K 5/18* (2013.01); *F24J 1/00* (2013.01); *A61M 11/048* (2014.02); *A61M 2016/0021* (2013.01); *A61M 2016/0027* (2013.01); *A61M 2202/064* (2013.01); *A61M 2205/36* (2013.01); *A61M 2205/364* (2013.01); *A61M 2205/3653* (2013.01); *A61M 2205/8268* (2013.01); *F23B 2900/00003* (2013.01); *F23C 2900/99008* (2013.01); *Y02E 20/346* (2013.01)

(56) References Cited

U.S. PATENT DOCUMENTS

| | | |
|---|---|---|
| 1,535,486 A | 4/1925 | Lundy |
| 1,803,334 A | 5/1931 | Lehmann |
| 1,864,980 A | 6/1932 | Curran |
| 2,024,225 A | 12/1935 | Igari |
| 2,084,299 A | 6/1937 | Borden |
| 2,086,140 A | 7/1937 | Ernst |
| 2,230,753 A | 2/1941 | Klavehn et al. |
| 2,230,754 A | 2/1941 | Klavehn et al. |
| 2,243,669 A | 5/1941 | Clyne |
| 2,280,598 A | 4/1942 | Meridith |
| 2,309,846 A | 2/1943 | Marius Holm Einar |
| 2,469,656 A | 5/1949 | Lienert |
| 2,500,790 A | 3/1950 | Bennett |
| 2,531,548 A | 11/1950 | Bennett |
| 2,598,823 A | 6/1952 | O'Grady et al. |
| 2,624,332 A | 1/1953 | Lang |
| 2,714,649 A | 8/1955 | Critzer |
| 2,741,812 A | 4/1956 | Andre |
| 2,761,055 A | 8/1956 | Ike |
| 2,887,106 A | 5/1959 | Robinson |
| 2,898,649 A | 8/1959 | Murray |
| 2,902,484 A | 9/1959 | Horclois |
| 2,906,094 A | 9/1959 | Damon et al. |
| 2,953,443 A | 9/1960 | Lloyd |
| 2,999,460 A | 9/1961 | Stinger et al. |
| 3,043,977 A | 7/1962 | Morowitz |
| 3,080,624 A | 3/1963 | Webber, III |
| 3,118,798 A | 1/1964 | Winkler |
| 3,150,020 A | 9/1964 | Kilmer |
| 3,160,097 A | 12/1964 | Colburn, Jr. et al. |
| 3,164,600 A | 1/1965 | Janssen et al. |
| 3,169,095 A | 2/1965 | Thiel et al. |
| 3,200,819 A | 8/1965 | Gilbert |
| 3,219,533 A | 11/1965 | Mullins |
| 3,238,076 A | 3/1966 | Taylor et al. |
| 3,282,729 A | 11/1966 | Richardson et al. |
| 3,296,249 A | 1/1967 | Bell |
| 3,299,185 A | 1/1967 | Oda et al. |
| 3,311,459 A | 3/1967 | Francis et al. |
| 3,363,559 A | 1/1968 | Estes |
| 3,371,085 A | 2/1968 | Reeder et al. |
| 3,393,197 A | 7/1968 | Pachter |
| 3,433,791 A | 3/1969 | Bentley et al. |
| 3,503,814 A | 3/1970 | Helms, Jr. et al. |
| 3,535,063 A | 10/1970 | Anderson et al. |
| 3,560,607 A | 2/1971 | Hartley et al. |
| 3,575,714 A | 4/1971 | Bennett et al. |
| 3,580,250 A | 5/1971 | Oroza |
| 3,695,179 A | 10/1972 | Rainone et al. |
| 3,701,782 A | 10/1972 | Hester |
| 3,703,144 A | 11/1972 | Colburn, Jr. |
| 3,724,990 A | 4/1973 | Schupp |
| 3,724,991 A | 4/1973 | Schupp |
| 3,730,669 A | 5/1973 | Shaffer |
| 3,749,547 A | 7/1973 | Gregory et al. |
| 3,763,347 A | 10/1973 | Whitaker et al. |
| 3,791,302 A | 2/1974 | McLeod |
| 3,792,302 A | 2/1974 | Downing et al. |
| 3,828,676 A | 8/1974 | Junker |
| 3,830,671 A | 8/1974 | McArdle |
| 3,831,606 A | 8/1974 | Damani |
| 3,847,650 A | 11/1974 | Gregory et al. |
| 3,864,326 A | 2/1975 | Babington |
| 3,893,798 A | 7/1975 | Sterling |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd et al. |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,000,022 A | 12/1976 | Beckert et al. |
| 4,008,723 A | 2/1977 | Borthwick et al. |
| 4,013,061 A | 3/1977 | Trumble et al. |
| 4,020,379 A | 4/1977 | Manning |
| 4,025,285 A | 5/1977 | Brown |
| 4,045,156 A | 8/1977 | Chu et al. |
| 4,047,483 A | 9/1977 | Williams |
| 4,053,337 A | 10/1977 | Collins |
| 4,059,388 A | 11/1977 | Shaffer |
| 4,078,881 A | 3/1978 | Anderson et al. |
| 4,079,742 A | 3/1978 | Rainer et al. |
| 4,096,549 A | 6/1978 | Anderson et al. |
| 4,104,210 A | 8/1978 | Coran et al. |
| 4,121,583 A | 10/1978 | Chen |
| 4,130,082 A | 12/1978 | Bouchard et al. |
| 4,141,369 A | 2/1979 | Burruss |
| 4,158,084 A | 6/1979 | Prentice |
| 4,160,765 A | 7/1979 | Weinstock |
| 4,166,087 A | 8/1979 | Cline et al. |
| 4,183,912 A | 1/1980 | Rosenthale |
| 4,184,099 A | 1/1980 | Lindauer et al. |
| 4,190,654 A | 2/1980 | Gherardi et al. |
| 4,193,388 A | 3/1980 | Yang |
| 4,198,200 A | 4/1980 | Fonda et al. |
| RE30,285 E | 5/1980 | Babington |
| 4,205,673 A | 6/1980 | Wise |
| 4,219,031 A | 8/1980 | Rainer et al. |
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,329,924 A | 5/1982 | Lagofun |
| 4,340,072 A | 7/1982 | Bolt et al. |
| 4,346,059 A | 8/1982 | Spector |
| 4,347,855 A | 9/1982 | Lanzillotti et al. |

(56) References Cited

U.S. PATENT DOCUMENTS

| | | |
|---|---|---|
| 4,354,432 A | 10/1982 | Cannavo et al. |
| 4,372,210 A | 2/1983 | Shaffer et al. |
| 4,372,213 A | 2/1983 | Rozner et al. |
| 4,374,686 A | 2/1983 | Davitt et al. |
| 4,376,767 A | 3/1983 | Sloan |
| 4,391,285 A | 7/1983 | Burnett et al. |
| 4,419,153 A | 12/1983 | Boberg |
| 4,423,071 A | 12/1983 | Chignac et al. |
| 4,474,191 A | 10/1984 | Steiner |
| 4,484,576 A | 11/1984 | Albarda |
| 4,484,960 A | 11/1984 | Rucker |
| 4,508,726 A | 4/1985 | Coleman |
| 4,523,589 A | 6/1985 | Krauser |
| 4,526,758 A | 7/1985 | Alengoz et al. |
| 4,556,539 A | 12/1985 | Spector |
| 4,566,451 A | 1/1986 | Badewien |
| 4,588,425 A | 5/1986 | Usry et al. |
| 4,588,721 A | 5/1986 | Mahan |
| 4,591,615 A | 5/1986 | Aldred et al. |
| 4,605,552 A | 8/1986 | Fritschi |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III et al. |
| 4,671,270 A | 6/1987 | Kato |
| 4,683,231 A | 7/1987 | Glassman |
| 4,693,868 A | 9/1987 | Katsuda et al. |
| 4,700,629 A | 10/1987 | Benson et al. |
| 4,708,151 A | 11/1987 | Shelar |
| 4,714,082 A | 12/1987 | Banerjee et al. |
| 4,721,224 A | 1/1988 | Kawabata |
| 4,722,334 A | 2/1988 | Blackmer et al. |
| 4,734,560 A | 3/1988 | Bowen |
| 4,735,217 A | 4/1988 | Gerth et al. |
| 4,735,358 A | 4/1988 | Morita et al. |
| 4,753,758 A | 6/1988 | Miller |
| 4,755,508 A | 7/1988 | Bock et al. |
| 4,756,318 A | 7/1988 | Clearman et al. |
| 4,757,764 A | 7/1988 | Thureson et al. |
| 4,765,347 A | 8/1988 | Sensabaugh, Jr. et al. |
| 4,771,795 A | 9/1988 | White et al. |
| 4,774,971 A | 10/1988 | Vieten |
| 4,793,365 A | 12/1988 | Sensabaugh, Jr. et al. |
| 4,793,366 A | 12/1988 | Hill |
| 4,800,903 A | 1/1989 | Ray et al. |
| 4,801,411 A | 1/1989 | Wellinghoff et al. |
| 4,814,161 A | 3/1989 | Jinks et al. |
| 4,819,665 A | 4/1989 | Roberts et al. |
| 4,848,374 A | 7/1989 | Chard et al. |
| 4,852,561 A | 8/1989 | Sperry |
| 4,853,052 A | 8/1989 | Calsson et al. |
| 4,853,517 A | 8/1989 | Bowen et al. |
| 4,854,331 A | 8/1989 | Banerjee et al. |
| 4,858,630 A | 8/1989 | Banerjee et al. |
| 4,863,720 A | 9/1989 | Burghart et al. |
| 4,881,541 A | 11/1989 | Eger et al. |
| 4,881,556 A | 11/1989 | Clearman et al. |
| 4,889,850 A | 12/1989 | Thornfeldt et al. |
| 4,892,037 A | 1/1990 | Betts |
| 4,892,109 A | 1/1990 | Strubel |
| 4,895,719 A | 1/1990 | Radhakrishnan et al. |
| 4,906,417 A | 3/1990 | Gentry |
| 4,911,157 A | 3/1990 | Miller |
| 4,917,119 A | 4/1990 | Potter et al. |
| 4,917,120 A | 4/1990 | Hill |
| 4,917,830 A | 4/1990 | Ortiz et al. |
| 4,922,901 A | 5/1990 | Brooks et al. |
| 4,924,883 A | 5/1990 | Perfetti et al. |
| 4,928,714 A | 5/1990 | Shannon |
| 4,941,483 A | 7/1990 | Ridings et al. |
| 4,947,874 A | 8/1990 | Brooks et al. |
| 4,947,875 A | 8/1990 | Brooks et al. |
| 4,963,289 A | 10/1990 | Ortiz et al. |
| 4,984,158 A | 1/1991 | Hillsman |
| 4,989,619 A | 2/1991 | Clearman et al. |
| 5,016,425 A | 5/1991 | Weick |
| 5,017,575 A | 5/1991 | Golwyn |
| 5,019,122 A | 5/1991 | Clearman et al. |
| 5,020,548 A | 6/1991 | Farrier et al. |
| 5,027,707 A | 7/1991 | Mei |
| 5,027,836 A | 7/1991 | Shannon et al. |
| 5,033,483 A | 7/1991 | Clearman et al. |
| 5,042,509 A | 8/1991 | Banerjee et al. |
| 5,049,389 A | 9/1991 | Radhakrishnun |
| 5,060,666 A | 10/1991 | Clearman et al. |
| 5,060,667 A | 10/1991 | Strubel |
| 5,060,671 A | 10/1991 | Counts et al. |
| 5,067,499 A | 11/1991 | Banerjee et al. |
| 5,072,726 A | 12/1991 | Mazloomdoost et al. |
| 5,076,292 A | 12/1991 | Sensabaugh, Jr. et al. |
| 5,099,861 A | 3/1992 | Clearman et al. |
| 5,109,180 A | 4/1992 | Boultinghouse et al. |
| 5,112,598 A | 5/1992 | Biesalski |
| 5,118,494 A | 6/1992 | Schultz et al. |
| 5,119,834 A | 6/1992 | Shannon et al. |
| 5,126,123 A | 6/1992 | Johnson |
| 5,133,368 A | 7/1992 | Neumann et al. |
| 5,135,009 A | 8/1992 | Muller et al. |
| 5,137,034 A | 8/1992 | Perfetti et al. |
| 5,144,962 A | 9/1992 | Counts et al. |
| 5,146,915 A | 9/1992 | Montgomery |
| 5,156,170 A | 10/1992 | Clearman et al. |
| 5,160,664 A | 11/1992 | Liu |
| 5,164,740 A | 11/1992 | Ivri |
| 5,166,202 A | 11/1992 | Schweizer |
| 5,167,242 A | 12/1992 | Turner et al. |
| 5,177,071 A | 1/1993 | Freidinger et al. |
| 5,186,164 A | 2/1993 | Raghuprasad |
| 5,192,548 A | 3/1993 | Velasquez et al. |
| 5,224,498 A | 7/1993 | Deevi et al. |
| 5,229,120 A | 7/1993 | DeVincent |
| 5,229,382 A | 7/1993 | Chakrabarti et al. |
| 5,240,922 A | 8/1993 | O'Neill |
| 5,249,586 A | 10/1993 | Morgan et al. |
| 5,255,674 A | 10/1993 | Oftedal et al. |
| 5,261,424 A | 11/1993 | Sprin et al. |
| 5,264,433 A | 11/1993 | Sato et al. |
| 5,284,133 A | 2/1994 | Burns et al. |
| 5,285,798 A | 2/1994 | Banerjee et al. |
| 5,292,499 A | 3/1994 | Evans et al. |
| 5,322,018 A | 6/1994 | Hadden et al. |
| 5,322,075 A | 6/1994 | Deevi et al. |
| 5,333,106 A | 7/1994 | Lanpher et al. |
| 5,345,951 A | 9/1994 | Serrano et al. |
| 5,357,984 A | 10/1994 | Farrier et al. |
| 5,363,842 A | 11/1994 | Mishelevich et al. |
| 5,364,838 A | 11/1994 | Rubsamen |
| 5,366,770 A | 11/1994 | Wang |
| 5,372,148 A | 12/1994 | McCafferty et al. |
| 5,376,386 A | 12/1994 | Ganderton et al. |
| 5,388,574 A | 2/1995 | Ingebrethsen |
| 5,391,081 A | 2/1995 | Lampotang et al. |
| 5,399,574 A | 3/1995 | Robertson et al. |
| 5,400,808 A | 3/1995 | Turner et al. |
| 5,431,167 A | 7/1995 | Savord |
| 5,436,230 A | 7/1995 | Soudant et al. |
| 5,445,606 A | 8/1995 | Haak et al. |
| 5,451,408 A | 9/1995 | Mezei et al. |
| 5,454,363 A | 10/1995 | Sata |
| 5,456,247 A | 10/1995 | Shilling et al. |
| 5,456,677 A | 10/1995 | Spector |
| 5,457,100 A | 10/1995 | Daniel |
| 5,457,101 A | 10/1995 | Greenwood et al. |
| 5,459,137 A | 10/1995 | Andrasi et al. |
| 5,462,740 A | 10/1995 | Evenstad et al. |
| 5,468,936 A | 11/1995 | Deevi et al. |
| 5,479,919 A | 1/1996 | Buchtal |
| 5,501,236 A | 3/1996 | Hill et al. |
| 5,507,277 A | 4/1996 | Rubsamen et al. |
| 5,509,354 A | 4/1996 | Dorffler et al. |
| 5,511,726 A | 4/1996 | Greenspan et al. |
| 5,519,019 A | 5/1996 | Andrasi et al. |
| 5,522,385 A | 6/1996 | Lloyd et al. |
| 5,525,329 A | 6/1996 | Snyder et al. |

(56) References Cited

U.S. PATENT DOCUMENTS

| | | |
|---|---|---|
| 5,538,020 A | 7/1996 | Farrier et al. |
| 5,543,434 A | 8/1996 | Weg |
| 5,544,646 A | 8/1996 | Lloyd et al. |
| 5,549,849 A | 8/1996 | Namura et al. |
| 5,564,442 A | 10/1996 | MacDonald et al. |
| 5,573,565 A | 11/1996 | Dalton et al. |
| 5,584,701 A | 12/1996 | Lampotang et al. |
| 5,586,550 A | 12/1996 | Ivri et al. |
| 5,591,368 A | 1/1997 | Fleischhauer et al. |
| 5,592,934 A | 1/1997 | Thwaites |
| 5,593,792 A | 1/1997 | Farrier et al. |
| 5,605,146 A | 2/1997 | Sarela |
| 5,605,897 A | 2/1997 | Beasley, Jr. et al. |
| 5,607,691 A | 3/1997 | Hale et al. |
| 5,619,984 A | 4/1997 | Hodson et al. |
| 5,622,944 A | 4/1997 | Hale et al. |
| 5,623,115 A | 4/1997 | Lauritzen et al. |
| 5,626,360 A | 5/1997 | Lauritzen et al. |
| 5,627,178 A | 5/1997 | Chakrabarti et al. |
| 5,641,938 A | 6/1997 | Holland et al. |
| 5,649,554 A | 7/1997 | Sprinkel |
| 5,654,520 A | 8/1997 | Boberg et al. |
| 5,655,523 A | 8/1997 | Hodson et al. |
| 5,656,255 A | 8/1997 | Jones |
| 5,660,166 A | 8/1997 | Lloyd et al. |
| 5,660,413 A | 8/1997 | Bergerson et al. |
| 5,666,977 A | 9/1997 | Higgins et al. |
| 5,672,843 A | 9/1997 | Evans et al. |
| 5,686,691 A | 11/1997 | Hamilton et al. |
| 5,690,809 A | 11/1997 | Subramaniam et al. |
| 5,694,919 A | 12/1997 | Rubsamen et al. |
| 5,697,896 A | 12/1997 | McNichols et al. |
| 5,718,222 A | 2/1998 | Lloyd et al. |
| 5,724,957 A | 3/1998 | Rubsamen et al. |
| 5,725,756 A | 3/1998 | Subramaniam et al. |
| 5,733,572 A | 3/1998 | Unger et al. |
| 5,735,263 A | 4/1998 | Rubsamen et al. |
| 5,738,865 A | 4/1998 | Baichwal et al. |
| 5,743,250 A | 4/1998 | Gonda et al. |
| 5,743,251 A | 4/1998 | Howell et al. |
| 5,744,469 A | 4/1998 | Tran |
| 5,747,001 A | 5/1998 | Wiedmann et al. |
| 5,756,449 A | 5/1998 | Andersen et al. |
| 5,758,637 A | 6/1998 | Ivri et al. |
| 5,763,813 A | 6/1998 | Cohen et al. |
| 5,767,117 A | 6/1998 | Moskowitz et al. |
| 5,769,621 A | 6/1998 | Early et al. |
| 5,770,222 A | 6/1998 | Unger et al. |
| 5,771,882 A | 6/1998 | Psaros et al. |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. et al. |
| 5,819,756 A | 10/1998 | Mielordt |
| 5,823,178 A | 10/1998 | Lloyd et al. |
| 5,829,436 A | 11/1998 | Rubsamen et al. |
| 5,833,891 A | 11/1998 | Subramaniam et al. |
| 5,840,246 A | 11/1998 | Hammons et al. |
| 5,845,933 A | 12/1998 | Walker et al. |
| 5,855,564 A | 1/1999 | Ruskewicz |
| 5,855,913 A | 1/1999 | Hanes et al. |
| 5,874,064 A | 2/1999 | Edwards et al. |
| 5,874,481 A | 2/1999 | Weers et al. |
| 5,875,776 A | 3/1999 | Vaghefi |
| 5,878,752 A | 3/1999 | Adams et al. |
| 5,884,620 A | 3/1999 | Gonda et al. |
| 5,890,908 A | 4/1999 | Lampotang et al. |
| 5,894,841 A | 4/1999 | Voges |
| 5,900,249 A | 5/1999 | Smith |
| 5,906,811 A | 5/1999 | Hersh |
| 5,907,075 A | 5/1999 | Subramaniam et al. |
| 5,910,301 A | 6/1999 | Farr et al. |
| 5,915,378 A | 6/1999 | Lloyd et al. |
| 5,918,595 A | 7/1999 | Olsson |
| 5,928,520 A | 7/1999 | Haumesser |
| 5,929,093 A | 7/1999 | Pang et al. |
| 5,934,272 A | 8/1999 | Lloyd et al. |
| 5,934,289 A | 8/1999 | Watkins et al. |
| 5,935,604 A | 8/1999 | Illum |
| 5,938,117 A | 8/1999 | Ivri |
| 5,939,100 A | 8/1999 | Albrechtsen et al. |
| 5,941,240 A | 8/1999 | Gonda et al. |
| 5,944,012 A | 8/1999 | Pera |
| 5,957,124 A | 9/1999 | Lloyd et al. |
| 5,960,792 A | 10/1999 | Lloyd et al. |
| 5,970,973 A | 10/1999 | Gonda et al. |
| 5,971,951 A | 10/1999 | Ruskewicz |
| 5,985,309 A | 11/1999 | Edwards et al. |
| 5,993,805 A | 11/1999 | Sutton et al. |
| 6,004,970 A | 12/1999 | O'Malley et al. |
| 6,008,214 A | 12/1999 | Kwon et al. |
| 6,008,216 A | 12/1999 | Chakrabarti et al. |
| 6,013,050 A | 1/2000 | Bellhouse et al. |
| 6,014,969 A | 1/2000 | Lloyd et al. |
| 6,014,970 A | 1/2000 | Ivri et al. |
| 6,014,972 A | 1/2000 | Sladek |
| 6,041,777 A | 3/2000 | Faithfull et al. |
| 6,044,777 A | 4/2000 | Walsh |
| 6,048,550 A | 4/2000 | Chan et al. |
| 6,048,857 A | 4/2000 | Ellinwood, Jr. et al. |
| 6,050,260 A | 4/2000 | Daniell et al. |
| 6,051,257 A | 4/2000 | Kodas et al. |
| 6,051,566 A | 4/2000 | Bianco |
| 6,062,210 A | 5/2000 | Welles |
| RE36,744 E | 6/2000 | Goldberg |
| 6,080,248 A | 6/2000 | Finck et al. |
| 6,089,857 A | 7/2000 | Matsuura et al. |
| 6,090,212 A | 7/2000 | Mahawili |
| 6,095,134 A | 8/2000 | Sievers et al. |
| 6,095,153 A | 8/2000 | Kessler et al. |
| 6,098,619 A | 8/2000 | Britto et al. |
| 6,102,036 A | 8/2000 | Slutsky et al. |
| 6,113,795 A | 9/2000 | Subramaniam et al. |
| 6,117,866 A | 9/2000 | Bondinell et al. |
| 6,125,853 A | 10/2000 | Susa et al. |
| 6,126,919 A | 10/2000 | Stefely et al. |
| 6,131,566 A | 10/2000 | Ashurst et al. |
| 6,131,570 A | 10/2000 | Schuster et al. |
| 6,133,327 A | 10/2000 | Kimura et al. |
| 6,135,369 A | 10/2000 | Prendergast et al. |
| 6,155,268 A | 12/2000 | Takeuchi |
| 6,168,661 B1 | 1/2001 | Dinkelman |
| 6,211,171 B1 | 4/2001 | Sawynok et al. |
| 6,234,167 B1 | 5/2001 | Cox et al. |
| 6,241,969 B1 | 6/2001 | Saidi et al. |
| 6,250,301 B1 | 6/2001 | Pate |
| 6,255,334 B1 | 7/2001 | Sands |
| 6,263,872 B1 | 7/2001 | Schuster et al. |
| 6,264,922 B1 | 7/2001 | Wood et al. |
| 6,267,110 B1 | 7/2001 | Tenenboum et al. |
| 6,284,287 B1 | 9/2001 | Sarlikiotis et al. |
| 6,289,813 B1 | 9/2001 | Duguet et al. |
| 6,289,889 B1 | 9/2001 | Bell et al. |
| 6,290,986 B1 | 9/2001 | Murdock et al. |
| 6,299,900 B1 | 10/2001 | Reed et al. |
| 6,300,710 B1 | 10/2001 | Nakamori |
| 6,306,431 B1 | 10/2001 | Zhang et al. |
| 6,313,176 B1 | 11/2001 | Ellinwood, Jr. et al. |
| 6,324,979 B1 | 12/2001 | Troianello |
| 6,352,506 B1 | 3/2002 | Eppstein et al. |
| 6,376,550 B1 | 4/2002 | Raber et al. |
| 6,391,282 B1 | 5/2002 | Dugger, III |
| 6,408,854 B1 | 6/2002 | Gonda et al. |
| 6,413,930 B1 | 7/2002 | Ratti et al. |
| 6,420,351 B1 | 7/2002 | Tsai et al. |
| 6,431,166 B2 | 8/2002 | Gonda et al. |
| 6,443,152 B1 | 9/2002 | Lockhart et al. |
| 6,444,326 B1 | 9/2002 | Smith |
| 6,444,665 B1 | 9/2002 | Helton et al. |
| 6,461,591 B1 | 10/2002 | Keller et al. |
| 6,478,903 B1 | 11/2002 | John, Jr. et al. |
| 6,479,074 B2 | 11/2002 | Murdock et al. |
| 6,487,971 B1 | 12/2002 | Anderson |
| 6,491,233 B2 | 12/2002 | Nichols |

(56) References Cited

U.S. PATENT DOCUMENTS

| | | |
|---|---|---|
| 6,497,780 B1 | 12/2002 | Carlson |
| 6,506,454 B2 | 1/2003 | Ishigami |
| 6,506,762 B1 | 1/2003 | Horvath et al. |
| 6,514,482 B1 | 2/2003 | Bartus et al. |
| 6,516,796 B1 | 2/2003 | Cox et al. |
| 6,557,552 B1 | 5/2003 | Cox et al. |
| 6,568,390 B2 | 5/2003 | Nichols et al. |
| 6,591,839 B2 | 7/2003 | Meyer et al. |
| 6,632,047 B2 | 10/2003 | Vinegar et al. |
| 6,638,981 B2 | 10/2003 | Williams et al. |
| 6,682,716 B2 | 1/2004 | Hodges et al. |
| 6,701,922 B2 | 3/2004 | Hindle et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,772,757 B2 | 8/2004 | Sprinkel, Jr. et al. |
| 6,776,978 B2 | 8/2004 | Rabinowitz et al. |
| 6,779,520 B2 | 8/2004 | Genova et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,993,811 B2 | 2/2006 | Das et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,040,314 B2 | 5/2006 | Nguyen et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,131,599 B2 | 11/2006 | Katase |
| 7,169,378 B2 | 1/2007 | Rabinowitz et al. |
| 7,229,966 B2 | 6/2007 | Quay et al. |
| 7,402,777 B2 | 7/2008 | Ron et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,494,344 B2 | 2/2009 | Galauner et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 7,981,401 B2 | 7/2011 | Every et al. |
| 7,987,846 B2 | 8/2011 | Hale et al. |
| 7,988,952 B2 | 8/2011 | Rabinowitz et al. |
| 8,003,080 B2 | 8/2011 | Rabinowitz et al. |
| 8,074,644 B2 | 12/2011 | Hale et al. |
| 8,173,107 B2 | 5/2012 | Rabinowitz et al. |
| 8,235,037 B2 | 8/2012 | Hale et al. |
| 8,288,372 B2 | 10/2012 | Hale et al. |
| 8,333,197 B2 | 12/2012 | Cross et al. |
| 8,387,612 B2 | 3/2013 | Damani et al. |
| 8,506,935 B2 | 8/2013 | Hale et al. |
| 8,955,512 B2 | 2/2015 | Hale et al. |
| 8,991,387 B2 | 3/2015 | Damani et al. |
| 2001/0020147 A1 | 9/2001 | Staniforth et al. |
| 2001/0037104 A1 | 11/2001 | Zhang et al. |
| 2001/0039262 A1 | 11/2001 | Venkataraman |
| 2001/0042546 A1 | 11/2001 | Umeda et al. |
| 2002/0000225 A1 | 1/2002 | Schuler et al. |
| 2002/0031480 A1 | 3/2002 | Peart et al. |
| 2002/0035945 A1 | 3/2002 | Knowlton et al. |
| 2002/0037437 A1 | 3/2002 | Yamamoto |
| 2002/0037828 A1 | 3/2002 | Wilson et al. |
| 2002/0058009 A1 | 5/2002 | Bartus et al. |
| 2002/0061281 A1 | 5/2002 | Osbakken et al. |
| 2002/0078946 A1 | 6/2002 | Sprinkel, Jr. et al. |
| 2002/0078955 A1 | 6/2002 | Nichols et al. |
| 2002/0086852 A1 | 7/2002 | Cantor |
| 2002/0097139 A1 | 7/2002 | Gerber et al. |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0032638 A1 | 2/2003 | Kim et al. |

(56) References Cited

U.S. PATENT DOCUMENTS

| | | |
|---|---|---|
| 2003/0037437 A1 | 2/2003 | Das et al. |
| 2003/0051728 A1 | 3/2003 | Lloyd et al. |
| 2003/0070738 A1 | 4/2003 | Hamilton |
| 2003/0106551 A1 | 6/2003 | Sprinkel et al. |
| 2003/0118512 A1 | 6/2003 | Shen |
| 2003/0131843 A1 | 7/2003 | Lu |
| 2003/0138508 A1 | 7/2003 | Novack et al. |
| 2004/0016427 A1 | 1/2004 | Byron et al. |
| 2004/0083919 A1 | 5/2004 | Hosey et al. |
| 2004/0096402 A1 | 5/2004 | Hodges et al. |
| 2004/0101481 A1 | 5/2004 | Hale et al. |
| 2004/0105818 A1 | 6/2004 | Every et al. |
| 2004/0162517 A1 | 8/2004 | Furst et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0000711 A1 | 1/2005 | Hurlstone et al. |
| 2005/0016550 A1 | 1/2005 | Katase |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2006/0032496 A1 | 2/2006 | Hale et al. |
| 2006/0120962 A1 | 6/2006 | Rabinowitz et al. |
| 2006/0193788 A1 | 8/2006 | Hale et al. |
| 2006/0247573 A1 | 11/2006 | Alexandre et al. |
| 2006/0257329 A1 | 11/2006 | Rabinowitz et al. |
| 2007/0122353 A1 | 5/2007 | Hale et al. |
| 2007/0286816 A1 | 12/2007 | Hale et al. |
| 2008/0038363 A1 | 2/2008 | Zaffaroni et al. |
| 2008/0216828 A1 | 9/2008 | Wensley |
| 2008/0299048 A1 | 12/2008 | Hale et al. |
| 2008/0306285 A1 | 12/2008 | Hale et al. |
| 2009/0062254 A1 | 3/2009 | Hale et al. |
| 2009/0180968 A1 | 7/2009 | Hale et al. |
| 2010/0006092 A1 | 1/2010 | Hale et al. |
| 2010/0055048 A1 | 3/2010 | Hale et al. |
| 2010/0065052 A1 | 3/2010 | Sharma et al. |
| 2010/0068155 A1 | 3/2010 | Lei et al. |
| 2010/0181387 A1 | 7/2010 | Zaffaroni et al. |
| 2010/0294268 A1 | 11/2010 | Wensley et al. |
| 2010/0300433 A1 | 12/2010 | Sharma et al. |
| 2011/0233043 A1 | 9/2011 | Cross et al. |
| 2011/0240013 A1 | 10/2011 | Hale et al. |
| 2011/0240014 A1 | 10/2011 | Bennett et al. |
| 2011/0240022 A1 | 10/2011 | Hodges et al. |
| 2011/0244020 A1 | 10/2011 | Hale et al. |
| 2011/0245493 A1 | 10/2011 | Rabinowitz et al. |
| 2011/0253135 A1 | 10/2011 | Hale et al. |
| 2012/0048963 A1 | 3/2012 | Sharma et al. |
| 2012/0174918 A1* | 7/2012 | Kaar et al. ............ 128/200.23 |
| 2013/0032139 A1 | 2/2013 | Hale et al. |
| 2013/0180525 A1 | 7/2013 | Cross et al. |
| 2014/0060525 A1 | 3/2014 | Hale et al. |
| 2014/0060532 A1 | 3/2014 | Hodges et al. |
| 2014/0066618 A1 | 3/2014 | Hale et al. |
| 2014/0072605 A1 | 3/2014 | Bennett et al. |

FOREIGN PATENT DOCUMENTS

| | | |
|---|---|---|
| CN | 1082365 | 2/1994 |
| CN | 1176075 | 3/1998 |
| DE | 561103 | 1/1928 |
| DE | 571 289 | 2/1933 |
| DE | 26 48 308 | 4/1978 |
| DE | 35 42 447 | 6/1987 |
| DE | 195 46 341 | 1/1997 |
| DE | 196 16 627 | 11/1997 |
| DE | 198 54 007 | 5/2000 |
| DE | 198 54 009 | 5/2000 |
| EP | 0 039 369 | 11/1981 |
| EP | 0 244 837 | 11/1987 |
| EP | 0 264 195 | 4/1988 |
| EP | 0 274 431 | 7/1988 |
| EP | 0 277 519 | 8/1988 |
| EP | 0 279 796 | 8/1988 |
| EP | 0 358 114 | 3/1990 |
| EP | 0 363 494 | 4/1990 |
| EP | 0 430 559 | 6/1991 |
| EP | 0 430 566 | 6/1991 |
| EP | 0 492 485 | 7/1992 |
| EP | 0 532 194 | 3/1993 |
| EP | 0 606 486 | 7/1994 |
| EP | 1 325 761 | 10/1995 |
| EP | 0 734 719 | 2/1996 |
| EP | 0 780 659 | 6/1997 |
| EP | 0 816 674 A1 | 1/1998 |
| EP | 0 936 205 | 8/1999 |
| EP | 0 967 214 | 12/1999 |
| EP | 1 065 296 | 1/2001 |
| EP | 1 079 002 | 2/2001 |
| EP | 1 080 720 | 3/2001 |
| EP | 1 177 793 | 2/2002 |
| EP | 1 222 938 | 7/2002 |
| EP | 0 808 635 B1 | 7/2003 |
| EP | 1 345 268 A2 | 9/2003 |
| FR | 921 852 A | 5/1947 |
| FR | 1 289 468 | 4/1962 |
| FR | 2 234 532 | 1/1975 |
| FR | 2 428 068 A | 1/1980 |
| FR | 2 506 927 | 12/1982 |
| GB | 502 761 | 1/1938 |
| GB | 903 866 | 8/1962 |
| GB | 1 001 901 | 8/1965 |
| GB | 1 366 041 | 9/1974 |
| GB | 2 049 651 | 12/1980 |
| GB | 2 108 390 | 5/1983 |
| GB | 2 123 948 | 2/1984 |
| HU | 200105 B | 10/1988 |
| HU | 219392 B | 6/1993 |
| JP | 57 078968 | 5/1982 |
| JP | 58 225001 | 12/1983 |
| JP | S63-20298 | 6/1988 |
| WO | WO 85/00520 | 2/1985 |
| WO | WO 88/08304 | 11/1988 |
| WO | WO 90/07333 | 7/1990 |
| WO | WO 91/07947 | 6/1991 |
| WO | WO 92/05781 | 4/1992 |
| WO | WO 92/15353 | 9/1992 |
| WO | WO 92/19303 | 11/1992 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13290 | 5/1996 |
| WO | WO 96/31198 | 10/1996 |
| WO | WO 97/17948 | 5/1997 |
| WO | WO 97/27804 | 8/1997 |
| WO | WO 97/35582 | 10/1997 |
| WO | WO 97/40819 | 11/1997 |
| WO | WO 98/02186 | 1/1998 |
| WO | WO 98/16205 | 4/1998 |
| WO | WO 98/29110 | 7/1998 |
| WO | WO 98/34595 | 8/1998 |
| WO | WO 98/36651 | 8/1998 |
| WO | WO 98/37896 | 9/1998 |
| WO | WO 99/04797 | 2/1999 |
| WO | WO 99/11311 | 3/1999 |
| WO | WO 99/16419 | 4/1999 |
| WO | WO 99/24433 | 5/1999 |
| WO | WO 99/37347 | 7/1999 |
| WO | WO 99/59710 | 11/1999 |
| WO | WO 00/00176 | 1/2000 |

(56) References Cited

FOREIGN PATENT DOCUMENTS

| | | |
|---|---|---|
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28844 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/43801 | 6/2001 |
| WO | WO 01/66064 | 9/2001 |
| WO | WO 01/69136 | 9/2001 |
| WO | WO 01/80829 | 11/2001 |
| WO | WO 01/95903 | 12/2001 |
| WO | WO 02/00198 | 1/2002 |
| WO | WO 02/024158 | 3/2002 |
| WO | WO 02/051466 | 7/2002 |
| WO | WO 02/051469 | 7/2002 |
| WO | WO 02/056866 | 7/2002 |
| WO | WO 02/060870 | 8/2002 |
| WO | WO 02/083119 | 10/2002 |
| WO | WO 02/094232 | 11/2002 |
| WO | WO 02/094234 | 11/2002 |
| WO | WO 02/094236 | 11/2002 |
| WO | WO 02/094242 | 11/2002 |
| WO | WO 02/098389 | 12/2002 |
| WO | WO 02/098496 | 12/2002 |
| WO | WO 02/102297 | 12/2002 |
| WO | WO 03/021158 | 3/2003 |
| WO | WO 03/024456 | 3/2003 |
| WO | WO 03/037412 | 5/2003 |
| WO | WO 03/049535 | 6/2003 |
| WO | WO 03/095012 | 11/2003 |
| WO | WO 2004/001396 | 12/2003 |
| WO | WO 2004/011396 | 2/2004 |
| WO | WO 2004/054551 | 7/2004 |
| WO | WO 2004/104490 | 12/2004 |
| WO | WO 2004/104491 | 12/2004 |
| WO | WO 2004/104492 | 12/2004 |
| WO | WO 2004/104493 | 12/2004 |
| WO | WO 2004/106268 | 12/2004 |
| WO | WO 2006/029089 | 3/2006 |
| WO | WO 2006/022714 | 3/2009 |

OTHER PUBLICATIONS

Office Action mailed Jul. 3, 2006 with respect to U.S. Appl. No. 10/057,198.
Office Action mailed Sep. 20, 2005 with respect to U.S. Appl. No. 10/057,198.
Office Action mailed Dec. 4, 2003 with respect to U.S. Appl. No. 10/057,198.
Office Action mailed Jan. 12, 2005 with respect to U.S. Appl. No. 10/057,197.
Office Action mailed Jun. 3, 2004 with respect to U.S. Appl. No. 10/057,197.
Office Action mailed Jun. 5, 2007 with respect to U.S. Appl. No. 10/057,197.
Office Action mailed Sep. 21, 2006 with respect to U.S. Appl. No. 10/057,197.
Office Action mailed Dec. 15, 2003 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No. 10/146,080.
Office Action mailed Feb. 12, 2007 with respect to U.S. Appl. No. 10/146,086.
Office Action mailed Oct. 30, 2007 with respect to U.S. Appl. No. 10/146,086.
Office Action mailed Dec. 13, 2005 with respect to U.S. Appl. No. 10/146,086.
Office Action mailed Feb. 16, 2007 with respect to U.S. Appl. No. 10/146,088.
Office Action mailed Sep. 28, 2007 with respect to U.S. Appl. No. 10/146,088.
Office Action mailed Nov. 21, 2007 with respect to U.S. Appl. No. 10/146,088.
Office Action mailed Mar. 8, 2005 with respect to U.S. Appl. No. 10/718,982.
Office Action mailed Jan. 22, 2007 with respect to U.S. Appl. No. 10/851,429.
Office Action mailed May 9, 2006 with respect to U.S. Appl. No. 10/851,429.
Office Action mailed Oct. 4, 2007 with respect to U.S. Appl. No. 10/851,429.
Office Action mailed Jan. 24, 2007 with respect to U.S. Appl. No. 10/851,883.
Office Action mailed May 10, 2006 with respect to U.S. Appl. No. 10/851,883.
Office Action mailed Sep. 18, 2007 with respect to U.S. Appl. No. 10/851,883.
Office Action mailed Jan. 30, 2007 with respect to U.S. Appl. No. 10/851,432.
Office Action mailed May 3, 2006 with respect to U.S. Appl. No. 10/851,432.
Office Action mailed Sep. 18, 2007 with respect to U.S. Appl. No. 10/851,432.
Office Action mailed Mar. 5, 2007 with respect to U.S. Appl. No. 10/917,735.
Office Action mailed Dec. 11, 2007 with respect to U.S. Appl. No. 10/917,735.
Al-Awadi et al. (2005) "Kinetics and Mechanism of Thermal Gas-Phase Elimination of 13-Substituted Carboxylic Acids" Tetrahedron, 61:5769-5777.
Anderson, M.E. (1982). "Recent Advances in Methodology and Concepts for Characterizing Inhalation Pharmacokinetic Parameters in Animals and Man," Drug Metabolism Reviews. 13(5):799-826.
Anonymous, (Jun. 1998) Guidance for Industry: Stability testing of drug substances and products, U.S. Department of Health and Human Services, FDA, CDER, CBER , pp. 1-110.
Bacigalupo et al. (1999) "Time-Resolved Fluoroimmunoassay for $\Delta^9$-Tetrahydrocannabinol As Applied to Early Discrimination of Cannabis sativa Plants" Journal of Agricultural and Food Chemistry, 47:2743-2745.
Banhart (2000) JOM 22-27.
Banhart (2001) Prog. In Mater. Sci. 46:559-632.
Bastin, R. J. et al. (2000) "Salt Selection and Optimisation Procedures for Pharmaceutical New Chemical Entities", Organic Process Research & Development 4:427-435.
Bennett, R. L. et al. (1981). "Patient-Controlled Analgesia: A New Concept of Postoperative Pain Relief," Annual Surg. 195(6):700-705.

(56) References Cited

OTHER PUBLICATIONS

Benowitz (1994). "Individual Differences in Nicotine Kinetics and Metabolism in Humans," NIDA Research Monography, 2 pages.

Berkó et al. (2002) "In vitro and in Vivo Study in Rats of Rectal Suppositories Containing Furosemide." European Journal of Pharmaceutics and Biopharmaceutics vol. 53:311-315.

Bigal, et al. (2002) "Intravenous Chlorpromazine in the Emergency Department Treatment of Migraines: A Randomized Controlled Trial." *The Journal of Emergency Medicine* vol. 23, No. 2: 141-148.

Blanda et al. (2001) "Intranasal Lidocaine for the Treatment of Migraine Headache: A Randomized, Controlled Trial" *Academic Emergency Medicine* vol. 8:337-342.

Bowden, et al. (1988) "The Effect of Trifluoperazine on Bronchial Responsiveness in Asthma" *Clinical and Experimental Pharmacology & Physiology* 15: 457-463.

BP: Chemicals Products-Barrier Resins (1999). located at <http://www.bp.com/chemicals/products/product.asp> (visited on Aug. 2, 2001), 8 pages.

Brand, P. et al. (Jun. 2000). "Total Deposition of Therapeutic Particles During Spontaneous and Controlled Inhalations," Journal of Pharmaceutical Sciences. 89(6):724-731.

Caley, C.F. et al. (1998) "Focus on Quetiapine: the Fourth Atypical Antipsycotic" Formulary col. 33 No. 2: 105-119.

Campbell, Fiona A. et al. (2001) "Are Cannabinoids an Effective and Safe Treatment Option in the Management of Pain? A Qualitative Systemic Review," BMJ, 323 pp. 1-6.

Carroll, M.E. et al. (1990), "Cocaine-Base Smoking in Rhesus Monkey: Reinforcing and Physiological Effects," Psychopharmacology (Berl) 102:443-450.

Cavaliere et al. (2002) "Furosemide Protective Effect Against Airway Obstruction." Website http://www.bentham.org/sample-issues/cdt3-3/cavaliere/cavaliere-ms.htm.

Caviness, Verne S. (May, 1980) "Cluster Headache: Response to Chlorpromazine" *Headache* 128-131.

Cichewicz, Diana L. et al. (May 1999) "Enhancement of Mu Opioid Antinociception by Oral DELTA 9—Tetrahydrocannabinol: Dose Response Analysis and Receptor Identification" Journal of Pharmacology and Experimental Therapeutics vol. 289 (2): 859-867.

Clark, A. and Byron, P. (1986). "Dependence of Pulmonary Absorption Kinetics on Aerosol Particle Size," Z. Erkrank. 166:13-24.

Collins, et al. (2001) "Intravenous Administration of Prochlorperazine by 15-Minute Infusion Versus 2-Minute Bolus Does Not Affect the Incidence of Akathisia: A prospective Randomized, Controlled Trial" *Annals of Emergency Medicine* 38:5 491-496.

Coppola et al. (1995) "Randomized, Placebo-Controlled Evaluation of Prochlorperazine Versus Metoclopramide for Emergency Department Treatment of Migraine Headache" *Annals of Emergency Medicine* vol. 25 No. 5.

Coppola et al. (1995) Abstract: "A Prospective, Double-blind Evaluation of Prochlorperazine vs. Sumatriptan for the Emergency Department Treatment of Migraine Headache." *Annual Meeting Abstracts* vol. 2 No. 5:367-368.

Crabbe et al. (1971) "Synthesis of New Heterocyclic Derivatives of Estradiol" Tetrahedron 27:711-725.

Dahloef, et al. (1998) "Pathophysiology and Pharmacology of Migraine. Is There a Place for Antiemetics in Future Treatment Strategies" *Cephalagia* vol. 18: 594-604.

Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419-422, Darquenne, C. et al. (1997). "Aerosol Dispersion in Human Lung: Comparison Between Numerical Simulations and Experiments for Bolus Tests," American Physiological Society. 966-974.

Database Biosis "Online!" Biosciences Information Service, Philadelphia, PA 1979, Knight, V. et al., "Amantadine Aerosol in Humans", database accession No. PREV 198069035552 abstract, & Antimicrobial Agents and Chemotherapy 16(5):572-578.

Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3) 350-354.

Database WPI, Section CH, Week 198941, Derwent Publications Ltd., London, GB; Class B07, AN 1989-297792 AP002230849 & JP 01 221313 (NIPPON CREATE 1(K), Sep. 4, 1989, abstract.

Davies, C. N. et al. (May 1972). "Breathing of Half-Micron Aerosols," Journal of Applied Physiology. 32(5):591-600.

De Yong et al. (1998) "Radiative Ignition of Pyrotechnics: Effect of Wavelength on Ignition Threshold" Propellants, Explosives, Pyrotechnics 23:328-332.

Dershwitz, M., M.D., et al. (Sep. 2000). "Pharmacokinetics and Pharmacodynamics of Inhaled Versus Intravenous Morphine in Healthy Volunteers," Anesthesiology. 93(3): 619-628.

Dettmer et al. (2001) "Take Home Naloxone and the Prevention of Deaths From Opiate Overdose: Two Pilot Schemes." BMJ 322:895-896.

Donohue et al. (1995) Abstract: "Prochlorperazine Versus Sumatriptan for Emergency Department Therapy of Migraine Headache" *Annals of Emergency Medicine* vol. 25 No. 1: 154.

Dormans et al. (1996) "Vascular Effects of Loop Diuretics." Cardiovascular Research 32:988-997.

Drotts, et al. (1999) Ann. Emerg. Med. 34: 469-475.

Drug Information Handbook, 2nd edition, Lexi-Comp, Inc.: Cleveland, 1994-1995, pp. 554-555.

Drugs Approved by the FDA—Drug Name: Nicotrol Inhaler (2000) located at <http://www.centerwatch.com/patient/drugs/dru202.html> (Visited on Aug. 2, 2001), 2 pages.

Faris et al. (2002) "Current Evidence Supporting the Role of Diuretics in Heart Failure: a Meta Analysis of Randomized Controlled Trials." International Journal of Cardiology vol. 82:149-158.

Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.

Finlay, W. H. (2001). "The Mechanics of Inhaled Pharmaceutical Aerosols", Academic Press: San Diego Formula 2.39. pp. 3-14 (Table of Contents). pp. v-viii.

Galeotti Nicoletta et al. (2002). "Indomethacin Caffeine and Prochlorperazine Alone and Combined Revert Hyperalgesia in iN Vivo Models of Migraine", Pharmacological research, vol. 46. No. 3: 245-250.

Ginder et al. (2000) "A Prospective Study of I.V. Magnesium and I.V. Prochlorperazine in the Treatment of Headaches" *The Journal of Emergency Medicine*: vol. 18 No. 3: 311-315.

Gleeson, et al. (1982) "Chlorpromazine Hyperalgesia Antagonizes Clonidine Analgesia, but Enhances Morphine Analgesia in Rats Tested in a Hot-Water Tail-Flick Paradigm" Psychopharmacology vol. 78: 141-146.

Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.

Goodall et al. (Sep. 1, 2002) Journal of Aerosol Medicine 15(3):351-357 doi:10.1089/089426802760292717.

Gottlieb, S.S. "Renal Effects of Adenosine A1-Receptor Antagonists in Congestive Heart Failure," Drugs, 2001, 61(10), pp. 1387-1393 (abstract only).

Hagenbach, Charles "Prochlorperazine in the Prophylaxis of Migraine" General Practioners' Forum pp. 503-506.

Hamon, et al. (1987) "Opioid Receptors and Neuropeptides in the CNS in Rats Treated Chronically with Amoxapine and Amitriptyline" Neuropharmacology vol. 26 No. 6: 531-539.

Hansh et al. (1990) Comprehensive medicinal chemistry 5:251-278, Pharmacogenetics.

Hatsukami D., et al. (May 1990) "A Method for Delivery of Precise Doses of Smoked Cocaine-Base to Human." Pharmacology Biochemistry & Behavior. 36(1):1-7.

Kreith, Frank et al. "Boundary-Layer Fundamentals" *Principles of Heat Transfer*. Section 4.3: p. 236-242.

(56) References Cited

OTHER PUBLICATIONS

Nielsen et al. (2000) "Intranasal Administration of Different Liquid Formulation of Bumetanide to Rabbits" International Journal of Pharmaceutics 204:35-41.

Panipol Conductive Inks website (www.panipol.com).

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Perfetti (1983) "Structural Study of Nicotine Salts" Beitraege zur Tabakforschung Internatioal 12(2):43-54.

Perfetti (2000) "The Transfer of Nicotine from Nicotine Salts to Mainstream Smoke" Beitraege zur Tabakforschung International 19(3):141-158.

Polosa et al. (1995) "Inhaled Loop Diuretics and Basal Airway Responsiveness in Man: Evidence of a Role for Cyclo-oygenase Products." Eur. Respir. J 8(4):593-599.

Roux, Gillard M. "Laser Diode Ignition of the Combustion of Pyrotechnic Mixtures. Experimental Study of the Ignition of $Zr/KClO_4$ and $Zr/PbCrO_4$".

Rozen et al. (2001) "Olanzapinea as an Abortive Agent for Cluster Headache." *Headache* vol. 41:813-816.

Shimoyama et al. (2002) "Nebulized Furosemide as a Novel Treatment for Dyspnea in Terminal Cancer Patients." Journal of Pain and Symptom Management vol. 23 No. 1: 73:76.

Shrestha et al. (1996) "Ketorolac vs Chlorpormazine in the Treatment of Acute Migraine Without Aura." *Arch. Intern. Med.* vol. 156:1725-1728.

Wilknson M. (1985). "Migraine-Treatment of Acute Attack", Scottish Medical Journal vol. 30 No. 4: 258-262.

U.S. Appl. No. 13/311,660, filed Dec. 6, 2011, Bennett et al.
U.S. Appl. No. 13/597,865, filed Aug. 29, 2012, Bennett et al.
U.S. Appl. No. 14/675,275, filed Mar. 31, 2015, Damani et al.
U.S. Appl. No. 14/624,311, filed Feb. 17, 2015, Hale et al.

\* cited by examiner

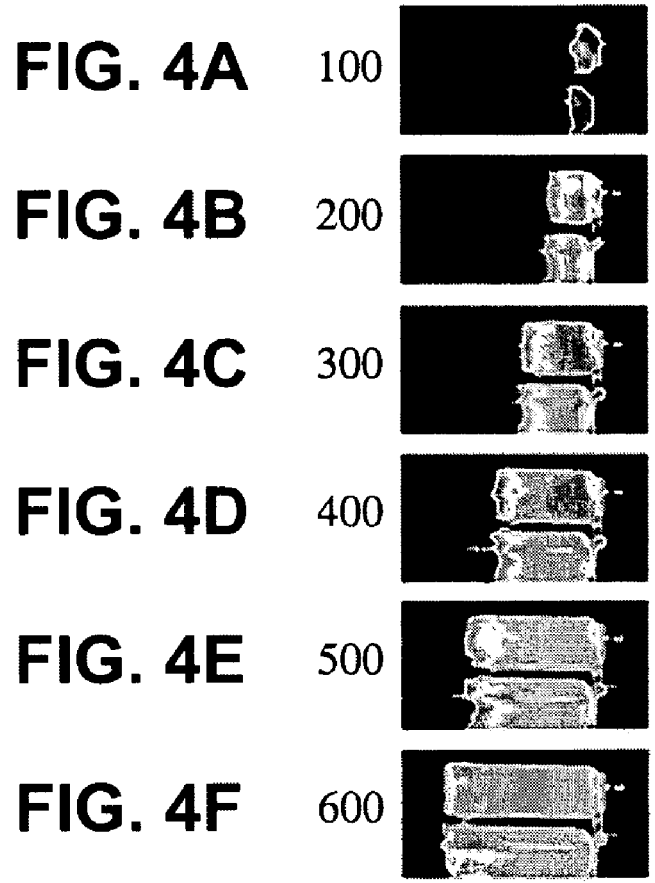

$t = 0$ms $t = 150$ms $t = 250$ms $t = 500$ms $t = 1000$ms

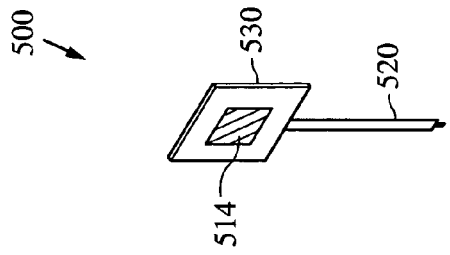
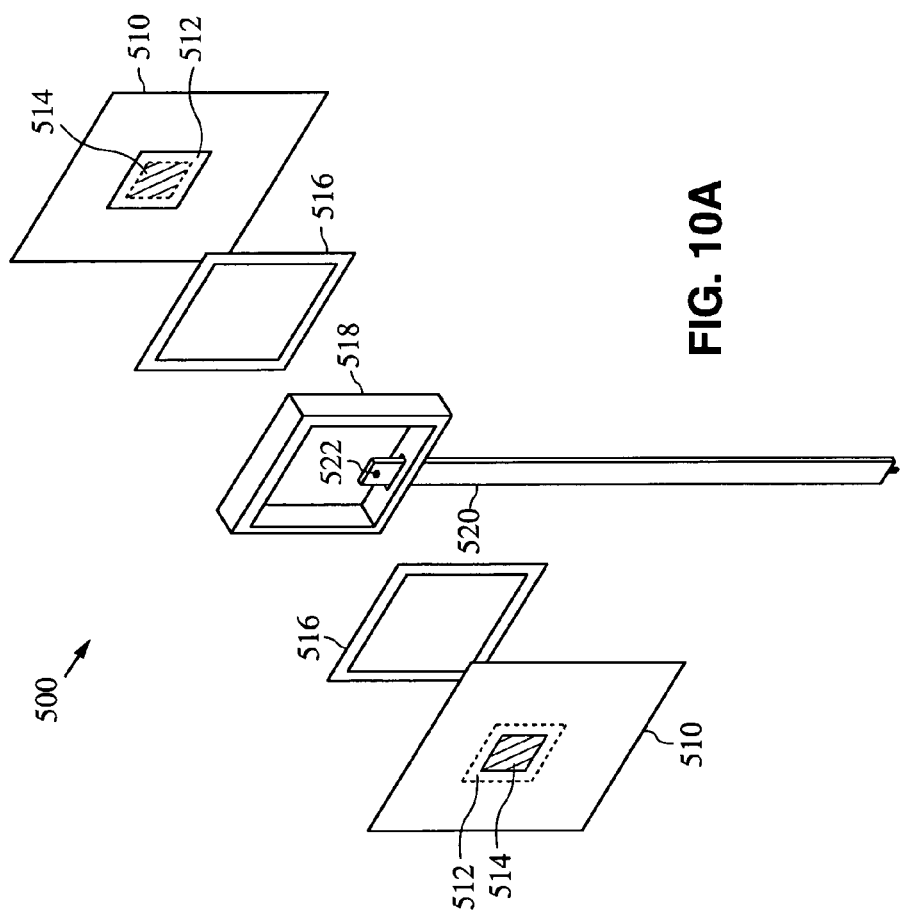

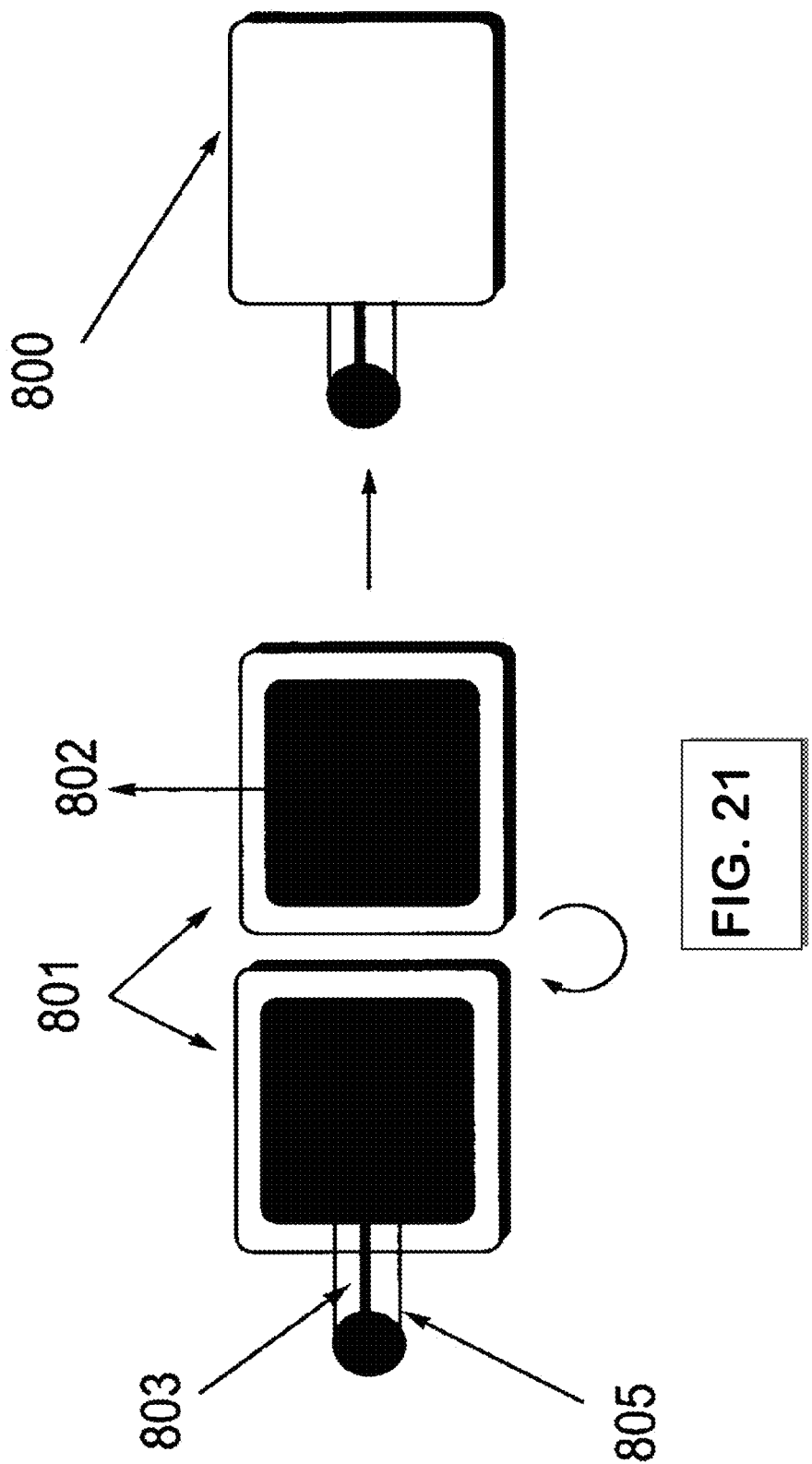

SELF-CONTAINED HEATING UNIT AND DRUG-SUPPLY UNIT EMPLOYING SAME

REFERENCE TO RELATED APPLICATIONS

This application is a continuation of U.S. application Ser. No. 13/783,508, filed Mar. 4, 2013, now U.S. Pat. No. 8,991,387 which is a continuation of U.S. application Ser. No. 12/485,704, filed Jun. 16, 2009, now U.S. Pat. No. 8,387,612 which is a continuation-in-part of U.S. application Ser. No. 10/850,895 filed May 20, 2004, now abandoned, and is a continuation-in-part of U.S. application Ser. No. 10/851,429 filed May 20, 2004, now abandoned, and is a continuation-in-part of U.S. application Ser. No. 10/851,883 filed May 20, 2004, now abandoned, and is a continuation-in-part of U.S. application Ser. No. 10/851,432 filed May 20, 2004, now abandoned. These applications claim priority to U.S. provisional application Ser. No. 60/472,697 entitled "Self-Contained Heating Unit and Drug-Supply Unit Employing Same," filed May 21, 2003, now expired, Hale et al. The entire disclosures of which are hereby incorporated by reference. Any disclaimer that may have occurred during the prosecution of the above-referenced applications is hereby expressly rescinded, and reconsideration of all relevant art is respectfully requested.

This invention was made with Government support under Grant No. R44 NS044800, awarded by the National Institutes of Health. The Government has certain rights in the invention.

FIELD

This disclosure relates to heating units capable of rapid heating and to articles and methods employing such heating units.

INTRODUCTION

Self-contained heat sources are employed in a wide-range of industries, from food industries for heating food and drink, to outdoor recreation industries for providing hand and foot warmers, to medical applications for inhalation devices. Many self-contained heating sources are based on either an exothermic chemical reaction or on ohmic heating. For example, self-heating units that produce heat by an exothermic chemical reaction often have at least two compartments, one for holding a heat-producing composition and one for holding an activating solution. The two compartments are separated by a frangible seal, that when broken allows mixing of the components to initiate an exothermic reaction to generate heat. (see for example U.S. Pat. Nos. 5,628,304; 4,773,389; 6,289,889). This type of non-combustible, self-heating unit is suitable for heating food, drink, or cold toes and fingers, since the heat production is relatively mild.

Another common source for self-contained heat is ohmic heating. In ohmic heating a current is passed through an electrically resistive material to generate heat that is transmitted to an adjacent article. This mode of heat production has been employed to vaporize or heat a volatile substance, for example tobacco, for inhalation by a user. Cigarette holders and pipe bowls having an electrical resistance coil to generate heat in order to volatilize tobacco flavors have been described (U.S. Pat. Nos. 2,104,266; 4,922,901; 6,095,143). Heating of drugs other than tobacco by ohmic heating have also been described. For example, WO 94/09842 to Rosen describes applying a drug to an electrically resistive surface and heating the surface to vaporize the drug for inhalation. Ohmic heating has the advantage of facilitating precise control of the energy applied to determine the heat generated. However, in many ohmic heating systems, and in particular for small systems where limited energy is available, such as, for example, when using batteries, there can be a substantial delay on the order of seconds or minutes between the time heating is initiated and maximum temperature is achieved. Moreover, for small devices, such as for example, portable medical devices, where the power source comprises a battery, ohmic heating can be expensive and bulky.

Another approach for providing a controlled amount of heat is using electrochemical interactions. Here, components that interact electrochemically after initiation in an exothermic reaction are used to generate heat. Exothermic electrochemical reactions include reactions of a metallic agent and an electrolyte, such as a mixture of magnesium granules and iron particles as the metallic agent, and granular potassium chloride crystals as the electrolyte. In the presence of water, heat is generated by the exothermic hydroxylation of magnesium, where the rate of hydroxylation is accelerated in a controlled manner by the electrochemical interaction between magnesium and iron, which is initiated when the potassium chloride electrolyte dissociates upon contact with the liquid water. Electrochemical interactions have been used in the smoking industry to volatilize tobacco for inhalation (U.S. Pat. Nos. 5,285,798; 4,941,483; 5,593,792).

The aforementioned self-heating methods are capable of generating heat sufficient to heat an adjacent article to several hundred degrees Celsius in a period of several minutes. There remains a need in the art for a device capable of rapid heat production, i.e., on the order of seconds and fractions of seconds, capable of heating an article to within a defined temperature range, and which is suitable for use in articles to be used by people.

SUMMARY

Certain embodiments include a heating unit comprising an enclosure comprising a substrate having an exterior surface and an interior surface, wherein the substrate has a thickness in the range of 0.001 to 0.020 inches; a layer of solid fuel covering an area of the interior surface of the substrate corresponding to an area of the exterior surface of the substrate to be heated, wherein the solid fuel layer has a thickness in the range of 0.001 to 0.030 inches and wherein the solid fuel is configured to heat a portion of the exterior surface of the at least one substrate to a temperature of at least 200° C. within 1 second follow ignition of the solid fuel; and an igniter disposed at least partially within the enclosure for igniting the solid fuel. In certain embodiments, within 1 second after ignition of the solid fuel, no more than 10% of said area of the exterior surface has a temperature 50° C. to 100° C. less than the remaining 90% of said area of the exterior surface. Additionally, in certain embodiments, within 500 milliseconds after ignition of the solid fuel, no more than 10% of said area of the exterior surface has a temperature 50° C. to 100° C. less than the remaining 90% of said area of the exterior surface. In certain embodiments, within 250 milliseconds after ignition of the solid fuel, no more than 10% of said area of the exterior surface has a temperature 50° C. to 100° C. less than the remaining 90% of said area of the exterior surface. In certain embodiments, the thin layer of solid fuel has a thickness in the range of 0.001 to 0.005 inches. In certain embodiments, the enclosure comprises more than one substrate. In certain embodiments, the substrate is a metal foil having a thickness in the range of 0.001 to 0.010 inches.

Certain embodiments include a heating unit, wherein the solid fuel comprises a metal reducing agent and a metal containing oxidizing agent. In certain embodiments, the metal containing oxidizing agent is selected from at least one of the following: $MoO_3$, $KClO_4$, $KClO_3$, and $Fe_2O_3$. In certain embodiments, the metal reducing agent is selected from at least one of the following: aluminum, zirconium, iron, and titanium. In certain embodiments, the amount of metal reducing agent comprises from 60% to 90% by weight of the total dry weight of the solid fuel. In certain embodiments, the amount of metal reducing agent comprises from 10% to 40% by weight of the total dry weight of the solid fuel.

Certain embodiments include a heating unit, wherein the solid fuel comprises at least one additive material. In certain embodiments, the additive material is selected from at least one of the following: a clay gelling agent, nitrocellulose, polyvinylalcohol, diatomaceous earthy glass beads and a colloidal silica.

Certain embodiments include a heating unit, wherein the substrate has a thickness in the range of 0.002 to 0.010 inches. In certain embodiments, the substrate has a thickness in the range of 0.002 to 0.005 inches.

Certain embodiments include a heating unit, wherein the substrate is a metal, an alloy, or a ceramic.

Certain embodiments include a heating unit, wherein the igniter comprises: an optical window in the enclosure; and a light sensitive initiator composition disposed within the enclosure. In certain embodiments, the initiator composition comprises a reducing agent and an oxidizing agent. In certain embodiments, the reducing agent of the initiator composition is selected from at least one of the following: zirconium, titanium, and aluminum. In certain embodiments, the oxidizing agent of the initiator composition is selected from at least one of the following: molybdenum trioxide, potassium perchlorate, copper oxide, and tungsten trioxide. In certain embodiments, the initiator composition comprises aluminum, boron, molybdenum trioxide, and a clay gelling agent.

Certain embodiments include a heating unit, wherein the substrate comprises a multi-layer structure. In certain embodiments, substrate is a polyimide, a polyester, or a fluoropolymer.

Certain embodiments include a heating unit, wherein the igniter is a percussive igniter. In certain embodiments, at least one impulse absorbing material is disposed within the enclosure. In certain embodiments, a spacer provides an empty volume within the enclosure.

Certain embodiments include a heating unit, wherein at the least one substrate is a metal, an alloy, or a ceramic.

Certain embodiments include a heating unit, wherein the enclosure is capable of withstanding an internal pressure of at least 50 psig.

Certain embodiments include a heating unit, wherein a drug layer is on a portion of the exterior surface of the at least one substrate.

Certain embodiments disclose methods of controlling uniformity of temperature and peak temperature of a substrate surface by coating a thin layer of a selected mass of a solid fuel on a surface of the substrate.

Certain embodiments include heating units comprising an enclosure and a solid fuel capable of undergoing an exothermic metal oxidation-reduction reaction disposed within the enclosure. The solid fuel in these heating units can be actuated using a variety of ignition systems.

Certain embodiments include drug supply units comprising an enclosure having at least one substrate having an exterior surface and an interior surface, a solid fuel capable of undergoing an exothermic metal oxidation-reduction reaction disposed within the enclosure, and a drug disposed on a portion of the exterior surface of the substrate.

Certain embodiments include drug delivery devices comprising a housing defining an airway, a heating unit comprising an enclosure having at least one substrate having an exterior surface and an interior surface, and a solid fuel capable of undergoing an exothermic metal oxidation-reduction reaction disposed within the enclosure, a drug disposed on a portion of the exterior surface of the substrate, wherein the portion of the exterior surface comprising the drug is configured to be disposed within the airway, and an igniter configured to ignite the solid fuel.

Certain embodiments include methods of producing an aerosol of a drug and of treating a disease in a patient using such heating units, drug supply units, and drug delivery devices.

It is to be understood that both the foregoing general description and the following detailed description are exemplary and explanatory only and are not restrictive of certain embodiments, as claimed.

DESCRIPTION OF THE DRAWINGS

FIGS. 4A-4F are thermal images of a cylindrically-shaped heating unit measured using an infrared thermal imaging camera at post-ignition times of 100 milliseconds (FIG. 4A), 200 milliseconds (FIG. 4B), 300 milliseconds (FIG. 4C), 400 milliseconds (FIG. 4D), 500 milliseconds (FIG. 4E), and 600 milliseconds (FIG. 4F) according to certain embodiments.

FIGS. 10A-10B show illustrations of a perspective view (FIG. 10A) and an assembly view (FIG. 10B) of a thin film drug supply unit according to certain embodiments;

Figure 1A:
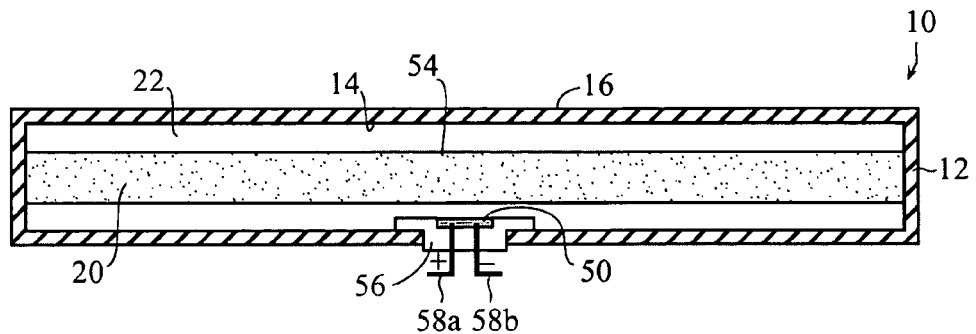
FIGS. 1A-1B are cross-sectional illustrations of heating units according to certain embodiments.

In certain embodiments, an oxidizing agent can comprise oxygen, an oxygen based gas, and/or a solid oxidizing agent. In certain embodiments, an oxidizing agent can comprise a metal-containing oxidizing agent. In certain embodiments, a metal-containing oxidizing agent includes, but is not limited to, perchlorates and transition metal oxides. Perchlorates can include perchlorates of alkali metals or alkaline earth metals, such as, but not limited to, potassium perchlorate ($KClO_4$), potassium chlorate ($KClO_3$), lithium perchlorate ($LiClO_4$), sodium perchlorate ($NaClO_4$), and magnesium perchlorate [$Mg(ClO_4)_2$]. In certain embodiments, transition metal oxides that function as oxidizing agents include, but are not limited to, oxides of molybdenum, such as $MoO_3$, iron, such as $Fe_2O_3$, vanadium ($V_2O_5$), chromium ($CrO_3$, $Cr_2O_3$), manganese ($MnO_2$), cobalt ($Co_3O_4$), silver ($Ag_2O$), copper ($CuO$), tungsten ($WO_3$), magnesium ($MgO$), and niobium ($Nb_2O_5$). In certain embodiments, the metal-containing oxidizing agent can include more than one metal-containing oxidizing agent.

In certain embodiments, the metal reducing agent forming the solid fuel can be selected from zirconium and aluminum, and the metal-containing oxidizing agent can be selected from $MoO_3$ and $Fe_2O_3$.

The ratio of metal reducing agent to metal-containing oxidizing agent can be selected to determine the ignition temperature and the burn characteristics of the solid fuel. An exemplary chemical fuel can comprise 75% zirconium and 25% $MoO_3$, percentage based on weight. In certain embodiments, the amount of metal reducing agent can range from 60% by weight to 90% by weight of the total dry weight of the solid fuel. In certain embodiments, the amount of metal-containing oxidizing agent can range from 10% by weight to 40% by weight of the total dry weight of the solid fuel. In certain embodiments, the amount of oxidizing agent in the solid fuel can be related to the molar amount of the oxidizers at or near the eutectic point for the fuel composition. In certain embodiments, the oxidizing agent can be the major component and in others the metal reducing agent can be the major component. Those of skill in the art are able to determine the appropriate amount of each component based on the stoichiometry of the chemical reaction and/or by routine experimentation. Also as known in the art, the particle size of the metal and the metal-containing oxidizer can be varied to determine the burn rate, with smaller particle sizes selected for a faster burn (see, for example, U.S. Pat. No. 5,603,350).

In certain embodiments, a solid fuel can comprise additive materials to facilitate, for example, processing and/or to determine the thermal and temporal characteristics of a heating unit during and following ignition of the solid fuel. An additive material can be reactive or inert. An inert additive material will not react or will react to a minimal extent during ignition and burning of the solid fuel. The additive can comprise inorganic or organic materials. In certain applications, particularly, where it is desirous to produce a minimal amount of gas, such as for example, in a sealed heating unit, the additive material can be inorganic materials and can function as binders, adhesives, gelling agents, thixotropic agents, and/or surfactants. Examples of gelling agents include, but are not limited to, clays such as LAPONITE®, Montmorillonite, CLOISITE®, metal alkoxides, such as those represented by the formula R—$Si(OR)_n$ and $M(OR)_n$ where n can be 3 or 4, and M can be Ti, Zr, Al, B or other metals, and collidal particles based on transition metal hydroxides or oxides. Examples of binding agents include, but are not limited to, soluble silicates such as Na- or K-silicates, aluminum silicates, metal alkoxides, inorganic polyanions, inorganic polycations, and inorganic sol-gel materials, such as alumina or silica-based sols.

In certain embodiments, the solid fuel comprises LAPONITE®, and in particular LAPONITE® RDS, as an inert additive material. LAPONITE® is a synthetic layered silicate, and in particular a magnesium phyllosilicate, with a structure resembling that of the natural clay mineral hectorite ($Na_{0.4}Mg_{2.7}Li_{0.3}Si_4O_{10}(OH)_2$). LAPONITE® RD is a commercial grade material which, when added to water, rapidly disperses to form a gel when hydrated (Southern Clay Products, Gonzales, Tex.). LAPONITE® RD has the following chemical analysis in weight percent: 59.5% $SiO_2$:27.5% MgO:0.8% $Li_2O$:2.8% $Na_2O$. LAPONITE® RDS (Southern Clay Products, Gonzales, Tex.) is a commercially available sol-forming grade of LAPONITE® modified with a polyphosphate dispersing agent, or peptizer, to delay rheological activity until the LAPONITE® RDS is added as a dispersion into a formulation. A sol refers to a colloid having a continuous liquid phase in which solid is suspended in a liquid. LAPONITE® RDS has the following chemical analysis in weight percent: 54.5% $SiO_2$:26% MgO:0.8% $Li_2O$:5.6% $Na_2O$:4.1% $P_2O_5$, In the presence of electrolytes, LAPONITEs® can act as gelling and thixotropic agents. Thixotropy refers to the property of a material to exhibit decreased viscosity under shear.

When incorporated into a solid fuel composition comprising a metal reducing agent and a metal-containing oxidizing agent, such as any of those disclosed herein, in addition to imparting gelling and thixotropic properties, LAPONITE® RDS can also act as binder. A binder refers to an additive that produces bonding strength in a final product. The binder can impart bonding strength, for example, by forming a bridge, film, matrix, and/or chemically self-react and/or react with other constituents of the formulation.

In certain embodiments, for example, when the solid fuel is disposed on a substrate as a film or thin layer, wherein the thickness of the thin layer of solid fuel can range, for example, from 0.001 inches to 0.030 inches, it can be useful that the solid fuel adhere to the surface of the substrate and that the constituents of the solid fuel adhere to each other, and maintain physical integrity. In certain embodiments, it can be useful that the solid fuel remain adhered to the substrate surface and maintain physical integrity during processing, storage, and use during which time the solid fuel coating can be exposed to a variety of mechanical and environmental conditions. Several additives, such as those disclosed herein, can be incorporated into the solid fuel to impart adhesion and physical robustness to the solid fuel coating.

In certain embodiments, small amounts of LAPONITE® RDS added to a solid fuel slurry comprising a metal reducing agent and a metal-containing oxidizing agent can impart thixotropic, gelling and in particular, adhesive properties to the solid fuel.

An example of the preparation of a solid fuel comprising LAPONITE® RDS and the application of the solid fuel to a metal foil substrate are described in Example 1.

Other useful additive materials include glass beads, diatomaceous earth, nitrocellulose, polyvinylalcohol, and other polymers that may function as binders. In certain embodiments, the solid fuel can comprise more than one additive material. The components of the solid fuel comprising the metal, oxidizing agent and/or additive material and/or any appropriate aqueous- or organic-soluble binder, can be mixed by any appropriate physical or mechanical method to achieve a useful level of dispersion and/or homogeneity. In certain embodiments, the solid fuel can be degassed.

In addition to the enhanced binding properties of the solid fuels with additive, other advantages of using inorganic additives include stability of the additive up to very high temperatures and lack of, or minimal release of, any toxic gases by the additive. In an enclosed system, this lack of additional gas production from the inorganic additive also reduces or minimizes the possibility of rupture of the enclosed heating unit.

Tables 1A-1E summarize certain embodiments of solid fuel compositions including the additives used. The weight ratio of the components comprising certain solid fuel compositions are provided.

TABLE 1A

Embodiments of Solid Fuel Compositions (wt %)

| Component | Fuel #1 | Fuel #2 | Fuel #3 | Fuel #4 | Fuel #5 | Fuel #6 | Fuel #7 | Fuel #8 |
|---|---|---|---|---|---|---|---|---|
| Zirconium (Zr) | 70-90 | | | | | 20-40 | 20-30 | |
| Titanium (Ti) | | 70-92 | | | | | | 60-80 |
| Iron (Fe) | | | 70-90 | | | | | |
| Magnesium (Mg) | | | | 20-40 | 40-60 | | | |
| Boron (B) | | | | | | | | 20-40 |
| Potassium perchlorate (KClO$_4$) | 10-30 | 8-30 | 10-30 | | | | | |
| Lead Oxide (PbO) | | | | | 40-60 | | | |
| Tungsten Oxide (WO$_3$) | | | | | | 60-80 | | |
| Barium Chromate (BaCrO$_4$) | | | | | | | 70-80 | |
| Teflon | | | | 60-80 | | | | |

TABLE 1B

Embodiments of Solid Fuel Compositions (wt %)

| Component | Fuel #9 | Fuel #10 | Fuel #11 | Fuel #12 | Fuel #13 | Fuel #14 | Fuel #15 | Fuel #16 |
|---|---|---|---|---|---|---|---|---|
| Zirconium (Zr) | | | | 21 | | | 10-50 | |
| Titanium (Ti) | 60-80 | | 70-92 | | 82 | 55 | 33-81 | |
| Iron (Fe) | | | 0-84 | | | | | |
| Aluminum (Al) | | 20-40 | | | | 20 | | |
| Nickel (Ni) | | 60-80 | | | | | | |
| Boron (B) | | | | | | 25 | | |
| Potassium perchlorate (KClO$_4$) | | | 8-30 | | | | 9-17 | 50 |
| Potassium chlorate (KClO$_3$) | | | | | 18 | | | |
| Tungsten Oxide (WO$_3$) | 20-40 | | | | | | | |
| Barium Chromate (BaCrO$_4$) | | | | 64 | | | | |
| Zirconium Carbide (ZrC) | | | | | | | | 50 |
| Diatomaceous Earth | | | | 15 | | | | |

TABLE 1C

Embodiments of Solid Fuel Compositions (wt %)

| Component | Fuel #17 | Fuel #18 | Fuel #19 | Fuel #20 | Fuel #21 | Fuel #22 | Fuel #23 | Fuel #24 |
|---|---|---|---|---|---|---|---|---|
| Zirconium (Zr) | | 50-65 | | | 50-72 | 30-80 | 65 | 55-70 |
| Titanium (Ti) | | | 20-70 | | | | | |
| Boron (B) | | | | 15 | | | | |
| Potassium Perchlorate (KClO$_4$) | 52.5 | | | | | | | |
| Molybdenum Oxide (MoO$_3$) | | 0-50 | 30-80 | | | 20-70 | | 25-33 |
| Iron Oxide (Fe$_2$O$_3$) | | 0-50 | | 85 | 28-50 | | 25 | |
| Zirconium Hydride (ZrH$_2$) | 47.5 | | | | | | | |
| Diatomaceous Earth | | balance | | | | | 10 | 5-12 |

TABLE 1D

Embodiments of Solid Fuel Compositions (wt %)

| Component | Fuel #25 | Fuel #26 | Fuel #27 | Fuel #28 | Fuel #29 | Fuel #30 | Fuel #31 | Fuel #32 | Fuel #33 |
|---|---|---|---|---|---|---|---|---|---|
| Zirconium (Zr) | 35-50 | 63-69 | 70 | 34 | 66.5-69 | 66.5-74.6 | 54-66.5 | 69 | 69 |
| Titanium (Ti) | 20-35 | | | | | | | | |
| Molybdenum Oxide ($MoO_3$) | 30 | 27-29.5 | 30 | 54 | 28.5-29 | 24.87-29 | 28.5-34 | 29.85 | 29.85 |
| Nitrocellulose | | | excess | | | 0.53-4.5 | | 0.5 | 0.5 |
| Cab-O-Sil | | 4-7.5 | | | | | | | |
| Glass Fber | | | | 12 | | | | | 0.65 |
| Glass Microsphere | | | | | | | | 0.65 | |
| Polyvinyl Alcohol | | | | | 2.5-4.5 | | | | |
| High Vacuum Grease | | | | | | | 5-12 | | |

TABLE 1E

Embodiments of Solid Fuel Compositions (wt %)

| Component | Fuel #34 | Fuel #35 | Fuel #36 | Fuel #37 | Fuel #38 | Fuel #39 | Fuel #40 | Fuel #41 | Fuel #42 | Fuel #43 |
|---|---|---|---|---|---|---|---|---|---|---|
| Zirconium (Zr) | 66.5-69 | 69.65 | 69.7-74.6 | 49-59.5 | | | 47-70 | | 40 | 20 |
| Magnesium (Mg) | | | | | | 40 | | | | |
| Aluminum (Al) | | | | | 36-70 | | | 50-55 | 30 | |
| Silicon (Si) | | | | | | | | | | 30 |
| Potassium chlorate ($KClO_3$) | | | | | | | 0-3 | | | |
| Bismuth Oxide ($Bi_2O_3$) | | | | | | | | | | 50 |
| Molybdenum Oxide ($MoO_3$) | 28.5-29 | 29.85 | 24.9-29.8 | 21-25.5 | 30-64 | 40 | 23.1-38 | 45-50 | 30 | |
| Diatomaceous Earth | | | | 19-25 | | | balance or excess | | | |
| Nitrocellulose | | | | 0.5 | | | 0.4-2 | 1 | | |
| Glass Beads | | | | | | 20 | | | | |
| Carboxymethyl cellulose | | | | | | | | | | excess |
| Polyvinyl alcohol | | | 0.5 | | | | | | | |
| 40% Aqueous $SiO_2$ | 2-5 | | | | | | | | | |
| VITON ®-A | | 0.5 | | | | | | | | |

While the use of additives in the solid fuel can improve the binding properties of the solid fuel, it also can improve the ease of use and manufacturability of substrates coated with such fuel. In particular, use of additives can make it possible to use wet-coating techniques, such as, for example, but not limitation, dip coating, spray coating, roller coating, gravure coating, reverse roll coating, gap coating, metering rod coating, slot die coating, curtain coating, and air knife coating, as means for deposition of a fuel powder on a substrate surface, such as, for example, either inside, or on, a cylindrical type surface such as the internal surface of the substrate in FIG. 1C, or on a flat surface such as a foil as is shown in FIG. 10A.

The use of solid fuel slurries with additives for coating a substrate can provide for better mixing of the materials, enhanced adherence properties, and more control over the even disbursement of the solid fuel on a surface. While preparing a physical mixture of solid fuel powders as an essentially homogeneous layer around the walls of a cylindrical device can be done, it is problematic, especially if the materials used have differences in densities, particle sizes, shapes, surface volume ratios, and lack chemically attractive surface-surface interactions. (Essentially homogeneous is defined, for purposes herein, as essentially uniform; and when applied to a mixture of two or more components, it refers to a basically uniform distribution of the various different particles throughout the mixture. This is in contrast to a heterogeneous mixture of components where various components tend to aggregate and there is settling out of the higher density particles.) Use of a core for dispersing mixtures of fuel powders to an interior surface of a substrate, allows one to control the gap or layer thickness of the solid fuel layer; however, it does not prevent other problems such as segregation of the particles in the mixture. Inadequate homogeneity as to the fuel mixture itself, due to ineffective mixing can result in inconsistent heating of the exterior surface of the substrate. Mixing can be facilitated and even automated when done as a slurry as opposed to a dry powder.

Additionally, lack of homogeneity as to the fuel thickness on, or in, contact with an interior surface of a substrate can also result in inconsistent heating of the exterior surface of a substrate. Coating adherence and ease of application can be enhanced by the use of slurries with additives.

In certain embodiments, the solid fuel is disposed on a substrate as a coating or thin layer, wherein the thickness of the thin layer of solid fuel can range, for example, from 0.001 inches to 0.030 inches by use of wet coating Substrates such as, for example, substrates 510 shown in FIG. 10A, can be coated to a nearly homogeneous thickness to form a thin coating or a thin layer of solid fuel 512 on the interior region of the substrate corresponding to the exterior surface on which the drug 514 is disposed. The thickness of the substrate, its thermal conductivity, its heat capacity, the thickness of the thin layer of solid fuel 512, and the composition of solid fuel 512 can determine the maximum temperature (peak temperature) as well as the temporal and spatial dynamics of the temperature profile produced by the burning of the solid fuel.

In certain embodiments, the metal reducing agent and the oxidizing agent can be in the form of a powder. The term "powder" refers to powders, particles, prills, flakes, and any other particulate that exhibits an appropriate size and/or surface area to sustain self-propagating ignition. For example, in certain embodiments, the powder can comprise particles exhibiting an average diameter ranging from 0.1 µm to 200 µm.

In certain embodiments, a solid fuel can comprise a multilayer comprising reactants capable of undergoing a self-sustaining exothermic reaction. A multilayer solid fuel comprising alternating and/or interposed layers of materials capable of reacting exothermically, can be continuous, or can be discontinuous. Each of the multiple layers can be homogeneous or heterogeneous. A discontinuous layer refers to a layer that can be patterned and/or have openings. The use of discontinuous layers can increase the contact to the reactions; and by bringing the reactants into proximity, can thereby facilitate the exothermic reaction. Each layer can comprise one or more reactants, and can comprise one or more additive materials such as binders, gelling agents, thixotropic agents, adhesives, surfactants, and the like.

The reacting layers can be formed into a multilayer structure by any appropriate method that at least in part can be determined by the chemical nature of the reactants in a particular layer. In certain embodiments, metal foils or sheets of two or more reactants can be cold pressed/rolled to form a multilayer solid fuel. Multilayer solid fuels can comprise alternating or mixed layers of reactants and can be formed by vapor deposition, sputtering or electrodeposition methods. Using wet coating methods, multiple layers of dispersions comprising the reactants can be deposited to form a multilayer solid fuel, wherein each layer can comprise the same or different composition.

The number of layers and the thickness of each layer of reactants can be selected to establish the thermal and temporal characteristics of the exothermic reaction. Depending in part on the method used to form the multilayer solid fuel, the thickness of a layer can range from, for example, 0.1 µm to 200 µm for a metal sheet, and can range from, for example, 1 nm to 100 µm for a vapor- or electro-deposited layer. The reactant layers can comprise elemental metals, alloys and/or metal oxides. Examples of layer pairs can include, but are not limited to Al:Ni, Al:Cu, Ti:Ni, Ti:C, Zr:B, Mo:Si, Ti:Si, and Zr:S. These and other combinations of reactants and/or additive materials can be used to control the burning characteristics of the solid fuel.

In certain embodiments, the multilayer structure can be repeatedly mechanically deformed to intermix the reactant layers. In certain embodiments, such as where layers are deposited by, for example, vapor deposition, sputtering or electrodeposition methods, the reactants can be deposited to form an intermixed or heterogeneous composition.

In addition to the layers comprising reactants, a multilayer solid fuel structure can comprise layers of non-reacting materials or materials having certain reaction properties to facilitate control of the thermal and temporal characteristics of the exothermic reaction.

In certain embodiments, a solid fuel can be machined, molded, pre-formed or packed. The solid fuel can be formed as a separate element configured to be inserted into a heating unit, or the solid fuel can be applied directly to a heating unit. In certain embodiments, a solid fuel can be coated, applied, or deposited directly onto a substrate forming part of a heating unit, onto a support that can be incorporated into a heating unit, or onto a support configured to transfer the solid fuel to a substrate forming a heating unit.

Figure 1B:
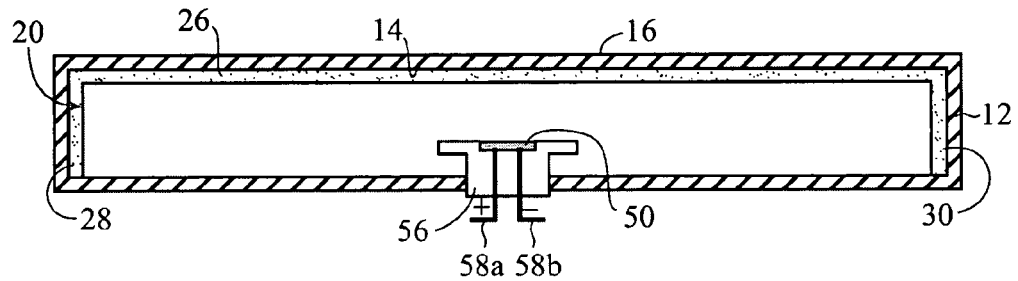
Figure 1C:
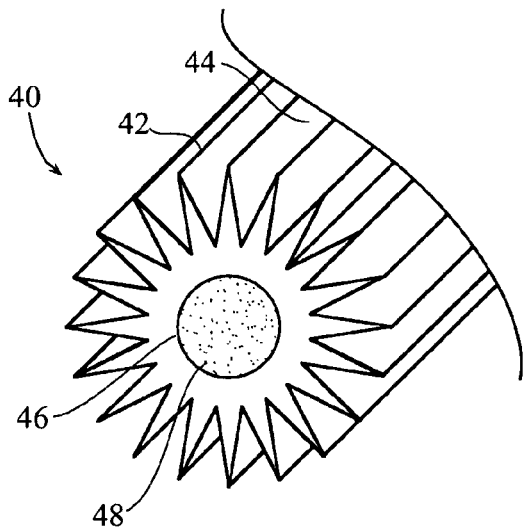
FIG. 1C is a perspective illustration of a heating unit according to certain embodiments.

The solid fuel can be any appropriate shape and have any appropriate dimensions. For example, as shown in FIG. 1A, solid fuel 20 can be shaped for insertion into a square or rectangular heating unit. As shown in FIG. 1B, solid fuel 20 can comprise a surface expanse 26 and side expanses 28, 30. FIG. 1C illustrates an embodiment of a heating unit. As shown in FIG. 1C, heating unit 40 comprises a substrate 42 having an exterior surface 44 and an interior surface 46. In certain embodiments, solid fuel 48, in the shape of a rod extending the length of substrate 42 fills the inner volume defined by interior surface 46. In certain embodiments, solid fuel 48, is in the shape of a hollow rod extending the length of substrate 42 and exhibiting a diameter less than that of interior surface 46. In certain embodiments, the inner volume defined by interior surface 46 can comprise an intervening space or a layer such that solid fuel 48 can be disposed as a cylinder adjacent interior surface 46, and/or be disposed as a rod exhibiting a diameter less than that of interior surface 46. It can be appreciated that a finned or ribbed exterior surface can provide a high surface area that can be useful to facilitate heat transfer from the solid fuel to an article or composition in contact with the surface.

In the various embodiments, fuel can be ignited to generate a self-sustaining oxidation-reduction reaction. Once a portion of the solid fuel is ignited, the heat generated by the oxidation-reduction reaction can ignite adjacent unburned fuel until all of the fuel is consumed in the process of the chemical reaction. The exothermic oxidation-reduction reaction can be initiated by the application of energy to at least a portion of the solid fuel. Energy absorbed by the solid fuel or by an element in contact with the solid fuel can be converted to heat. When the solid fuel becomes heated to a temperature above the auto-ignition temperature of the reactants, e.g. the minimum temperature required to initiate or cause self-sustaining combustion in the absence of a combustion source or flame, the oxidation-reduction reaction will initiate, igniting the solid fuel in a self-sustaining reaction until the fuel is consumed.

Energy can be applied to ignite the solid fuel using a number of methods. For example, a resistive heating element can be positioned in thermal contact with the solid fuel, which when a current is applied, can heat the solid fuel to the auto-ignition temperature. An electromagnetic radiation source can be directed at the solid fuel, which when absorbed, can heat the solid fuel to its auto-ignition temperature. An electromagnetic source can include lasers, diodes, flashlamps and microwave sources. RF or induction heating can heat the solid fuel source by applying an alternating RF field that can be absorbed by materials having high magnetic permeability, either within the solid fuel, or in thermal contact with the solid fuel. The source of energy can be focused onto the absorbing material to increase the energy density to produce a higher local temperature and thereby facilitate ignition. In certain embodiments, the solid fuel can be ignited by percussive forces.

The auto-ignition temperature of a solid fuel comprising a metal reducing agent and a metal-containing oxidizing agent as disclosed herein can range of 400° C. to 500° C. While such high auto-ignition temperatures facilitate safe processing and safe use of the solid fuel under many use conditions, for example, as a portable medical device, for the same reasons, to achieve such high temperatures, a large amount of energy must be applied to the solid fuel to initiate the self-sustaining reaction. Furthermore, the thermal mass represented by the solid fuel can require that an impractically high temperature be applied to raise the temperature of the solid fuel above the auto-ignition temperature. As heat is being applied to the solid fuel and/or a support on which the solid fuel is disposed, heat is also being conducted away. Directly heating a solid fuel can require a substantial amount of power due to the thermal mass of the solid fuel and support.

As is well known in the art, for example, in the pyrotechnic industry, sparks can be used to safely and efficiently ignite fuel compositions. Sparks refer to an electrical breakdown of a dielectric medium or the ejection of burning particles. In the first sense, an electrical breakdown can be produced, for example, between separated electrodes to which a voltage is applied. Sparks can also be produced by ionizing compounds in an intense laser radiation field. Examples of burning particles include those produced by friction and break sparks produced by intermittent electrical current. Sparks of sufficient energy incident on a solid fuel can initiate the self-sustaining oxidation-reduction reaction.

When sufficiently heated, the exothermic oxidation-reduction reaction of the solid fuel can produce sparks, as well as radiation energy. Thus, in certain embodiments, reliable, reproducible and controlled ignition of the solid fuel can be facilitated by the use of an initiator composition capable of reacting in an exothermic oxidation-reduction reaction. The initiator composition can comprise the same or similar reactants as those comprising the solid fuel. In certain embodiments, the initiator composition can be formulated to maximize the production of sparks having sufficient energy to ignite a solid fuel. Sparks ejected from an initiator composition can impinge upon the surface of the solid fuel, causing the solid fuel to ignite in a self-sustaining exothermic oxidation-reduction reaction. The igniter can comprise a physically small, thermally isolated heating element on which is applied a small amount of an initiator composition capable of producing sparks or the initiator composition can be placed directly on the fuel itself and ignited by a variety of means, including, for example, optical or percussive.

As shown in FIG. 1A, heating unit 10 can include an initiator composition 50 which can ignite a portion of solid fuel 20. In certain embodiments, as shown in FIG. 1A & 1B, initiator composition 50 can be positioned proximate to the center region 54 of solid fuel 20. Initiator composition 50 can be positioned at other regions of solid fuel 20, such as toward the edges. In certain embodiments, a heating unit can comprise more than one initiator composition where the more than one initiator composition 50 can be positioned on the same or different side of solid fuel 20. In certain embodiments, initiator composition 50 can be mounted in a retaining member 56 that is integrally formed with substrate 12 and/or secured within a suitably sized opening in substrate 12. Retaining member 56 and substrate 12 can be sealed to prevent release outside heating unit 10 of reactants and reaction products produced during ignition and burning of solid fuel 20. In certain embodiments, electrical leads 58a, 58b in electrical contact with initiator composition 50 can extend from retaining member 56 for electrical connection to a mechanism configured to activate (not shown) initiator composition 50.

Initiator compositions capable of producing sparks upon exposure to heat, force, or a spark are known, for example, in the pyrotechnic field and the photoflash industry. In certain embodiments, an initiator composition can comprise at least one metal, such as those described herein, and at least one oxidizing agent, such as, for example, a chlorate or perchlorate of an alkali metal or an alkaline earth metal or metal oxide and others disclosed herein. In certain embodiments, an initiator composition can include at least one binder and/or additive material such as a gelling agent and/or binder. Examples of additive materials including gelling agents and/or binders are disclosed herein. In certain embodiments, additive materials can be useful in determining certain processing, ignition, and/or burn characteristics of the initiator composition.

Figure 2A:
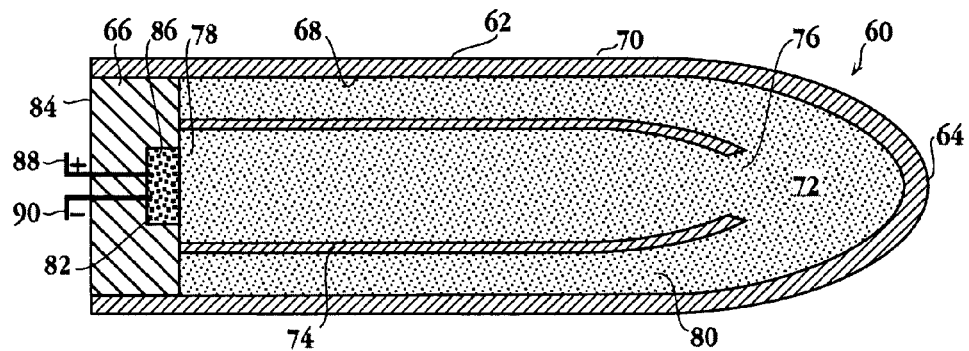
FIG. 2A is a cross-sectional illustration of a heating unit having a cylindrical geometry according to certain embodiments.

FIG. 2A shows a longitudinal cross-sectional illustration of an embodiment of a heating unit. FIG. 2B shows a corresponding perspective illustration of an embodiment illustrating the unassembled individual components shown in FIG. 2A. As shown in FIG. 2A, heating unit 60 can include a substrate 62 that is generally cylindrical in shape and terminates at one end in a tapered nose portion 64 and at the other end in an open receptacle 66. Substrate 62 has interior and exterior surfaces 68, 70, respectively, which define an inner region 72. An inner backing member 74 can be cylindrical in shape and can be located within inner region 72. The opposing ends 76, 78 of backing member 74 can be open. In certain embodiments, backing member 74 can comprise a heat-conducting or heat-absorbing material, depending on the desired thermal and temporal dynamics of the heating unit. When constructed of a heat-absorbing material, backing member 74 can reduce the maximum temperature reached by substrate 62 after ignition of the solid fuel 80.

In certain embodiments, solid fuel 80 comprising, for example, any of the solid fuels described herein, can be confined between substrate 62 and backing member 74 or can fill inner region 72. Solid fuel 80 can adjoin interior surface 68 of substrate 62.

In certain embodiments, initiator composition 82 can be positioned in open receptacle 66 of substrate 62, and can be configured to ignite solid fuel 80. In certain embodiments, a retaining member 84 can be located in open receptacle 66 and can be secured in place using any suitable mechanism, such as for example, bonding or welding. Retaining member 84 and substrate 62 can be sealed to prevent release of the reactants or reaction products produced during ignition and burn of initiator composition 82 and solid fuel 80. Retaining member 84 can include a recess 86 in the surface facing inner region 72. Recess 86 can retain initiator composition 82. In certain embodiments, an electrical stimulus can be applied directly to initiator composition 82 via leads 88, 90 connected to the positive and negative termini of a power source, such as a battery (not shown). Leads 88, 90 can be connected to an electrically resistive heating element placed in physical contact with the initiator composition 82 (not shown). In certain embodiments, leads 88, 90 can be coated with the initiator composition 82.

Referring to FIG. 2A, application of a stimulus to initiator composition 82 can result in the generation of sparks that can be directed from open end 78 of backing member 74 toward end 76. Sparks directed toward end 76 can contact solid fuel 80, causing solid fuel 80 to ignite. Ignition of solid fuel 80 can produce a self-propagating wave of ignited solid fuel 80, the wave traveling from open end 78 toward nose portion 64 and back toward retaining member 84 held within receptacle end 66 of substrate 62. The self-propagating wave of ignited solid fuel 80 can generate heat that can be conducted from interior surface 68 to exterior surface 70 of substrate 62.

Figure 2C:
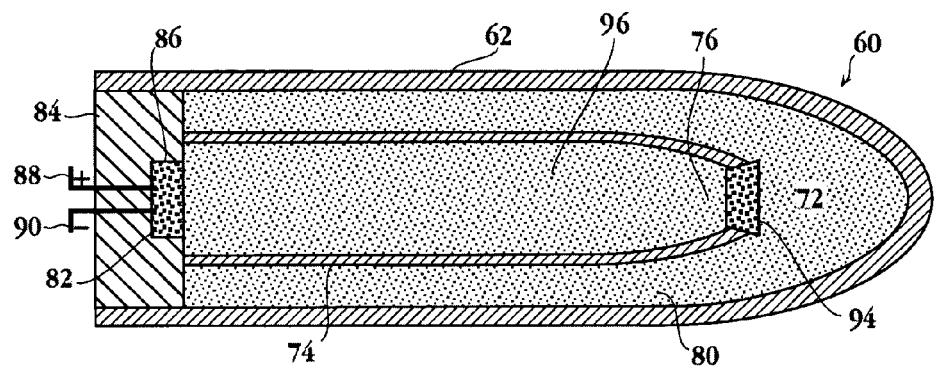
FIG. 2C is a cross-sectional illustration of a cylindrical heating unit similar to the heating unit of FIGS. 2A-2B but having a modified igniter design according to certain embodiments.

An embodiment of a heating unit is illustrated in FIG. 2C. As shown in FIG. 2C, heating unit 60 can comprise a first initiator composition 82 disposed in recess 86 in retaining member 84 and a second initiator composition 94 disposed in open end 76 of backing member 74. Backing member 74, located within inner region 72, defines an open region 96. Solid fuel 80 is disposed within the inner region between substrate 62 and backing member 74. In certain embodiments, sparks generated upon application of an electrical stimulus to first initiator composition 82, through leads 88, 90, can be directed through open region 96 toward second initiator composition 94, causing second initiator composition 94 to ignite and generate sparks. Sparks generated by second initiator composition 94 can then ignite solid fuel 80, with ignition initially occurring toward the nose portion of substrate 62 and traveling in a self-propagating wave of ignition to the opposing end.

In certain embodiments, the igniter can comprise a support and an initiator composition disposed on the support. In certain embodiments, the support can be thermally isolated to minimize the potential for heat loss. In this way, dissipation of energy applied to the combination of assembly and support can be minimized, thereby reducing the power requirements of the energy source, and facilitating the use of physically smaller and less expensive heat sources. In certain applications, for example, with battery powered portable medical devices, such considerations can be particularly useful. In certain embodiments, it can be useful that the energy source be a small low cost battery, such as a 1.5 V alkaline battery. In certain embodiments, the initiator composition can comprise a metal reducing agent and metal-containing oxidizing agent.

In certain embodiments, a metal reducing agent can include, but is not limited to molybdenum, magnesium, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, and silicon. In certain embodiments, a metal reducing agent can include aluminum, zirconium, and titanium. In certain embodiments, a metal reducing agent can comprise more than one metal reducing agent. In certain embodiments, an oxidizing agent can comprise oxygen, an oxygen based gas, and/or a solid oxidizing agent. In certain embodiments, an oxidizing agent can comprise a metal-containing oxidizing agent. In certain embodiments, a metal-containing oxidizing agent includes, but is not limited to, perchlorates and transition metal oxides. Perchlorates can include perchlorates of alkali metals or alkaline earth metals, such as but not limited to, potassium perchlorate ($KClO_4$), potassium chlorate ($KClO_3$), lithium perchlorate ($LiClO_4$), sodium perchlorate ($NaClO_4$), and magnesium perchlorate [$Mg(ClO_4)_2$]. In certain embodiments, transition metal oxides that function as oxidizing agents include, but are not limited to, oxides of molybdenum, such as $MoO_3$, iron, such as $Fe_2O_3$, vanadium ($V_2O_5$), chromium ($CrO_3$, $Cr_2O_3$), manganese ($MnO_2$), cobalt ($Co_3O_4$), silver ($Ag_2O$), copper ($CuO$), tungsten ($WO_3$), magnesium ($MgO$), and niobium ($Nb_2O_5$). In certain embodiments, the metal-containing oxidizing agent can include more than one metal-containing oxidizing agent.

The ratio of metal reducing agent to metal-containing oxidizing agent can be selected to determine the appropriate burn and spark generating characteristics. In certain embodiments, the amount of oxidizing agent in the initiator composition can be related to the molar amount of the oxidizers at or near the eutectic point for the fuel composition. In certain embodiments, the oxidizing agent can be the major component and in others the metal reducing agent can be the major component. Those of skill in the art are able to determine the appropriate amount of each component based on the stoichiometry of the chemical reaction and/or by routine experimentation. Also as known in the art, the particle size of the metal and the metal-containing oxidizer can be varied to determine the burn rate, with smaller particle sizes selected for a faster burn (see, for example, PCT WO 2004/01396).

In certain embodiments, an initiator composition can comprise additive materials to facilitate, for example, processing, enhance the mechanical integrity and/or determine the burn and spark generating characteristics. The additive materials can be inorganic materials and can function as binders, adhesives, gelling agents, thixotropic, and/or surfactants. Examples of gelling agents include, but are not limited to, clays such as LAPONITE®, Montmorillonite, CLOISITE®, metal alkoxides such as those represented by the formula R—Si(OR)$_n$ and M(OR)$_n$ where n can be 3 or 4, and M can be Ti, Zr, Al, B or other metals, and colloidal particles based on transition metal hydroxides or oxides. Examples of binding agents include, but are not limited to, soluble silicates such as Na- or K-silicates, aluminum silicates, metal alkoxides, inorganic polyanions, inorganic polycations, inorganic sol-gel materials such as alumina or silica-based sols. Other useful additive materials include glass beads, diatomaceous earth, nitrocellulose, polyvinylalcohol, guor gum, ethyl cellulose, cellulose acetate, polyvinyl-pyrrolidone, fluoro-carbon rubber (VITON®) and other polymers that can function as a binder. In certain embodiments, the initiator composition can comprise more than one additive material. The components of the initiator composition comprising the metal, metal-containing oxidizing agent and/or additive material and/or any appropriate aqueous- or organic-soluble binder, can be mixed by any appropriate physical or mechanical method to achieve a useful level of dispersion and/or homogeneity. In certain embodiments, additive materials can be useful in determining certain processing, ignition, and/or burn characteristics of the initiator composition. In certain embodiments, the particle size of the components of the initiator can be selected to tailor the ignition and burn rate characteristics as is known in the art (see for example U.S. Pat. No. 5,739,460 the disclosure of which is hereby incorporated by reference in its entirety).

In certain embodiments, an initiator composition can comprise at least one metal, such as those described herein, and at least one oxidizing agent, such as, for example, a chlorate or perchlorate of an alkali metal or an alkaline earth metal or metal oxide and others disclosed herein.

Examples of initiator compositions include compositions comprising 10% Zr:22.5% B:67.5% $KClO_3$; 49.)% Zr:49.0% $MoO_3$ and 2.0% nitrocellulose, and 33.9% Al:55.4% $MoO_3$: 8.9% B:1.8 nitrocellulose; 26.5% Al:51.5% $MoO_3$:7.8% B:14.2% VITON®, in weight percent.

Other initiator compositions can be used. For example, an initiator composition that can ignite upon application of a percussive force comprises a mixture of sodium chlorate (Na-$ClO_3$), phosphorous (P), and magnesium oxide (MgO).

Energy sufficient to heat the initiator composition to the auto-ignition temperature can be applied to the initiator composition and/or the support on which the initiator composition is disposed. The energy source can be any of those disclosed herein, such as resistive heating, radiation heating, inductive heating, optical heating, and percussive heating. In embodiments wherein the initiator composition is capable of absorbing the incident energy, the support can comprise a thermally insulating material. In certain embodiments, the incident energy can be applied to a thermally conductive support that can heat the initiator composition above the auto-ignition temperature by thermal conduction.

In certain embodiments, the energy source can be an electrically resistive heating element. The electrically resistive heating element can comprise any material that can maintain integrity at the auto-ignition temperature of the initiator composition. In certain embodiments, the heating element can comprise an elemental metal such as tungsten, an alloy such as Nichrome, or other material such as carbon. Materials suitable for resistive heating elements are known in the art. The resistive heating element can have any appropriate form. For example, the resistive heating element can be in the form of a wire, filament, ribbon or foil. In certain embodiments, the electrical resistance of the heating unit can range from 2 Ω to 4 Ω. The appropriate resistivity of the heating element can at least in part be determined by the current of the power source, the desired auto ignition temperature, or the desired ignition time. In certain embodiments, the auto-ignition temperature of the initiator composition can range from 200° C. to 500° C. The resistive heating element can be electrically connected, and suspended between two electrodes electrically connected to a power source.

The support can comprise one or more heating units.

Figure 16:
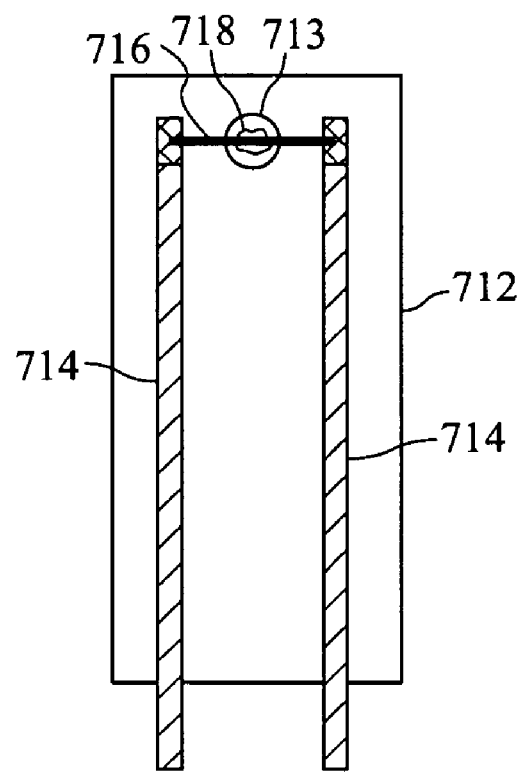
FIG. 16 is a schematic illustration of an igniter comprising an initiator composition disposed on an electrically resistive heating element.

An embodiment of an igniter comprising a resistive heating element is illustrated in FIG. 16. As shown in FIG. 16, resistive heating element 716 is electrically connected to electrodes 714. Electrodes 714 can be electrically connected to an external power source such as a battery (not shown). As shown in FIG. 16, electrodes 714 are disposed on a laminate material 712 such as a printed circuit material. Such materials and methods of fabricating such flexible or rigid laminated circuits are well known in the art. In certain embodiments, laminate material 712 can comprise a material that will not degrade at the temperatures reached by resistive heating element 716, by the exothermic reaction including sparks generated by initiator composition 718, and at the temperature reached during burning of the solid fuel. For example, laminate 712 can comprise Kapton®, a fluorocarbon laminate material or FR4 epoxy/fiberglass printed circuit board. Resistive heating element 716 is positioned in an opening 713 in laminate 712. Opening 713 thermally isolates resistive heating element 716 to minimize thermal dissipation and facilitate transfer of the heat generated by the resistive heating element to the initiator composition, and can provide a path for sparks ejected from initiator composition 718 to impinge upon a solid fuel (not shown).

As shown in FIG. 16, initiator composition 718 is disposed on resistive heating element 716.

The following procedure was used to apply the initiator composition to resistive heating elements.

A 0.0008 inch diameter Nichrome wire was soldered to Cu conductors disposed on a 0.005 inch thick FR4 epoxy/fiberglass printed circuit board (Onanon). The dimensions of the igniter printed circuit board were 1.82 inches by 0.25 inches. Conductor leads can extend from the printed circuit board for connection to a power source. In certain embodiments, the electrical leads can be connected to an electrical connector.

The igniter printed circuit board was cleaned by sonicating (Branson 8510R-MT) in DI water for 10 minutes, dried, sprayed with acetone and air dried.

The initiator composition comprised 0.68 grams nano-aluminum (40-70 nm diameter; Argonide Nanomaterial Technologies, Sanford, Fla.), 1.23 grams of nano-$MoO_3$ (EM-NTO-U2; Climax Molybdenum, Henderson, Co.), and 0.2 grams of nano-boron (33,2445-25G; Aldrich). A slurry comprising the initiator composition was prepared by adding 8.6 mL of 4.25% VITON® A500 (4.25 grams VITON® in 100 mL amyl acetate (Mallinckrodt)) solution.

A 1.1 uL drop of slurry was deposited on the heating element, dried for 20 minutes, and another 0.8 uL drop of slurry comprising the initiator composition was deposited on the opposite side of the heating element.

Application of 3.0 V through a 1,000 µF capacitor from two A76 alkaline batteries to the Nichrome heating element ignited the $Al:MoO_3:B$ initiator composition within 1 to 50 msec, typically within 1 to 6 msec. When positioned within 0.12" inches of the surface of a solid fuel comprising a metal reducing agent and a metal-containing oxidizing agent such as, for example, a fuel comprising 76.16% $Zr$:19.04% $MoO_3$: 4.8% LAPONITE® RDS, the sparks produced by the initiator composition ignited the solid fuel to produce a self-sustaining exothermic reaction. In certain embodiments, a 1 µL drop of the slurry comprising the initiator composition can be deposited onto the surface of the solid fuel adjacent the initiator composition disposed on the resistive heating element to facilitate ignition of the solid fuel.

The initiator composition comprising $Al:MoO_3:B$ adhered to the Nichrome wire and maintained physical integrity following mechanical and environmental testing including temperature cycling (−25° C.⇔40° C.), drop testing, and impact testing.

Figure 2D:
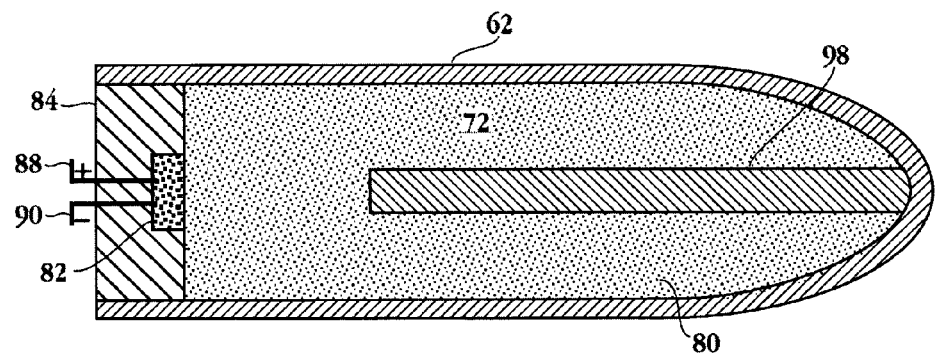
FIG. 2D is a cross-sectional illustration of a cylindrically-shaped heating unit that includes a thermal shunt according to certain embodiments.
Figure 2B:
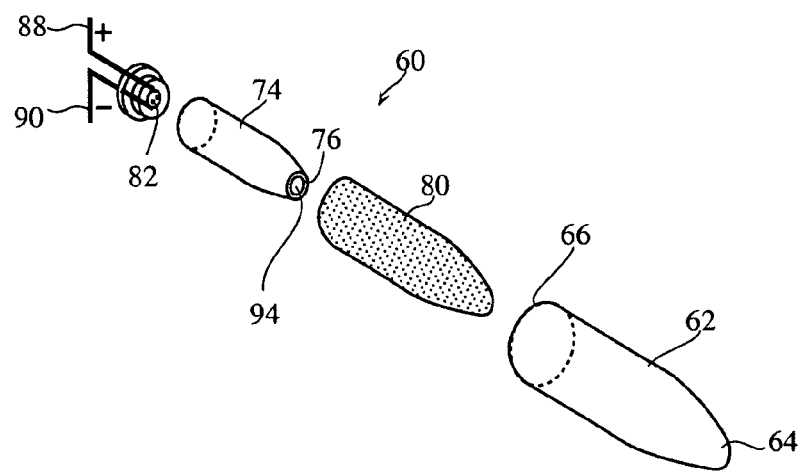
FIG. 2B is a perspective illustration of a heating unit having a cylindrical geometry according to certain embodiments.
Figure 3:
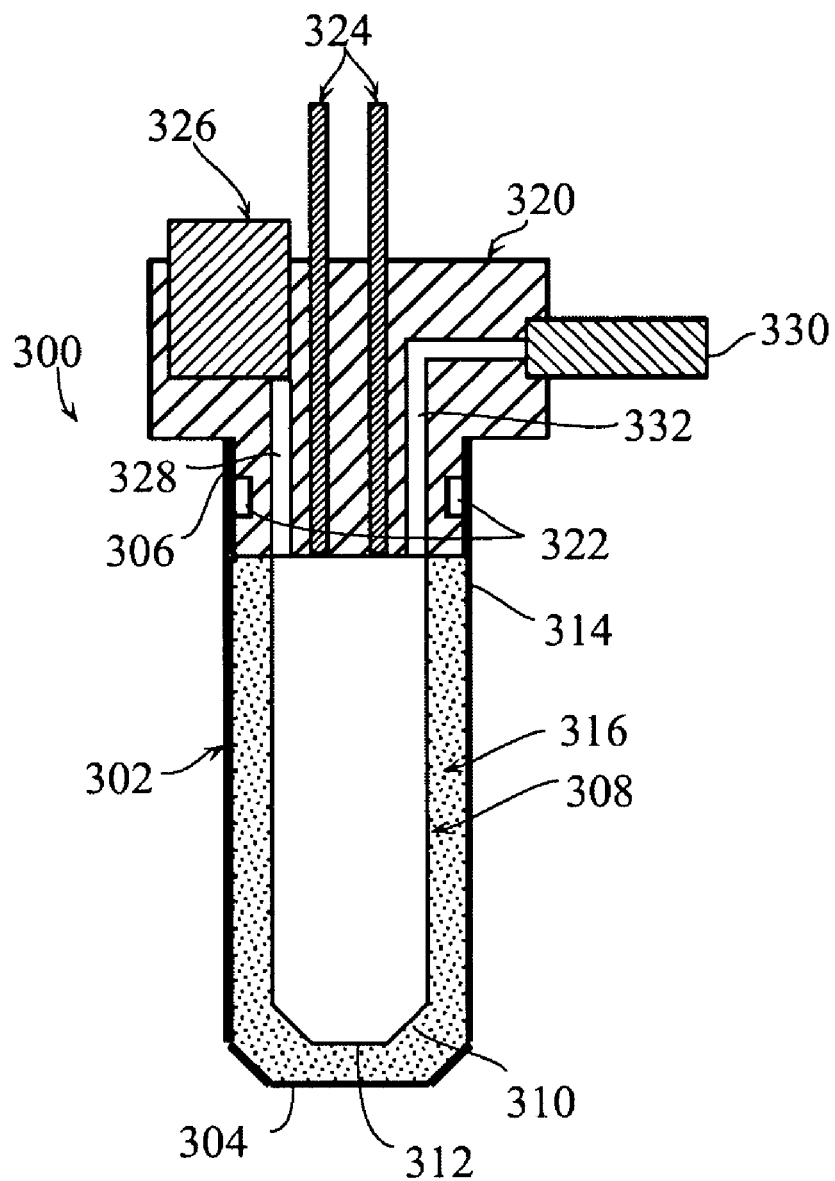
FIG. 3 is a schematic cross-sectional illustration of a chemical heating unit having two pressure transducers for measuring the internal pressure during and after ignition of the solid fuel according to certain embodiments.

In certain embodiments, as shown in FIG. 2D heating units can include a thermal shunt 98, shown in FIG. 2D as a cylindrical rod disposed within the heating unit. In certain embodiments, the thermal shunt can be incorporated into the solid fuel expanse as a particulate, the thermal shunt can comprise the backing member and/or the thermal shunt can be a separate element as shown. The thermal shunt can be in direct contact with the solid fuel and/or can indirectly contact the solid fuel. In certain embodiments, a thermal shunt can be capable of absorbing heat such that incorporation of a thermal shunt in a heating unit can control or reduce the maximum temperature reached by the exterior surface of the substrate forming the heating unit. For example, in certain embodiments, the thermal shunt can comprise a material capable of undergoing a phase change at or above the ignition temperature of the solid fuel. Examples of phase change materials include low melting point metals such as tin, low melting point alloys such as Wood's metal and lead-tin alloys, inorganic salts, and mixtures thereof. In certain embodiments, the thermal shunt can comprise a material that can release absorbed heat to prolong the heating time of the heating unit. In certain embodiments, a thermal shunt can comprise at least one material exhibiting a high heat capacity, such as, for example, copper, aluminum, stainless steel and glass. Examples of materials that can release absorbed heat include sugars, waxes, metal salts and other materials capable of melting during burning of the solid fuel and then undergoing crystallization as the heating unit cools, thus generating exothermic heat of crystallization, and mixtures thereof. Other materials capable of functioning as thermal shunts include porous and fibrous materials such as porous ceramic membranes and/or fiber mats, and the like. Such materials can exhibit a high surface area that can facilitate heat transfer from the reactants and reaction products to the material matrix. In certain embodiments, the porous and/or fibrous materials do not react with the reactants or reaction products produced during ignition and burn, and do not degrade and/or produce gaseous products at the temperatures achieved by the heating unit. In certain embodiments, the thermal shunt material can comprise fibers including, but not limited to, metal fibers, silica fibers, glass fibers, graphite fibers, and/or polymer fibers.

In certain embodiments, the heating units described and illustrated in FIGS. 1A-1C and 2A-2D can be used in applications wherein rapid heating is useful. In certain embodiments, a portion of the substrate can reach a maximum (peak) temperature in less than three seconds (3 sec), in certain embodiments less than 1 second (1 sec), in certain embodiments less than 500 milliseconds, and in certain embodiments less than 250 milliseconds.

A heating unit substantially as illustrated in FIG. 2B was fabricated to measure the temperature of the exterior surface of the substrate following ignition of a solid fuel. Referring to FIG. 2B, cylindrical substrate 62 was approximately 1.5 inches in length and the diameter of open receptacle 66 was 0.6 inches. Solid fuel 80 comprising 75% Zr:25% $MoO_3$ in weight percent was placed in the inner region in the space between the backing member 74 and the interior surface of substrate 62. A first initiator composition 82 comprising 5 mg of 10% Zr:22.5% B:67.5% $KClO_3$ in weight percent was placed in the depression of the retaining member and 10 mg of a second initiator composition 94 of 10% Zr:22.5% B:67.5% $KClO_3$ in weight percent was placed in the open end 76 of backing member 74 near the tapered portion of heating unit 60. Electrical leads 88, 90 from two 1.5 V batteries provided a current of 0.3 Amps to ignite first initiator composition 82, thus producing sparks to ignite second initiator composition 94. Both initiators were ignited within 1 to 20 milliseconds following application of the electrical current. Sparks produced by second initiator composition 94 ignited solid fuel 80 in the tapered nose region 64 of the cylinder. Thermocouples placed on the exterior surface of substrate 62 were used to monitor the substrate surface temperature as a function of time. The exterior substrate surface reached a maximum temperature of 400° C. in less than 100 milliseconds.

Upon ignition of the solid fuel, an exothermic oxidation-reduction reaction produces a considerable amount of energy in a short time, such as for example, in certain embodiments less than 1 second, in certain embodiments less than 500 milliseconds, and in certain embodiments less than 250 milliseconds. Examples of exothermic reactions include electrochemical reactions and metal oxidation-reduction reactions. When used in enclosed heating units, by minimizing the quantity of reactants and the reaction conditions the reaction can be controlled but can result in a slow release of heat and/or a modest temperature rise. However, in certain applications, it can be useful to rapidly heat a substrate to temperatures in excess of 200° C. within 1 second or less. Such rapid intense thermal pulses can be useful for vaporizing pharmaceutical compositions to produce aerosols. A rapid intense thermal pulse can be produced using an exothermic oxidation-reduction reaction and in particular a thermite reaction involving a metal and a metal-containing oxidizing agent. Concomitant with the rapid generation of heat, there can be a rapid generation of gaseous products and unreacted reactants with high translational energies. When sealed within an enclosure, the exothermic oxidation-reduction reaction can generate a significant increase in pressure.

Energy produced by the exothermic reaction, whether thermal, optical, mechanical, e.g. particle ejection, or chemical can generate a significant pressure when contained with a sealed enclosure. In certain embodiments, a solid fuel capable of reacting in an exothermic oxidation-reduction reaction can be used to form a heating unit. For example, solid fuel as disclosed herein can be used to thermally vaporize a drug coating to produce an aerosol of a drug for medical applications. In certain applications, such as in portable medical devices, it can be useful to contain the pyrothermic materials and products of the exothermic reaction and other chemical reactions resulting from the high temperatures within the enclosure. While containing the exothermic reaction can be accomplished by adequately sealing the enclosure to withstand the internal pressures resulting from the burning of the solid fuel as well as an initiator composition if present, it can be useful to minimize the internal pressure to ensure the safety of the heating device and facilitate device fabrication.

In certain embodiments, the pressure within the substrate can increase during and after ignition and burning of the initiator composition and the solid fuel. The increase in pressure can depend, at least in part, on the amount and composition of the solid fuel, the relative amounts of the fuel components, the density and/or degree of compaction of the solid fuel, the particle size of the fuel components, the configuration of the substrate, the amount of initiator, and/or the composition of the initiator. In certain embodiments, a solid fuel, an initiator composition, and a substrate configuration can be selected to control the pressure increase and maintain the maximum pressure within a useful operating range. The initiator composition and solid fuel can produce gas phase reaction products during ignition and bum. Thus, in certain embodiments, the pressure within the substrate can be managed by minimizing the amount of initiator composition and solid fuel disposed within the heating unit. One of skill can experimentally determine the minimum amount of initiator composition needed to reliably ignite the solid fuel. One of skill can also determine the properties, configuration, and placement of the solid fuel within a heating unit to achieve a useful substrate temperature.

In certain embodiments, the internal pressure of a heating unit can be managed or reduced by constructing the substrate, backing, and any other internal components from materials that produce minimal gas products at elevated temperatures. In certain embodiments, pressure can be managed or reduced by providing an interior volume wherein gas can be collected and/or vented when the initiator and solid fuel are burned. In certain embodiments, the interior volume can include a porous or fibrous material having a high surface area and a large interstitial volume. The interstitial volume can contain a gas generated as a result of the initiator and solid fuel reactions and can thereby reduce the pressure within the enclosure and collisions of the reactants and reaction products with the matrix of the porous or fibrous material can efficiently transfer the internal and translational energy.

The internal pressure of a heating unit during and after burning of an initiator composition and a solid fuel can vary depending on the parameters discussed above. The internal pressure of certain embodiments of heating units was measured using the fixture illustrated in FIG. 3. As shown in FIG. 3, heating unit 300 comprises a substantially-cylindrically shaped substrate 302 having a closed nose portion 304 and an open receiving end 306. A backing member 308 is disposed within the interior region of substrate 302. Backing member 308 is cylindrical in shape but of overall smaller dimensions than that of substrate 302. Tapered nose portion 310 defines an opening 312 in backing member 308. Opposing end 314 from tapered nose portion 310 of backing member 308 is open. The interior surface of substrate 302 and the exterior surface of backing member 308 define an annular shell or a gap into which a solid fuel 316 can be disposed. A plug 320 is sized for insertion into open receiving end 306 of substrate 302 and is securely sealed by an O-ring 322. Electrodes 324 in contact with an initiator composition (not shown) disposed within heating unit 300 extend through plug 320 for electrical connection to a power source (not shown) external to heating unit 300. Pressure transducer 326 for measuring the steady state pressure via line 328 within heating unit 300 can be mounted on plug 320. A dynamic pressure transducer 330 can be provided for monitoring the pressure within heating unit 300 via line 332.

A heating unit equipped with two pressure transducers, as illustrated in FIG. 3, was used to simultaneously measure the dynamic pressure and steady state pressure within a heating unit of a type as shown in FIG. 2. For dynamic pressure measurement, a high frequency shock wave/blast ICP pressure sensor (PCB, model 113A24, maximum pressure=1,000 psig) combined with a line powered ICP signal conditioner (PCB, model 484B06) was used. For steady state pressure measurement, a subminiature millivolt output type pressure transducer (Omega Engineering, model PX600-500GV, maximum pressure=500 psig) and a high performance strain gauge indicator with analog output (PCB, DP41-S-A) were used. Signals generated by the pressure transducers were recorded and stored using two oscilloscopes. To minimize the influence of pressure measurement on the performance of the heating unit, the volume of lines 328 and 332 were designed so as not to exceed 2% of the total unfilled internal volume of the heating unit. The measured internal pressure ranged from 100 psig to 300 psig, and depended primarily on the composition of the solid fuel. The contribution of the initiator composition to the internal pressure was a maximum 100 psig.

Figure 17:
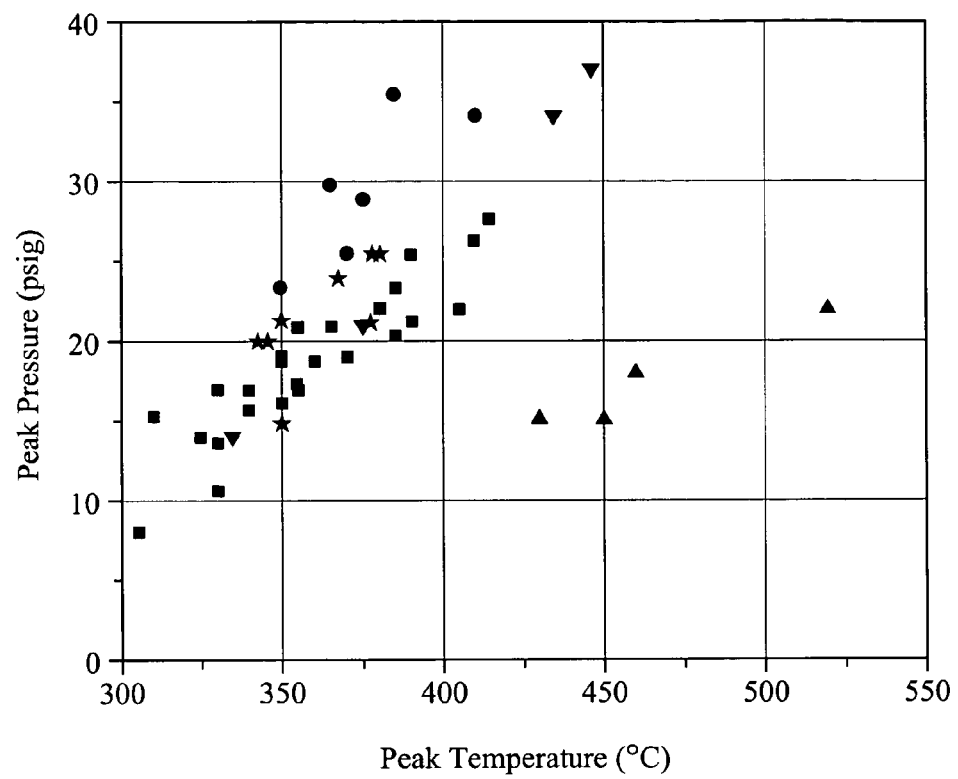
FIG. 17 shows peak internal pressure within sealed heating units following ignition of a thin film layer of solid fuel comprising a metal reducing agent and a metal-containing oxidizer.

Measurements of the peak internal pressure within sealed heating units, of a type as shown in FIG. 10, following ignition of a thin film layer of solid fuel comprising a metal reducing agent and a metal-containing oxidizer are shown in FIG. 17. The experimental arrangement used to generate the results shown in FIG. 17 is described in Example 2. FIG. 17 shows that for certain embodiments, the peak pressure within a heating unit can range from 10 psig to 40 psig and correlates with the peak temperature of the exterior surface of the substrate. Also, as shown in FIG. 17, the peak pressure within the heating unit, as well as the peak temperature of the substrate surface can for the particular embodiments of heating units measure, depend on the composition of the solid fuel, and the thickness of the foil substrate.

The internal pressure within a heating unit can also be managed or reduced by incorporating materials capable of absorbing, adsorbing or reacting with gas phase reaction products. The surface of the material may intrinsically be capable of absorbing, adsorbing or reacting with the gaseous products, or can be coated or decorated with, for example, elements, compounds and/or compositions. In certain embodiments, the immediate burst of pressure resulting from the solid fuel burn can be reduced by locating an impulse absorbing material and/or coating within the heating unit. An embodiment of a heating unit comprising an impulse absorbing material is schematically illustrated in FIG. 13.

Figure 13A:
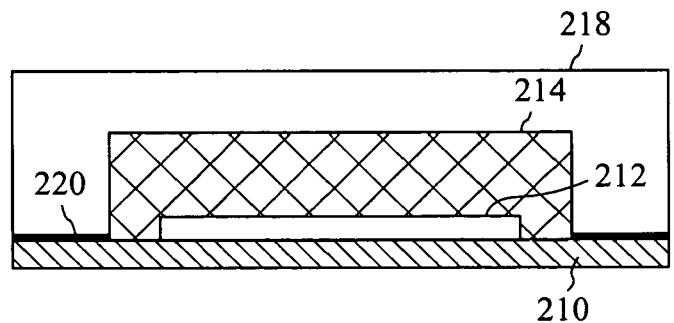
FIG. 13A is an illustration of a cross-sectional view of a heating unit having an impulse absorbing material disposed within the unit.
Figure 13B:
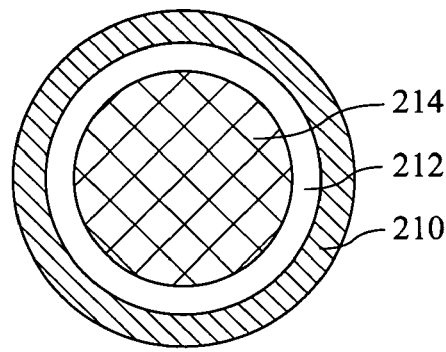
FIG. 13B is an illustration of a cross-sectional view of a cylindrical heating unit having an impulse absorbing material disposed within the unit.
Figure 13C:
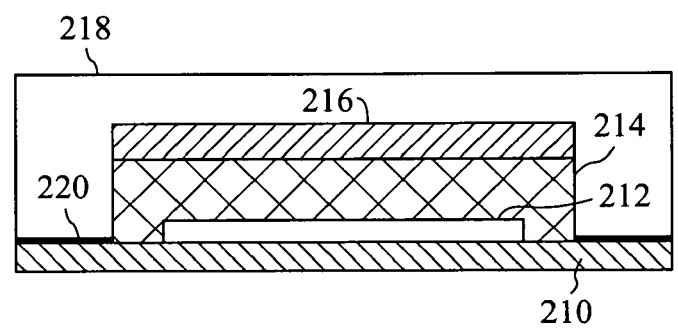
FIG. 13C is an illustration of a cross-sectional view of a heating unit having an impulse absorbing material and an additional pressure reducing element disposed with the enclosure.

FIGS. 13A-C show a thermally conductive substrate 210, such as metal foil on which is disposed a coating of a solid fuel 212. Solid fuel 212 can comprise a metal reducing agent and a metal-containing oxidizing agent capable of forming an oxidation-reduction reaction, such as, but not limited to, any of those disclosed herein. In FIGS. 13A-C thermally conductive substrate 210 is sealed using a sealant 220 to an enclosure 218 to form the heating unit. Sealant 220 can be an adhesive or any other methods for forming a seal, such as for example, welding, soldering, fastening or crimping. An impulse absorbing material 214 is disposed between the interior surface of enclosure 218 and the interior surfaces of substrate 210 and the solid fuel 212. As shown in FIGS. 13A-C, impulse absorbing material fills the interior volume defined by the interior surfaces of the heating unit. In certain embodiments, the impulse absorbing material can fill a portion of the interior volume defined by the interior surfaces of the heating unit (not shown). The thickness of the impulse absorbing material, e.g. the dimension between the interior surface of solid fuel 212 and the interior surface of enclosure 218 can be any appropriate thickness to reduce the initial pressure impulse resulting from the burning of solid fuel 212 to an appropriate level. The appropriate thickness can vary at least in part on the amount of solid fuel, the solid fuel composition, and/or the physical characteristics of the impulse absorbing material such as porosity, density, and composition and the maximum acceptable pressure within the enclosure. It will be appreciated that above a certain thickness, additional impulse absorbing material can have limited effect on reducing the peak pressure within the heating unit. The impulse absorbing material can comprise one or more materials and one or more layers of impulse absorbing material. In certain embodiments wherein multiple layers of impulse absorbing materials are used, each layer can comprise the same or different material. In FIG. 13C, an element 216 overlays impulse absorbing material 214. Element 216 can be the same or a different impulse absorbing material, and in certain embodiments, can include a getter. FIG. 13B illustrates a cross-sectional view of a cylindrical heating unit comprising a substrate 210, a layer of solid fuel 212, and a central region filled with an impulse absorbing material 214.

In certain embodiments, the impulse absorbing material can comprise a material which can absorb the thermal and translational energy of the reactants and reaction products produced during burning of the solid fuel, and if present, an initiator composition. In certain embodiments, an initiator composition comprising, for example, any of the initiator compositions disclosed herein, can be incorporated into the sealed heating unit to initiate the self-sustaining exothermic reaction of the solid fuel. An impulse absorbing material can present a high surface area to absorb the pressure impulse of thermally and translationally hot molecules and which does not react at the temperatures reached within the heating unit during and following the burn of the solid fuel. Examples of such materials include porous materials such as ceramic membranes, and fibrous materials such as fiber mats. Hot molecules physically and/or thermally ejected from the burning solid fuel can pass through the interstitial spaces defined by porous or fibrous matrix to access a large surface area, which upon collision, can facilitate transfer of thermal and translational energy to the matrix of the impulse absorbing material, thereby reducing the peak pressure within the heating unit.

Examples of porous membranes include, but are not limited to ceramic membranes, fluorocarbon membranes, alumina membranes, polymer membranes, and membranes formed from sintered metal powders. Examples of fibrous materials include, but are not limited to, glass, silica, carbon, graphite, metals, and high temperature resistant polymers. Sponge materials can also be used. The porosity and density of the impulse absorbing material can be selected to reduce the peak pressure by an appropriate amount. For a given amount of solid fuel, composition of solid fuel, and heating unit dimensions, the appropriate porosity and density of the impulse absorbing material can be determined empirically. In certain embodiments, it can be useful to have the pores sufficiently large to facilitate entry of the thermally and translationally hot molecules to the interior of an impulse absorbing material, or to one or more additional layers of impulse absorbing materials with different porosity and/or composition to facilitate transfer of energy from the hot molecules to the impulse absorbing material.

Figure 14:
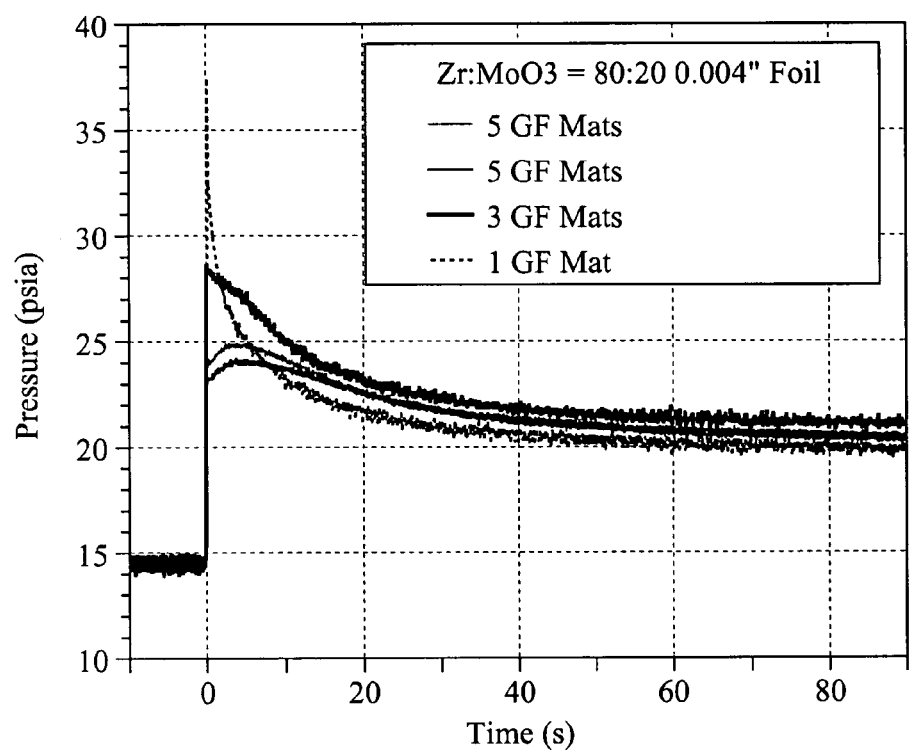
FIG. 14 shows the measured pressure within heating units comprising glass fiber mats following ignition of the solid fuel.

The effect of incorporating glass fiber mats on the internal pressure of a heating unit is shown in FIG. 14. Glass fiber mats were placed over a coating of solid fuel comprising an average mass of 177 mg of 80% Zr:20% $MoO_3$ disposed on a 0.004 inch thick stainless steel foil, and the pressure within the enclosure measured following ignition of the solid fuel. Each glass fiber mat was 0.040 inches thick. As shown in FIG.

14, glass fiber mats significantly reduced the peak internal pressure of the heating unit. When a single mat was used, the maximum pressure within the sealed enclosure was 22 psig, when two mats were used the maximum pressure was 13 psig, and when 5 mats were used, the peak pressure was 9 psig.

Figure 15:
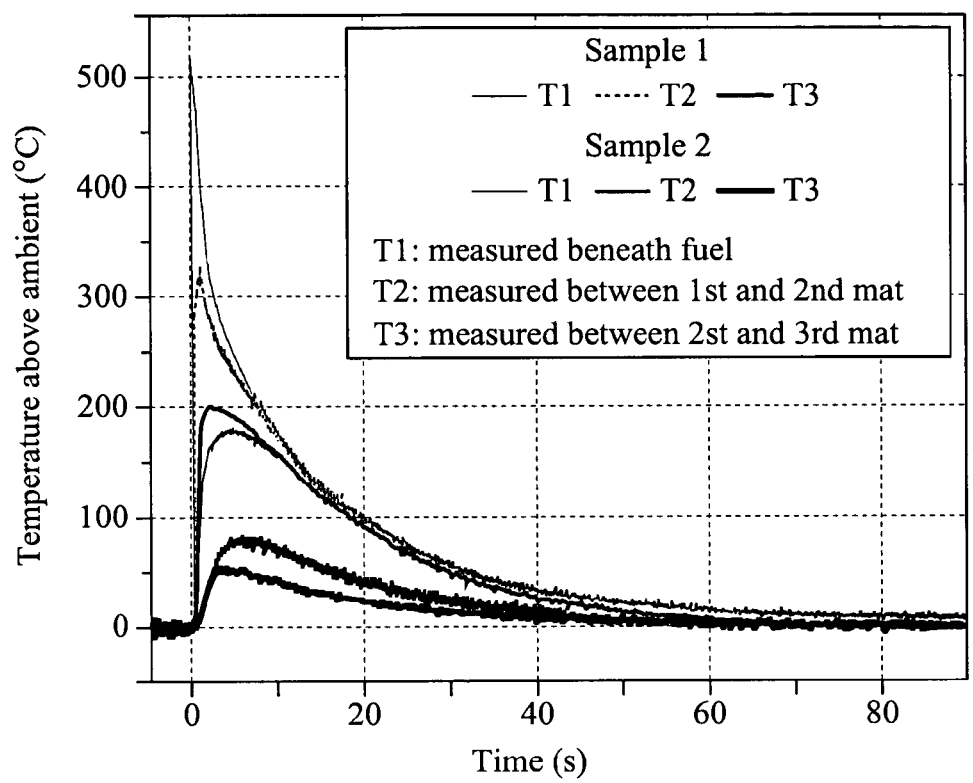
FIG. 15 shows the temperature at various positions within a heating unit following ignition of the solid fuel.

The ability of glass fiber mats to reduce the temperature within a heating unit is shown in FIG. 15. The same experimental arrangement as described for FIG. 14 was used. The peak temperature measured between the solid fuel and the first mat was about 515° C. and 325° C., between the first and second mats was about 200° C. and 180° C., and between the second and third mats was less than 100° C., thus demonstrating that the internal and translational energy of the reactants and reaction products is transferred to the impulse absorbing materials.

As demonstrated by the results shown in FIG. 14, the residual pressure, e.g. the pressure 10 seconds or more after solid fuel ignition, in the heating unit was insensitive to the presence of an impulse absorbing material. Without being limited by theory, the residual pressure can be the result of gases evolved and/or produced during the burning of the solid fuel. Possible gas sources include hydrogen bonded to the metal reducing agent, and unreacted oxygen produced during the oxidation reaction and unreacted gaseous intermediates. For example, oxygen generated by the metal-containing oxidizing agent may not immediately react with the metal reducing agent, but rather can proceed through several gaseous reaction intermediates.

In certain embodiments, the residual pressure within a heating unit can be reduced by including materials capable of gettering the residual gaseous reaction products. Such materials can be included with the impulse absorbing material, intrinsic to the impulse absorbing material, and/or applied to the impulse absorbing material as a coating, deposit, layer, and the like. In certain embodiments, the getter can be coated or deposited onto a support disposed within a heating unit and/or on one or more interior surfaces of the heating unit.

Getters are materials capable of absorbing, adsorbing and/or reacting with gases and can be used to improve and/or maintain a vacuum, and/or to purify gases. Absorption refers to the process by which one material is retained by another, such as the attachment of molecules of a gas or vapor to a solid surface by physical forces. Adsorption refers to the increase in the concentration of a dissolved substance at the interface of a condensed and a gaseous or liquid phase. Getters are used for example in the semiconductor industry to reduce residual gases in high vacuum systems. In certain embodiments, getters capable of removing hydrogen gas, $H_2$, and molecular oxygen, $O_2$, can include, but are not limited to, compositions including metals and nonmetals, such as Ta, Zr, Tb, Ti, Al, Mg, Ba, Fe, and P. Examples of getters useful for removing $H_2$ gas include, but are not limited to, sintered Zr/graphite powders, Zr/Al compositions, Zr/V/Fe, polymer-bound getters such as PdO/zeolite dispersed in a polymer matrix, and polydiene hydrogenation catalyst compositions. Iron-based and polymeric getters have been developed to absorb $O_2$. Carbon and/or graphite based materials can be used to adsorb and/or absorb $H_2$ and $O_2$. In certain embodiments, a getter can also adsorb, absorb and/or react with volatile intermediate products or the unreacted reactants of the exothermic oxidation-reduction reaction such as, for example, $MoO_x$, CO, $CO_2$, and $N_2$.

A getter can be applied to a substrate by any appropriate method. In certain embodiments, it can be useful to provide a large surface area of getter to rapidly and efficiently reduce the residual gas pressure. This can be accomplished, for example, by providing a getter formed from a porous material, such as a sintered powder, or a fibrous material. In certain embodiments, the getter can be applied to the surface of a porous or fibrous material.

Certain embodiments of heating units were used to examine the burn propagation speed of the solid fuel following ignition. The burn propagation speed refers to the speed of the burn front, which separates unburned and burned solid fuel regions. In certain embodiments, the burn propagation speed can be determined at least in part by the solid fuel composition, the particle size of the components of the solid fuel, the density or level of compaction of the solid fuel, the shape and dimensions of the solid fuel, the material forming the heating unit, and/or any internal components such as a backing member. The temporal and spatial characteristics of the burn propagation speed for cylindrically-shaped heating units were evaluated by monitoring the surface temperature of heating units using an infrared thermal imaging camera (FLIR Systems, Thermacam SC3000).

Thermal images of a cylindrically-shaped heating unit measured by infrared thermal imaging as a function of time, in milliseconds, are shown in FIGS. 4A-4F. The construction of the heating unit used to produce the thermal images is provided in Example 3. The substrate was 1.5 cm in diameter and 4.5 cm in length In FIGS. 4A-4F, two images are shown in each panel. In both images, white areas in color correspond to a surface temperature of 500° C. and black areas correspond to a surface temperature of 25° C. The top image corresponds to a front view of the heating unit and the lower image corresponds to a rear view of the heating unit, which was obtained from a reflection in a minor mounted behind the unit. FIG. 4A shows the extent of the self-propagating wave of ignited solid fuel 100 milliseconds after ignition. FIGS. 4B-4E, taken at 200, 300, 400, and 500 milliseconds after ignition, respectively, show that the wave of ignited fuel continued to propagate along the axial direction of the heating unit. The image shown in FIG. 4F was taken at 600 milliseconds after ignition, at which time the entire surface of the substrate was heated, indicating that the solid fuel was consumed. The data gathered from this and other studies using various solid fuel compositions and heating unit configurations demonstrated that the burn propagation speed can range from 1.5 cm/sec to 50 cm/sec. Thus, in certain embodiments, the speed at which heat is transferred to a substrate forming the heating unit can be tailored as useful for certain applications.

Figure 5A:
FIGS. 5A-5B are thermal images showing the temperature uniformity of the exterior substrate surface expanse 400 milliseconds after ignition of two cylindrically-shaped heating units according to certain embodiments.
Figure 5B:
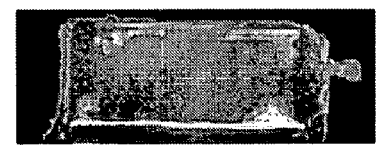

In other studies, heating units as described in Examples 4A and 4B were fabricated and the surface temperature uniformity was evaluated by infrared thermal imaging. Heating units prepared for these studies differed from those used in the investigation of burn propagation speed only in the mass ratio of metal and oxidizing agent used to form the solid fuel. Thermal images taken 400 milliseconds after igniting the solid fuel are shown in FIGS. 5A-5B. The image shown in FIG. 5A corresponds to a heating unit comprising the solid fuel composition described in Example 4A and the image in FIG. 5B to a heating unit comprising the solid fuel composition described in Example 4B. The dimensions of the heated area were 1.5 cm by 4.5 cm. The exterior substrate surface of the heating unit used to produce the image shown in FIG. 5B is more uniform than that of the heating unit shown in FIG. 5A. In certain embodiments, the substrate surface temperature can be more uniform in heating units designed for axial flame propagation. In certain embodiments, the substrate surface temperature is considered uniformly heated if no more than 10% of the exterior surface exhibits a temperature 50° C. to 100° C. less than the average temperature of the remaining 90% of the exterior surface.

In certain embodiments, it can be useful that at least a portion of the exterior surface of the substrate be heated to a uniform temperature, and that the heated portion be heated at a similar rate. Uniform heating of at least a portion of the substrate can be facilitated by reducing the thermal mass of the substrate in the region to be heated and/or by controlling the amount of solid fuel generating heat. Uniform heating of the exterior surface of the substrate can be useful for vaporizing a compound disposed on the exterior substrate surface in a short period of time to form an aerosol comprising the vaporized compound having high yield and purity. As an example, uniform heating of a 1.3 inch by 1.3 inch substrate area can be achieved by applying a 0.00163±0.000368 inch thick layer of solid fuel onto a 0.004 inch thick foil. Upon ignition, the surface of the foil opposing the surface on which 0.18 g of the solid fuel is applied can reach a maximum temperature of 440° C. over the 1.3 inch by 1.3 inch area at 250 msec after ignition. As will be appreciated by one of skill in the art, the fuel thickness selected will depend on the fuel composition, the foil thickness, and the desired temperature.

Examples 5-7 provide heating units prepared and evaluated for pressure during burn, burn propagation speed, and substrate temperature uniformity. The heating unit described in Example 5 was comprised of a solid fuel composition of Zr, $MoO_3$, $KClO_3$, nitrocellulose, and diatomaceous earth. After remote ignition of the solid fuel from the tip of the heating unit (opening 312 in FIG. 3), the internal pressure increased to 150 psig during the burn period of 0.3 seconds. One minute after burn, the residual pressure was under 60 psig. The burn propagation speed was measured by infrared thermal imaging to be 13 cm/sec. With respect to surface temperature uniformity, no obvious cold spots were observed. (A cold spot, for purposes of Examples 5-7 herein, is defined as a portion of the surface exhibiting a temperature which is 50° C. to 100° C. less than the average temperature of the remaining 90% of the exterior surface.)

The heating unit prepared as described in Example 6 contained a solid fuel composition comprised of Zr, $MoO_3$, and nitrocellulose. The gap or annular shell between the substrate and backing member was 0.020 inches. The external surface of the backing member was coated with initiator composition to increase the burn propagation speed. The solid fuel was remotely ignited from the tip of the heating unit (opening 312 in FIG. 3). The internal pressure increased to 200 psig during the reaction period of 0.25 seconds, and the residual pressure was under 60 psig. The burn propagation speed was 15 cm/sec. With respect to surface temperature uniformity, no obvious cold spots were observed.

The heating unit prepared as described in Example 7 contained a solid fuel composition of Al, $MoO_3$, and nitrocellulose. The solid fuel was placed in a 0.020-inch annular shell gap between the substrate and the backing member. The solid fuel was directly ignited near the plug. The internal pressure increased to 300 psig during the reaction period of less than 5 milliseconds. The residual pressure was under 60 psig. The exterior surface of the substrate was uniformly heated, with between 5 percent to 10 percent of the exterior surface exhibiting a temperature 50° C. to 100° C. less than that of the remaining exterior surface.

Percussion Ignition

Percussion ignition can also be used to ignite the heating unit. Percussion ignition generally comprises a deformable ignition tube within which is an anvil coated with an initiator composition. Ignition is activated by mechanical impact or force.

For the initiator composition to operate satisfactorily when actuated, the material must exhibit both the proper ignition sensitivity as well as to ignite the solid fuel properly. Various initiator compositions can be used but generally consists of a mixture of readily combustible fuel such as phosphorus with an oxidizer compound for the fuel such as alkali metal chlorates and perchlorates. The initiator composition also further generally includes a powdered combustible metal such as titanium, zirconium, hafnium, thorium, aluminum, magnesium, boron, silicon or their alloys. Typically, the initiator compositions are prepared as liquid suspension in an organic or aqueous solvent for easy handling and coating the anvil and soluble binders are generally included to provide adhesion of the coating to the anvil if required.

The initiator composition can be mixed using conventional methods to provide an even blend of the constituents. Typically, all solid materials can have a particle range from a fine mesh size to a micron size or a nanometer size. By changing the ratio of the solid materials in the initiator composition, it is possible to make the final initiator composition release more or less energy, as is needed, and to be more or less sensitive to light pulses, air or oxygen and shock.

The coating of the initiator material can be applied to the anvil in various known ways. For example, the anvil can be dipped into a slurry of the initiator composition followed by drying in air or heat to remove the liquid and produce a solid adhered coating have the desired characteristic previously described. Alternately, the slurry can be sprayed or spin coated on the anvil and thereafter processed to provide a solid coating. The thickness of the coating of the initiator composition on the anvil should be such, that when the anvil is place in the ignition tube, the initiator composition is a slight distance of around a few thousandths of an inch or so, for example, 0.004 inch, for the inside wall of the ignition tube.

The anvil on which the initiator composition is disposed is typically a metal wire or rod. It should be of a suitable metallic composition such that it exhibits a high temperature resistance and low thermal conductivity, such as, for example, stainless steel. The anvil is disposed within the metal ignition tube and extended substantially coaxially. Thus, the anvil should be of a slightly smaller diameter than the inside diameter of the ignition tube so as to be spaced a slight distance, for example, about 0.05 inch or so from the inside wall thereof.

The anvil is disposed within a metal ignition tube. The ignition tube should be of readily deformable materials and can comprise a thin-walled (for example, 0.003-inch wall thickness) tube of a suitable metallic composition, such as for example, aluminum, nickel-chromium iron alloy, brass, or steel. The anvil can be held or fastened in place in the ignition tube near its outer tube by crimping or any other method typically used.

Ignition of the fuel is actuated by a forceful mechanical impact or blow applied against the side of the metal ignition tube to deform it inwardly against the coating of the initiator material on the anvil, which causes deflagration of the initiator material up through the ignition tube into the fuel coated heating unit. Various means for providing mechanic impact can be used. In certain embodiments a spring loaded impinger or striker is used to actuate the ignition.

An embodiment of a heating unit 800 comprising a percussive igniter is illustrated in FIG. 21. As shown in FIG. 21, a deformable ignition tube 805, with an initiator composition coated anvil 803 contained therein, is placed between two substrates 801 coated with solid fuel 802, with the open end of the ignition tube disposed within the heating unit 800. The heating unit 800 is then sealed An example of the preparation of a heating unit using percussion ignition is described in Example 11. The advantages of such an ignition system over resistive ignition are that it eliminates the need for use of battery and is a very cost effective means of ignition.

Optical Ignition

Optical ignition can also be used to ignite the heating unit. Optical ignition requires the use either a light sensitive material or initiator composition and a light source for actuation of the light sensitive material or initiator composition or a very high intensity light source, e.g., a laser.

Various light sensitive initiator compositions can be used, but they generally consist of combustible materials that are light absorptive or are coated with light absorptive chemicals. Black powder and nitrocellulose powders are sufficiently light absorptive without any coatings. Metal and oxidizing agent compositions, such as those discussed above, can also be used. In certain embodiments, metals such as, for example, aluminum, zirconium, and titanium and oxidizing agents such as potassium chlorate, potassium perchlorate, copper oxide, tungsten trioxide, and molybdenum trioxide can be used. Initiator compositions that are sensitive to a specific wavelength or range of wavelengths, such as, for example, compositions that are highly absorptive in the ultraviolet region of the electromagnetic spectrum can also be used.

The initiator material can be applied directly to the fuel on the substrate or positioned elsewhere within the heating unit. In certain embodiments, initiator compositions can be within a hole in glass fiber filter that is placed adjacent to the surface of the coated fuel.

Ignition of the fuel in a heat package is actuated by transmission of a light pulse through a clear optical window to the initiator compositions. The optical window can be made of any material that readily transmits a light pulse, such as for example, glass, acrylic, or polycarbonate. The window can be positioned in any location to transmit the light to the initiator. li certain embodiments, the window forms part of the enclosure of the heating unit. In other embodiments, the window is completely contained in the system. In certain embodiments the window is part of a light guide assembly. The light guide assembly can also consist of a beam splitter. The light coming from the light source passes through the beam splitter and can directed to two or more initiator compositions located within the heating unit for initiation of two or more fuel coated substrates at the same time or in sequence. Optionally, an optical fiber can be used to fire multiple heating units at the same time. In other embodiments, the window can be coated by a material which causes the wavelength of the light which it emits to be different from the light which it receives. For example, the radiant optical source could emit ultraviolet light, and the coating could be used to give off a visible wavelength in response to the ultraviolet light.

Various means for actuating the optical ignition can be used. In certain embodiments, an electrically conductive means for generating a light pulse upon achieving a threshold voltage is provided. The electrically conductive means can be part of the heating unit itself, e.g., included in a spacer of the heating unit or separate from the heating unit. The electrically conductive means for generating a light pulse can include, for example a Xenon flash lamp, a light emitting diode, and a laser.

Figure 20A:
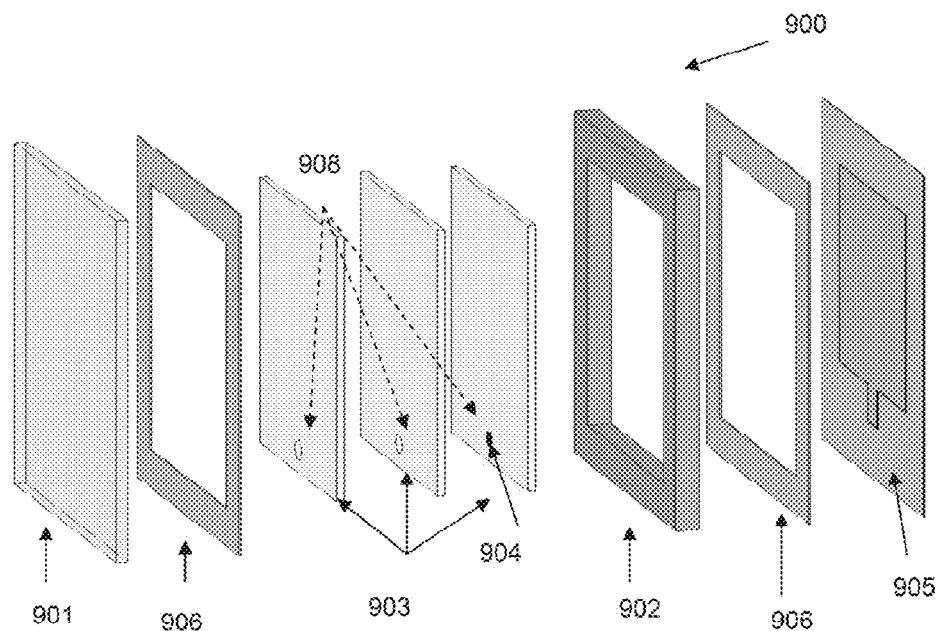
Figure 20B:
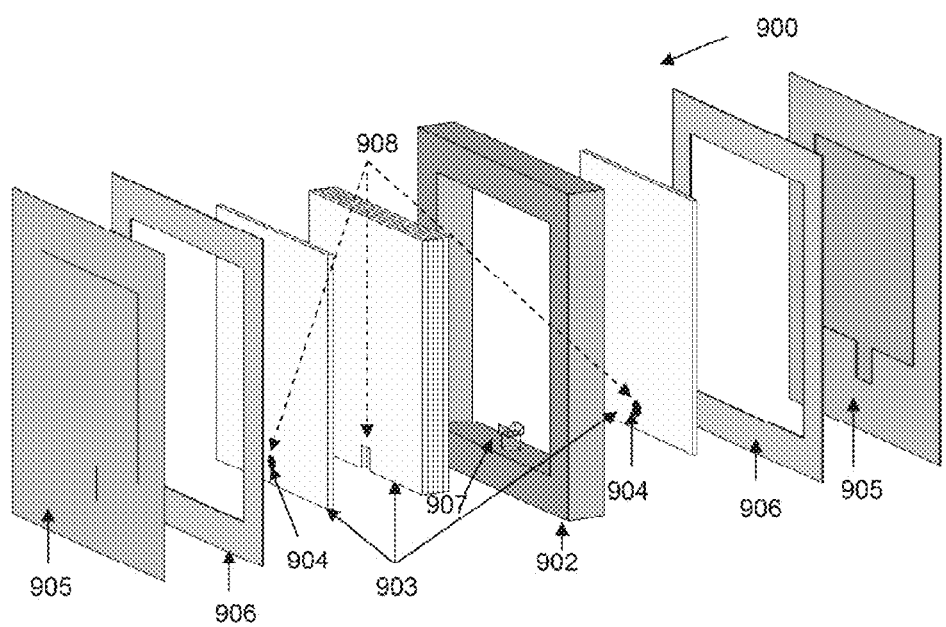
Figure 20C:
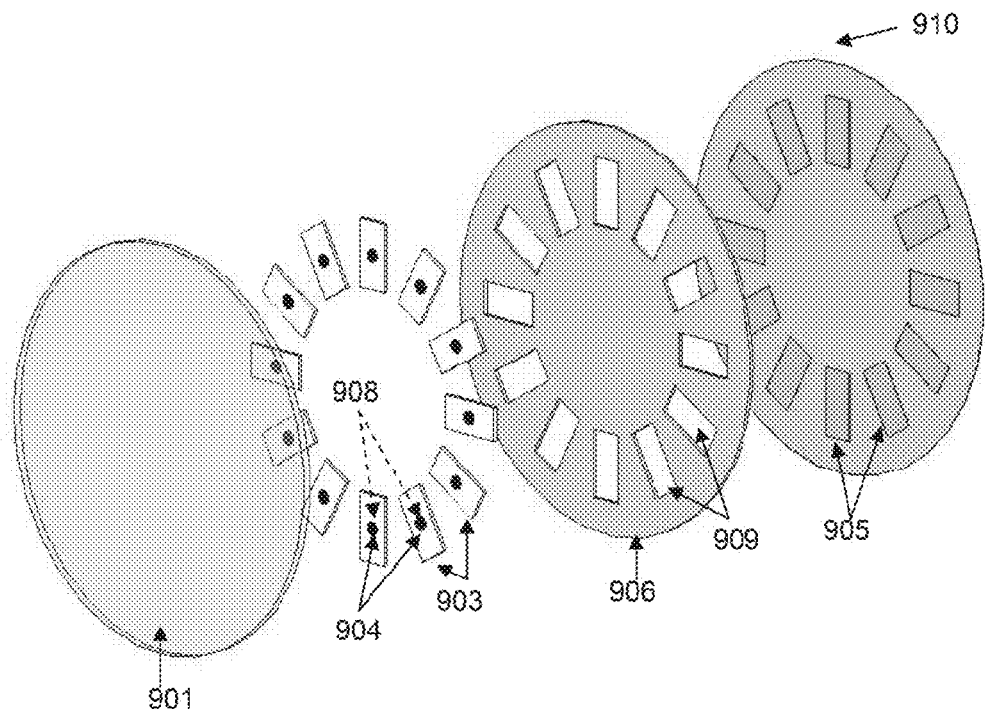

Several embodiments of a heating unit 900 comprising an optical ignition system are illustrated in FIGS. 20A-D. As shown in 20A-D, an initiator composition 904 is contained within a hole 908 in an impulse absorbing material 903, such that the initiator composition 904 is adjacent to the fuel coating. One or more impulse absorbing materials 903 can be added to the heating unit, as long as there is not an obstruction by the impulse absorbing material that would prevent contact between the ignited initiator composition and the solid fuel. Holes or spaces 908 can be cut into the impulse absorbing materials 903 to provide an opening for such contact, as is demonstrated in FIGS. 20A-B. More than one initiator composition 904 can be placed in a single heating unit 900, as shown in FIGS. 20B and D, for initiating the firing of more than one solid fuel coating at a time. Additionally, a single initiator composition 904 can be placed in each impulse absorbing material 903, to form several heating units combined in one device 910, such as demonstrated in FIG. 20C. The impulse absorbing material can be fit into a spacer 902 as shown in FIGS. 20A-B, and FIG. D, or into a cavity 909 generated in multiply layers of a sealant 906, as shown in FIG. 20C.

As shown in FIG. 20A and FIG. 20C, an optical window 901 can form part of the enclosure of the heating unit. In some embodiments, the optical window 901 forms part of a wave guide system (not shown) which includes a beam splitter 907, as shown in FIG. 20B. The beam splitter 907 can be used to direct one source of light to two initiator compositions so as to ignite both solid fuel coated substrates 905 together.

Various means can be used to seal the heating unit. Sealant 906 can be an adhesive, such as double sided tape or epoxy, or any other methods for forming a seal, such as for example, welding, soldering, fastening or crimping.

Figure 20D:
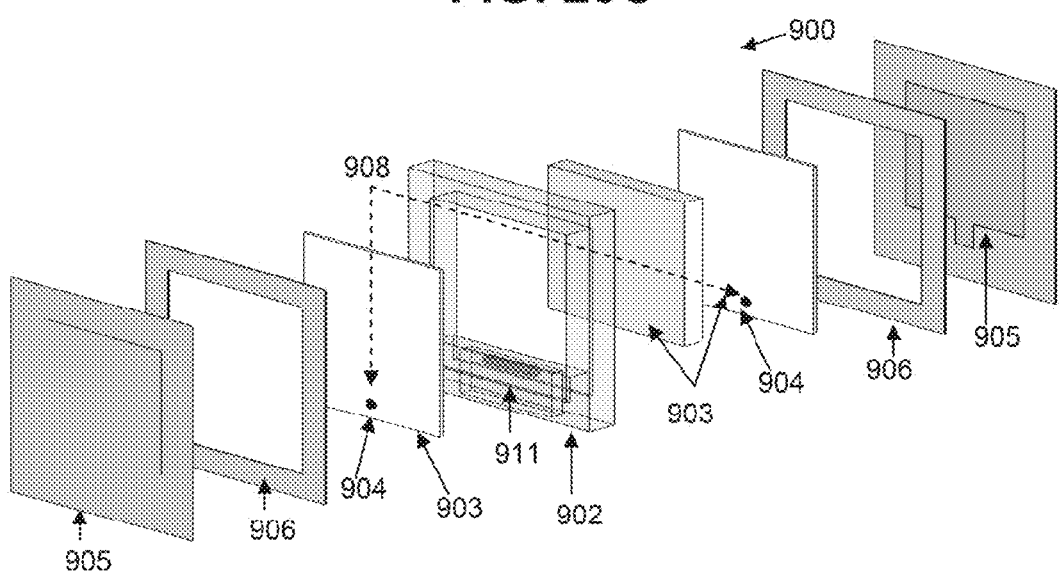

In certain embodiments, the light source 911 is part of the heating unit, and can be contained within the spacer 902 contained in the heating unit 900, as shown in FIG. 20D. The light source can be powered by a battery (not shown).

An example of the preparation of a single heating unit using optical ignition is described in Example 11. Example 12 describes the preparation of a device with multiple optically ignitable heating units. One advantage of such an ignition system is that there is no need for a direct electrical connection between a battery and the initiator composition, as is required for electrical resistive heating. Additionally, the initiator composition can be ignited within the heating unit without the need for a bridgewire.

Drug Supply Unit

Certain embodiments include a drug supply unit comprising a heating unit as described herein. A drug supply unit can be used in a drug delivery device where a drug is to be thermally vaporized and then condensed for administration to a user. In certain embodiments, the drug condensate can be administered by inhalation, nasal ingestion, or topically. Drug refers to any compound for therapeutic use or non-therapeutic use, including therapeutic agents and substances. Therapeutic agent refers to any compound for use in the diagnosis, cure, mitigation, treatment, or prevention of disease, and any compound used in the mitigation or treatment of symptoms of disease. Whereas, substances refer to compounds used for a non-therapeutic use, typically for a recreational or experimental purpose.

Figure 6A:
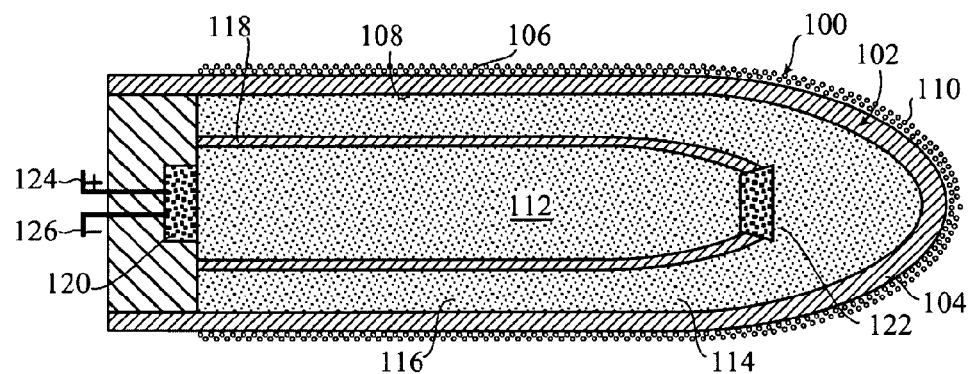
FIGS. 6A-6C show schematic illustrations of the generation of drug vapor from a drug supply unit carrying a film of drug on the exterior substrate surface (FIG. 6A); ignition of the he
Figure 6B:
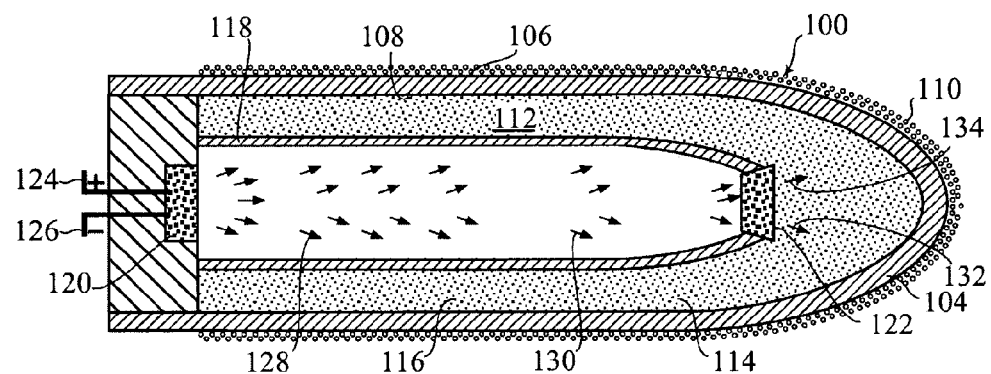
Figure 6C:
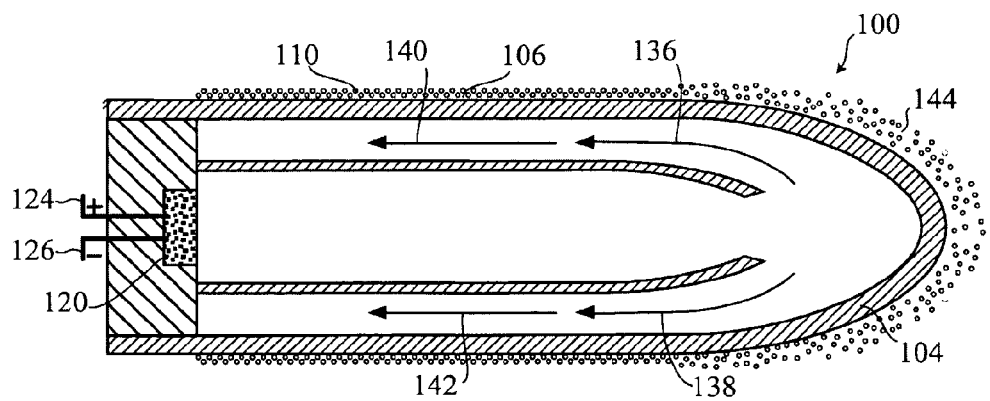
Figure 7A:
Figure 7B:
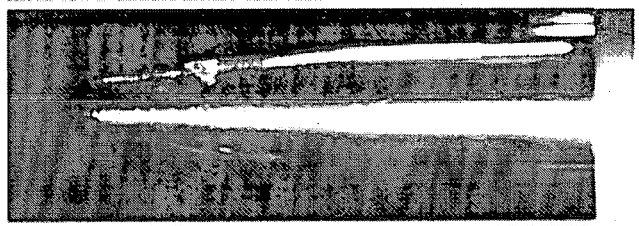
Figure 7C:
Figure 7D:
Figure 7E:

FIGS. 6A-6C schematically illustrate cross-sectional views of a drug supply unit 100 comprising a heating unit similar to that described in FIG. 2B. More specifically, FIGS. 6A-6C illustrate a drug supply unit 100 having a film of drug disposed on the exterior substrate surface (FIG. 6A); ignition of the heating unit (FIG. 6B); and generation of a wave of heat effective to vaporize the drug film (FIG. 6C). With initial reference to FIG. 6A, drug supply unit 100 comprises a heating unit 102, similar to that described in FIG. 2B. In FIGS. 6A-B, a substantially cylindrically-shaped, heat-conductive substrate 104 has an exterior surface 106 and an interior surface 108, which define an inner region 112. A film 110 of drug can be disposed on all or a portion of exterior surface 106.

In certain embodiments, film 110 can be applied to exterior substrate surface 106 by any appropriate method and can depend at least in part on the physical properties of the drug and the final thickness of the film. In certain embodiments, methods of applying a drug to the exterior substrate surface include, but are not limited to, brushing, dip coating, spray coating, screen printing, roller coating, inkjet printing, vapor-phase deposition, spin coating, and the like. In certain embodiments, the drug can be prepared as a solution comprising at least one solvent and applied to the exterior surface. In certain embodiments, a solvent can comprise a volatile solvent such as, for example, but not limitation, acetone or isopropanol. In certain embodiments, the drug can be applied to the exterior surface of the substrate as a melt. In certain embodiments, the drug can be applied to a support having a release coating and transferred to a substrate from the support. For drugs that are liquid at room temperature, thickening agents can be admixed with the drug to produce a viscous composition comprising the drug that can be applied to the exterior substrate surface by any appropriate method, including those described herein. In certain embodiments, a film of compound can be formed during a single application or can be formed during repeated applications to increase the final thickness of the film. In certain embodiments, the final thickness of a film of drug disposed on the exterior substrate surface can be less than 50 μm, in certain embodiments less than 20 μm and in certain embodiments less than 10 μm, in certain embodiments the film thickness can range from 0.02 μm to 20 μm, and in certain embodiments can range from 0.1 μm to 10 μm.

In certain embodiments, the film can comprise a therapeutically effective amount of at least one drug. Therapeutically effective amount refers to an amount sufficient to affect treatment when administered to a patient or user in need of treatment. Treating or treatment of any disease, condition, or disorder refers to arresting or ameliorating a disease, condition or disorder, reducing the risk of acquiring a disease, condition or disorder, reducing the development of a disease, condition or disorder or at least one of the clinical symptoms of the disease, condition or disorder, or reducing the risk of developing a disease, condition or disorder or at least one of the clinical symptoms of a disease or disorder. Treating or treatment also refers to inhibiting the disease, condition or disorder, either physically, e.g. stabilization of a discernible symptom, physiologically, e.g., stabilization of a physical parameter, or both, and inhibiting at least one physical parameter that may not be discernible to the patient. Further, treating or treatment refers to delaying the onset of the disease, condition or disorder or at least symptoms thereof in a patient which may be exposed to or predisposed to a disease, condition or disorder even though that patient does not yet experience or display symptoms of the disease, condition or disorder. In certain embodiments, the drug film can comprise one or more pharmaceutically acceptable carriers, adjuvants, and/or excipients. Pharmaceutically acceptable refers to approved or approvable by a regulatory agency of the Federal or a state government or listed in the U.S Pharmacopoeia or other generally recognized pharmacopoeia for use in animals, and more particularly in humans.

As shown in FIGS. 6A-6C, substrate 104 of drug supply unit 100 can define an inner region 112 in which a solid fuel 114 can be disposed. As shown, solid fuel 114 can be disposed as an annular shell defined by interior substrate surface 108 and an inner, cylindrical backing member 118. A first initiator composition 120 can be located at one end of cylindrical backing member 118 and a second initiator composition 122 can be located at the opposing end of cylindrical backing member 118. First initiator composition 120 can be in physical contact with an electrically resistive heating element via electrical leads 124, 126 to a power source (not shown).

As shown in FIGS. 6B, application of an electrical current provided by a power source (not shown) to leads 124, 126 can cause initiator composition 120 to produce sparks, such as sparks 128, 130 that can be directed toward second initiator composition 122. Ignition of second initiator composition 122 can ignite solid fuel 114 in the region indicated by mows 132, 134. Igniting solid fuel 114 in the region indicated by arrows 132, 134 effectuates a self-propagating wave of burning solid fuel, as schematically illustrated in FIG. 6C. In FIG. 6C, the self-propagating burn is indicated by arrows 136, 138, 140, 142 with the solid fuel burn propagating from the point of ignition through the solid fuel. As the solid fuel burns, heat can be produced that can be conducted through substrate 104 causing vaporization of drug film 110 disposed on external substrate surface 106. In FIG. 6C, thermally vaporized drug is illustrated as the “cloud” of drug 144. In certain embodiments, as illustrated in FIG. 6C, vaporization of the drug occurs in the direction of arrows 136, 138, 140, 142, where the film nearest the ignition point of the solid fuel is vaporized first, followed by vaporization in regions along the length of drug supply unit 100. As shown in FIG. 6C, thermally vaporized drug 144 is illustrated at the tapered region of drug supply unit 100, and drug film not yet vaporized from the exterior surface 106 is illustrated at point 110.

FIGS. 7A-7E represent high-speed photographs showing the thermal generation of a vapor from a drug supply unit similar to that described in FIGS. 6A-6C. FIG. 7A shows a heat-conductive substrate 4 cm in length coated with a 3 μm to 5 μm thick film of the therapeutic agent alprazolam. The drug-coated substrate was placed in a chamber through which a stream of air was flowing in an upstream-to-downstream direction, indicated by the arrow in FIG. 7A, at a rate of 15 L/min Solid fuel contained in the heating unit was ignited to heat the substrate. The progression of drug vaporization from the exterior surface of the drug supply unit was monitored using real-time photography. FIGS. 7B-7E show the sequence of thermal vaporization at time intervals of 150 msec, 250 msec, 500 msec, and 1,000 msec, following ignition of an initiator composition, respectively. The cloud of thermal vapor formed from the drug film is visible in the photographs. Complete vaporization of the drug film was achieved in less than 1,000 msec.

The drug supply unit is configured such that the solid fuel heats a portion of the exterior surface of the substrate to a temperature sufficient to thermally vaporize the drug in certain embodiments within at least 3 seconds following ignition of the solid fuel, in other embodiments within 1 second following ignition of the solid fuel, in other embodiments within 800 milliseconds following ignition of the solid fuel, in other embodiments within 500 milliseconds following ignition of the solid fuel, and in other embodiments within 250 milliseconds following ignition of the solid fuel.

In certain embodiments, a drug supply unit can generate an aerosol comprising a drug that can be inhaled directly by a user and/or can be mixed with a delivery vehicle, such as a gas, to produce a stream for delivery, e.g., via a spray nozzle, to a topical site for a variety of treatment regimens, including acute or chronic treatment of a skin condition, administration of a drug to an incision site during surgery, or to an open wound.

In certain embodiments, rapid vaporization of a drug film can occur with minimal thermal decomposition of the drug. For example, in certain embodiments, less than 10% of the drug is decomposed during thermal vaporization, and in certain embodiments, less than 5% of the drug is decomposed during thermal vaporization. In certain embodiments, a drug can undergo a phase transition to a liquid state and then to a gaseous state, or can sublime, i.e., pass directly from a solid state to a gaseous state. In certain embodiments, a drug can include a pharmaceutical compound. In certain embodiments, the drug can comprise a therapeutic compound or a non-therapeutic compound. A non-therapeutic compound refers to a compound that can be used for recreational, experimental, or pre-clinical purposes. Classes of drugs that can be used include, but are not limited to, anesthetics, anticonvulsants, antidepressants, antidiabetic agents, antidotes, antiemetics, antihistamines, anti-infective agents, antineoplastics, antiparkisonian drugs, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, opthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

Examples of anesthetic include ketamine and lidocaine.

Examples of anticonvulsants include compounds from one of the following classes: GABA analogs, tiagabine, vigabatrin; barbiturates such as pentobarbital; benzodiazepines such as clonazepam; hydantoins such as phenytoin; phenyltriazines such as lamotrigine; miscellaneous anticonvulsants such as carbamazepine, topiramate, valproic acid, and zonisamide.

Examples of antidepressants include amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, escitalopram, tofenacin, trazodone, tryptophan, and zalospirone.

Examples of antidiabetic agents include pioglitazone, rosiglitazone, and troglitazone.

Examples of antidotes include edrophonium chloride, flumazenil, deferoxamine, nalmefene, naloxone, and naltrexone.

Examples of antiemetics include alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

Examples of antihistamines include astemizole, azatadine, brompheniramine, carbinoxamine, cetrizine, chlorpheniramine, cinnarizine, clemastine, cyproheptadine, dexmedetomidine, diphenhydramine, doxylamine, fexofenadine, hydroxyzine, loratidine, promethazine, pyrilamine and terfenidine.

Examples of anti-infective agent include compounds selected from one of the following classes: antivirals such as efavirenz; AIDS adjunct agents such as dapsone; aminoglycosides such as tobramycin; antifungals such as fluconazole; antimalarial agents such as quinine; antituberculosis agents such as ethambutol; β-lactams such as cefmetazole, cefazolin, cephalexin, cefoperazone, cefoxitin, cephacetrile, cephaloglycin, cephaloridine; cephalosporins, such as cephalosporin C, cephalothin; cephamycins such as cephamycin A, cephamycin B, and cephamycin C, cephapirin, cephradine; leprostatics such as clofazimine; penicillins such as ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin, penicillin N, penicillin O, penicillin S, penicillin V, dicloxacillin; diphenicillin; heptylpenicillin; and metampicillin; quinolones such as ciprofloxacin, clinafloxacin, difloxacin, grepafloxacin, norfloxacin, ofloxacine, temafloxacin; tetracyclines such as doxycycline and oxytetracycline; miscellaneous anti-infectives such as linezolide, trimethoprim and sulfamethoxazole.

Examples of anti-neoplastic agents include droloxifene, tamoxifen, and toremifene.

Examples of antiparkisonian drugs include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinerole, selegiline, spheramine, terguride, entacapone, and tolcapone.

Examples of antirheumatic agents include diclofenac, hydroxychloroquine and methotrexate.

Examples of antipsychotics include acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine, and zuclopenthixol.

Examples of anxiolytics include alprazolam, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

An example of an appetite stimulant is dronabinol.

Examples of appetite suppressants include fenfluramine, phentermine and sibutramine Examples of blood modifiers include cilostazol and dipyridamol.

Examples of cardiovascular agents include benazepril, captopril, enalapril, quinapril, ramipril, doxazosin, prazosin, clonidine, labetolol, candesartan, irbesartan, losartan, telmisartan, valsartan, disopyramide, flecanide, mexiletine, procainamide, propafenone, quinidine, tocainide, amiodarone, dofetilide, ibutilide, adenosine, gemfibrozil, lovastatin, acebutalol, atenolol, bisoprolol, esmolol, metoprolol, nadolol, pindolol, propranolol, sotalol, diltiazem, nifedipine, verapamil, spironolactone, bumetanide, ethacrynic acid, furosemide, torsemide, amiloride, triamterene, and metolazone.

Examples of central nervous system stimulants include amphetamine, brucine, caffeine, dexfenfluramine, dextroamphetamine, ephedrine, fenfluramine, mazindol, methyphenidate, pemoline, phentermine, sibutramine, and modafinil.

Examples of drugs for Alzheimer's disease management include donepezil, galanthamine and tacrin.

Examples of drugs for cystic fibrosis management include CPX, IBMX, XAC and analogues; 4-phenylbutyric acid; genistein and analogous isoflavones; and milrinone.

Examples of diagnostic agents include adenosine and aminohippuric acid.

Examples of dietary supplements include melatonin and vitamin-E.

Examples of drugs for erectile dysfunction include tadalafil, sildenafil, vardenafil, apomorphine, apomorphine diacetate, phentolamine, and yohimbine.

Examples of gastrointestinal agents include loperamide, atropine, hyoscyamine, famotidine, lansoprazole, omeprazole, and rebeprazole.

Examples of hormones include: testosterone, estradiol, and cortisone.

Examples of drugs for the treatment of alcoholism include naloxone, naltrexone, and disulfiram.

Examples of drugs for the treatment of addiction it is buprenorphine.

Examples of immunosupressives includemycophenolic acid, cyclosporin, azathioprine, tacrolimus, and rapamycin.

Examples of mast cell stabilizers include cromolyn, pemirolast, and nedocromil.

Examples of drugs for migraine headache include almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Examples of motion sickness products include diphenhydramine, promethazine, and scopolamine.

Examples of drugs for multiple sclerosis management include bencyclane, methylprednisolone, mitoxantrone, and prednisolone.

Examples of muscle relaxants include baclofen, chlorzoxazone, cyclobenzaprine, methocarbamol, orphenadrine, quinine, and tizanidine.

Examples of nonsteroidal anti-inflammatory drugs include aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib.

Examples of opioid drugs include alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Examples of other analgesic drugs include apazone, benzpiperylon, benzydramine, caffeine, clonixin, ethoheptazine, flupirtine, nefopam, orphenadrine, propacetamol, and propoxyphene.

Examples of opthalmic preparation drugs include ketotifen and betaxolol.

Examples of osteoporosis preparation drugs alendronate, estradiol, estropitate, risedronate and raloxifene.

Examples of prostaglandin drugs include epoprostanol, dinoprostone, misoprostol, and alprostadil.

Examples of respiratory agents include albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, and pirfenidone Examples of sedative and hypnotic drugs include butalbital, chlordiazepoxide, diazepam, estazolam, flunitrazepam, flurazepam, lorazepam, midazolam, temazepam, triazolam, zaleplon, zolpidem, and zopiclone.

Examples of skin and mucous membrane agents include isotretinoin, bergapten and methoxsalen.

Examples of smoking cessation aids include nicotine and varenicline.

An example of a Tourette's syndrome agent includes pimozide.

Examples of urinary tract agents include tolteridine, darifenicin, propantheline bromide, and oxybutynin.

Examples of vertigo agents include betahistine and meclizine.

In certain embodiments, a drug can further comprise substances to enhance, modulate and/or control release, aerosol formation, intrapulmonary delivery, therapeutic efficacy, therapeutic potency, stability, and the like. For example, to enhance therapeutic efficacy a drug can be co-administered with one or more active agents to increase the absorption or diffusion of the first drug through the pulmonary alveoli, or to inhibit degradation of the drug in the systemic circulation. In certain embodiments, a drug can be co-administered with active agents having pharmacological effects that enhance the therapeutic efficacy of the drug. In certain embodiments, a drug can comprise compounds that can be used in the treatment of one or more diseases, conditions, or disorders. In certain embodiments, a drug can comprise more than one compound for treating one disease, condition, or disorder, or for treating more than one disease, condition, or disorder.

Thin Film Drug Supply Unit

An embodiment of a thin film drug supply unit is illustrated in FIGS. 10A-10B. FIG. 10A illustrates a perspective view, and FIG. 10B an assembly view of a thin film drug supply unit 500. Thin film drug supply unit 500 comprises, as shown in FIG. 10B, a thin film heating unit 530 on which is disposed a drug 514 to be thermally vaporized. As shown in FIG. 10A, thin film heating unit 530 comprises a first and a second substrate 510, and a spacer 518.

As shown, first and second substrates 510 include an area comprising solid fuel 512 disposed on the interior surface, and an area comprising a drug 514 to be vaporized disposed on the exterior surface. First and second substrates 510 can comprise a thermally conductive material such as those described herein, including, for example, metals, ceramics, and thermally conductive polymers. In certain embodiments, substrates 510 can comprise a metal, such as, but not limited to, stainless steel, copper, aluminum, and nickel, or an alloy thereof. Substrates can have one or more layers, and the multiple layers can comprise different materials. For example, a substrate can comprise multiple layers of laminated metal foils, and/or can comprise thin films of one or more materials deposited on the surface. The multiple layers can be used for example to determine the thermal properties of the substrate and/or can be used to determine the reactivity of the surface with respect to a compound disposed on the exterior surface. A multilayer substrate can have regions comprising different materials. The thickness of substrates 510 can be thin to facilitate heat transfer from the interior to the exterior surface and/or to minimize the thermal mass of the device. In certain embodiments, a thin substrate can facilitate rapid and homogeneous heating of the exterior surface with a lesser amount of solid fuel compared to a thicker substrate. Substrate 510 can also provide structural support for solid fuel 512 and drug film 514. In certain embodiments, substrates 510 can comprise a metal foil. In certain embodiments, the thickness of substrates 510 can range from 0.001 inches to 0.020 inches, in certain embodiments from 0.001 inches to 0.010 inches, in certain embodiments from 0.002 inches to 0.006 inches, and in certain embodiments from 0.002 inches to 0.005 inches. The use of lesser amounts of solid fuel can facilitate control of the heating process as well as facilitate miniaturization of a drug supply unit.

In certain embodiments, the thickness of substrates 510 can vary across the surface. For example, a variable thickness can be useful for controlling the temporal and spatial characteristics of heat transfer and/or to facilitate sealing of the edges of substrates 510, for example, to spacer 518, opposing substrate 510, or to another support (not shown). In certain embodiments, substrates 510 can exhibit a homogeneous or nearly homogeneous thickness in the region of the substrate on which solid fuel 512 and drug 514 are disposed to facilitate achieving a homogeneous temperature across that region of the substrate on which the solid fuel is disposed. Homogeneous heating of the substrate can facilitate the production of an aerosol comprising a high purity of a drug or pharmaceutical composition and maximize the yield of drug initially deposited on the substrate forming an aerosol.

Substrates 510 can comprise an area of solid fuel 512 disposed on the interior surface, e.g. the surface facing opposing substrate 510. An appropriate amount of solid fuel 512 can in part be determined by the thermal vaporization or sublimation temperature of the drug, the amount of drug to be vaporized, the thickness and thermal conductivity of the substrate, the composition of the solid fuel, and the temporal characteristics of the intended thermal vaporization process. Solid fuel 512 can be applied to substrate 510 using any appropriate method. For example, solid fuel 512 can be applied to substrate 510 by brushing, dip coating, screen printing, roller coating, spray coating, inkjet printing, stamping, spin coating, and the like. To facilitate processing, solid fuel 510 can comprise at least one additive material, and/or a solvent, as disclosed herein. In certain embodiments, solid fuel 512 can be formed as a preformed sheet that can be cut to a specific dimension and subsequently applied to substrate 510. In certain embodiments, the solid fuel can be applied to a support, and transferred to a substrate as a preformed section.

Solid fuel 512 can be applied to a portion of substrates 510 as a thin film or layer. The thickness of the thin layer of solid fuel 512, and the composition of solid fuel 512 can determine the maximum temperature as well as the temporal and spatial dynamics of the temperature profile produced by the burning of the solid fuel.

Studies using thin solid fuel layers having a thickness ranging from 0.001 inches to 0.005 inches demonstrate that the maximum temperature reached by a thin film substrate on which the solid fuel is disposed can be linear with the mass of solid fuel applied. For example, as shown in FIG. 12 for several different solid fuel compositions, for a 0.001 inch to 0.003 inch thick layer of $Zr/MoO_3$ solid fuel having a mass ranging from 0.13 g to 0.25 g, the maximum temperature reached by the substrate during bum is linear. Other studies with solid fuel layers having a mass ranging from 0.12 g to 0.24 g demonstrate linearity over a temperature ranging from 375° C. to 625° C. It will be appreciated that one skilled in the art can establish similar relationships for other solid fuel compositions and configurations. Such studies demonstrate that the temperature reached by the substrate when the solid fuel is burned can be established by controlling the amount of solid fuel applied to the substrate.

Measurements of the substrate surface temperature demonstrate that thin coatings of a solid fuel comprising a metal reducing agent and a metal-containing oxidizing agent can produce homogenous heating. A temperature profile of a substrate forming a heating unit substantially as shown in FIGS. 10A and 10B and described in Example 9 following ignition of the solid fuel is shown in FIG. 19. FIG. 19 shows the average surface temperature at various positions across two dimensions of a 1.3 inch×1.3 inch substrate 0.25 seconds following ignition of a 0.00163 inch thick coating of solid fuel. The average surface temperature of the effective heated area was about 400° C. In certain embodiments, the average surface temperature of a 1.3 inch×1.3 inch substrate heated by a thin coating of solid fuel can exhibit a standard deviation ranging from about 8° C. to 50° C.

Measurements of the substrate surface temperature after firing demonstrate that thin coatings or layers of a solid fuel comprising a metal reducing agent and a metal-containing oxidizing agent can produce uniformity of temperature on the exterior surface of the substrate. Uniformity of temperature is defined herein to exist when the temperature in degrees Celsius of the exterior surface of the substrate, corresponding to the fuel coated area of the interior surface of the substrate, is within a standard deviation of 50° C. from the average surface temperature obtained, as measured within 100 milliseconds after completion of propagation of the ignited fuel flame front. A temperature profile of a substrate forming a heating unit substantially as shown in FIGS. 10A and 10B and described in Example 9 following ignition of the solid fuel is shown in FIG. 19. FIG. 19 shows the average surface temperature at various positions across two dimensions of a 1.3 inch×1.3 inch substrate 0.25 seconds following ignition of a 0.00163 inch thick coating of solid fuel.

In certain applications, such as for example, vaporization of a drug off the substrate of a heating unit, uniformity of heating of the substrate is critical as it facilitates the production of an aerosol comprising a high purity drug or pharmaceutical composition and maximizes the yield of drug initially deposited on the substrate forming an aerosol.

In certain embodiments, solid fuel 512 can comprise a mixture of $Zr/MoO_3$, $Zr/Fe_2O_3$, $Al/MoO_3$, or $Al/Fe_2O3$. In certain embodiments, the amount of metal reducing agent can range from 60 wt % to 90 wt %, and the amount of metal-containing oxidizing agent can range from 40 wt % to 10 wt %. In certain embodiments, higher ratios of metal reducing agent can cause the solid fuel to burn slower and at a lower temperature, whereas lower ratios of metal reducing agent can cause the solid fuel to burn faster and reach a higher maximum temperature. Regardless of the weight percent ratios of the metal reducing agent and metal-containing oxidizing agent, a solid fuel can comprise a stoichiometric amount of metal reducing agent and metal-containing oxidizing agent. For example, the balanced $Zr:Fe_2O_3$ metal oxidation-reduction reaction can be written as:

$$3\ Zr + 2\ Fe_2O_3 \rightarrow 3\ ZrO_2 + 4\ Fe$$

A stoichiometric amount of $Zr:Fe_2O_3$ for this reaction is 1:1.67 by weight.

Drug 514 can be disposed on the exterior surface of substrates 510. The amount of drug 514 disposed on the exterior surface of substrate 510 can be any appropriate amount. For example, the amount of drug 514 can be a therapeutically effective amount. A therapeutically effective amount can be determined by the potency of the drug, the clinical indications, and the mode of administration. In certain embodiments, thin film drug supply unit can be configured to thermally vaporize more than 95% of the drug, and in certain embodiments, greater than 98% of the drug, with minimal degradation of the drug. The aerosol formed using a drug supply unit can comprise greater than 90% of a drug applied to a substrate, and in certain embodiments greater than 95% of a drug applied to a substrate. The yield and purity of the aerosol can be controlled by and selected based on the temporal characteristics and magnitude of the thermal impulse transferred to the compound.

Figure 18:
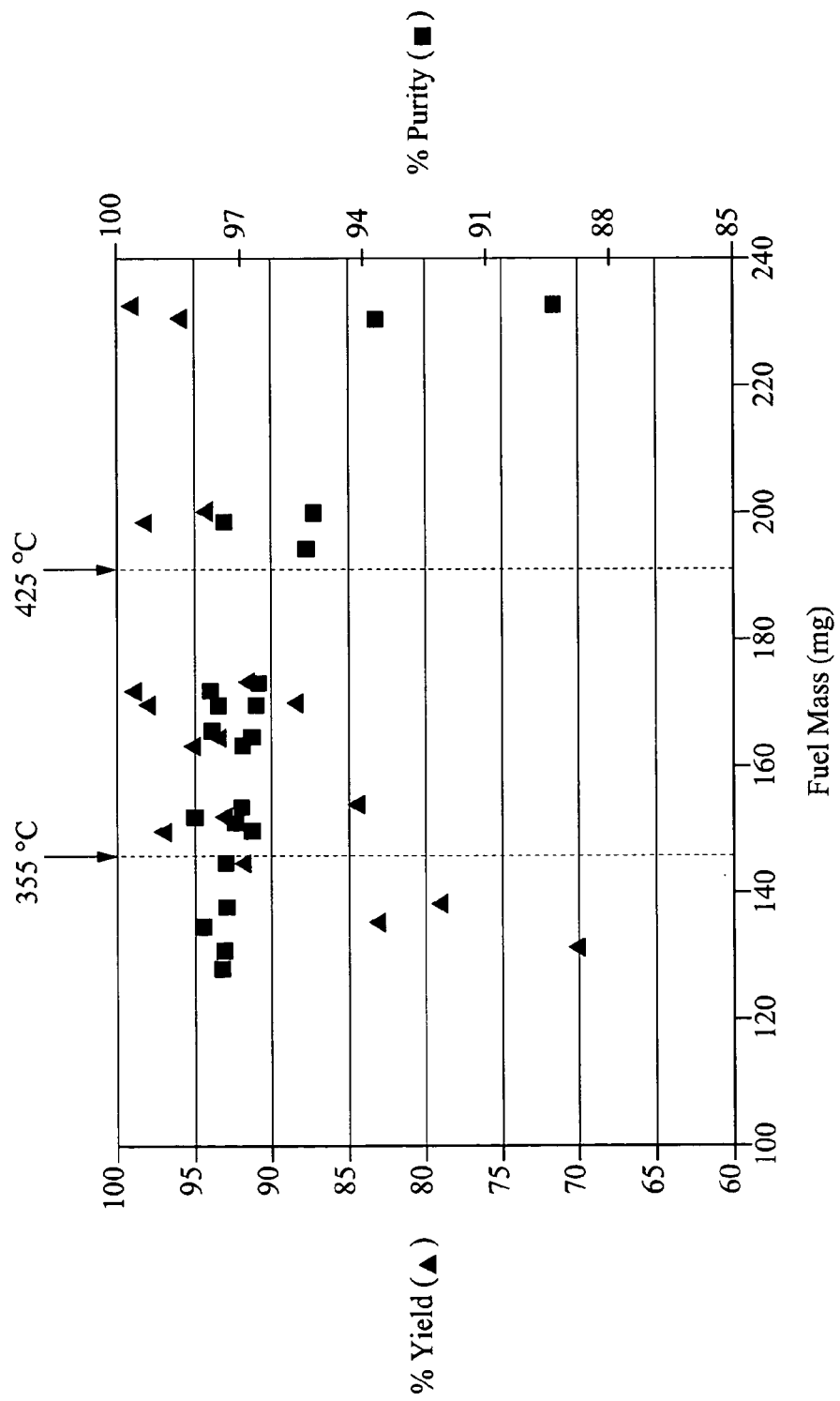
FIG. 18 shows the relationship of the yield and purity of an aerosol comprising a specific pharmaceutical compound using different substrate temperatures obtained from different masses of solid fuel for various embodiments.
Figure 19:
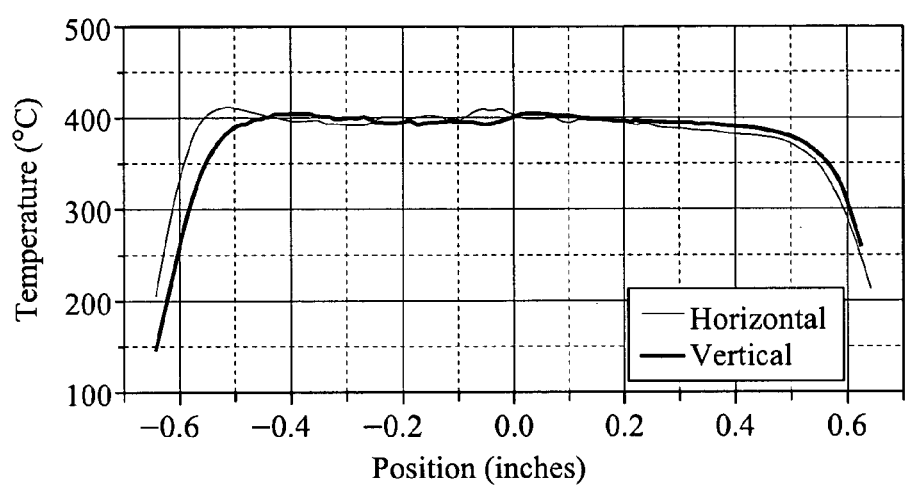
FIG. 19 shows a iron, cobalt, nickel, copper, zinc, cadmium, tin, antimony, bismuth, aluminum, and silicon. In certain embodiments, a metal reducing agent can include aluminum, zirconium, and titanium. In certain embodiments, a metal reducing agent can comprise more than one metal reducing agent.

The relationship of the yield and purity of an aerosol comprising a pharmaceutical compound on the substrate temperature and mass of solid fuel for certain embodiments is shown in FIG. 18. Thin film drug supply units substantially as shown in FIGS. 10A and 10B, and described in Example 9 were used to produce the measurements shown in FIG. 18. The experimental arrangement used to analyze the percent yield and percent purity of the aerosol comprising a vaporized drug is described in Example 10. As shown in FIG. 18, at substrate temperatures ranging from about 355° C. to about 425° C., the percent yield of drug forming the aerosol was greater than about 85% and the percent purity was greater than about 90%. The percent yield refers to the ratio of the total solid weight of the aerosol to the weight of the drug initially deposed on the substrate times 100. Factors that can reduce the percent yield include incomplete vaporization of the drug and redeposition of the drug on the substrate.

The percent purity, with respect to the aerosol purity, refers to the fraction of drug composition in the aerosol/the fraction of drug composition in the aerosol plus drug degradation products times 100. Thus purity is relative with regard to the purity of the starting material. For example, when the starting drug or drug composition used for substrate coating contained detectable impurities, the reported purity of the aerosol does not include those impurities present in the starting material that were also found in the aerosol, e.g., in certain cases if the starting material contained a 1% impurity and the aerosol was found to contain the identical 1% impurity, the aerosol purity may nevertheless be reported as >99% pure, reflecting the fact that the detectable 1% purity was not produced during the vaporization-condensation aerosol generation process.

Factors that can reduce the percent purity of the aerosol include degradation of the drug during thermal vaporization. Depending at least in part on the composition and thermal properties of a particular drug or pharmaceutical composition, the appropriate thermal vaporization temperature to produce an aerosol comprising the particular drug or pharmaceutical composition having high yield and purity can be determined as set forth in U.S. application Ser. No. 10/718,982, filed Nov. 20, 2003.

Drug 514 can be applied to substrate 510 using any appropriate method, such as for example, brushing, dip coating, screen printing, roller coating, spray coating, inkjet printing, stamping, vapor deposition, and the like. Drug 514 can also be applied to a support having a release layer and transferred to substrate 510. Drug 514 can be suspended in a volatile solvent such as, for example, but not limited to, acetone or isopropanol to facilitate application. A volatile solvent can be removed at room temperature or at elevated temperature, with or without application of a vacuum. In certain embodiments, the solvent can comprise a pharmaceutically acceptable solvent. In certain embodiments, residual solvent can be reduced to a pharmaceutically acceptable level.

Drug 514 can be disposed on substrate 510 in any appropriate form such as a solid, viscous liquid, liquid, crystalline solid, or powder. In certain embodiments, the film of drug can be crystallized after disposition on the substrate.

As shown in FIGS. 10A-10B, a drug supply unit can comprise an igniter 520. In certain embodiments, igniter 520 can comprise an initiator composition 522 disposed on an electrically resistive heating element connected to electrical leads disposed between two strips of insulating materials (not shown). The electrical leads can be connected to a power source (not shown). Initiator composition 522 can comprise any of the initiator compositions or compositions described herein. In certain embodiments, the ignition temperature of initiator composition can range from 200° C. to 500° C. The electrically resistive material can comprise a material capable of generating heat when electrical current is applied. For example, the electrically resistive material can be a metal such as nichrome, tungsten or graphite. An initiator composition can be disposed on the surface of the electrically resistive material such that when the electrically resistive material is heated to the ignition temperature of the initiator composition, the initiator composition can ignite to produce sparks. An initiator composition can be applied to the electrically resistive heating element by depositing a slurry comprising the initiator composition and drying. In certain embodiments, an initiator composition can be deposited on a solid fuel at a position such that when assembled, the initiator composition forming the igniter is adjacent to the initiator composition deposited on the solid fuel. Having initiator composition on at least a portion of the solid fuel can increase the speed of ignition and the reliability of the ignition process.

The electrically resistive heating element can be connected to electrical conductors. The heating element can be soldered or electrically connected to conductors, such as, Cu conductors or graphite ink traces, disposed on an electrically insulating substrate, such as a polyimide, polyester, or fluoropolymer. The conductors can be disposed between two opposing layers of the electrically insulating material such as flexible or rigid printed circuit board materials. The heating element on which an initiator composition is disposed can be exposed through an opening in the end of ignition assembly 520.

Figure 9A:
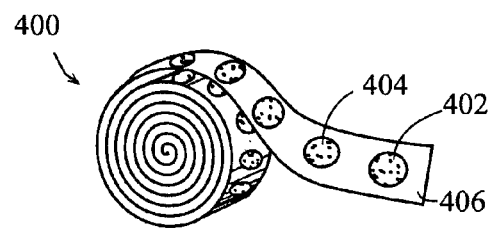
FIGS. 9A-9C show drug supply units for use in drug delivery devices designed for delivering multiple drug doses according to certain embodiments.
Figure 9B:
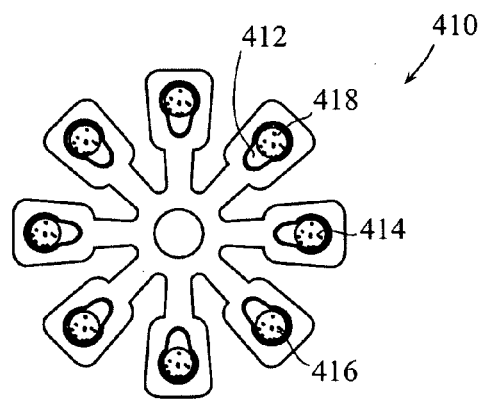
Figure 9C:
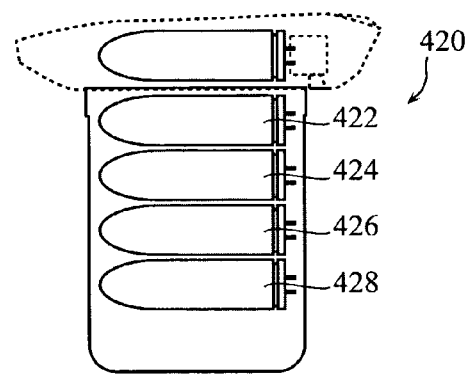

Igniter 520 can be positioned with respect to solid fuel 512 such that sparks produced by initiator composition 522 can be directed toward solid fuel area 512, causing solid fuel 512 to ignite and burn. Initiator composition 522 can be located in any position such that sparks produced by the initiator can cause solid fuel 512 to ignite. The location of initiator composition 522 with respect to solid fuel 512 can determine the direction in which solid fuel 512 burns. For example, initiator composition 522 can be located to cause solid fuel 512 to burn in any direction with respect to the airflow including in the same direction of airflow, opposite the direction of airflow, or normal the direction of airflow. The direction of solid fuel burn with respect to airflow can influence the average particle diameter of particulates comprising the thermally vaporized drug forming the aerosol. For example, in certain embodiments, solid fuel burn opposite the direction of airflow can produce smaller diameter particles than when the direction of solid fuel burn is in the same direction as the airflow. The dynamics of solid fuel burn can be influenced by other parameters such as the spatial and temporal characteristics of the surface temperature, and the extent to which vaporized drug is redeposited on the substrate and/or other surfaces such as a housing in which the drug supply unit is incorporated.

In certain embodiments, thin film drug supply unit 500 can comprise more than one igniter 520 and/or each igniter 520 can comprise more than one initiator composition 522.

In certain embodiments, it can be useful to minimize the amount of initiator composition used, so as to reduce the amount of gas and other reaction products potentially generated by the initiator composition during burn.

In certain embodiments, igniter 520 can comprise a mechanism configured to direct transmitted radiation to an initiator composition capable of absorbing and being heated by the transmitted radiation, to produce sparks. For example, in certain embodiments, the radiation can be infrared, visible, or ultraviolet radiation such as produced by a diode laser, light emitting diode, or flashlamp. Radiation produced by a radiation source can be transmitted through a waveguide such as an optical fiber, and directed to an initiator or the radiation source can be incorporated into the ignition assembly 522 with electrical conductors for connecting to an external power source. The transmission device can include elements such as lenses for focusing the transmitted radiation onto the initiator composition. In certain embodiments, the radiation can be directed to an initiator composition disposed within the heating unit through a window. The transmitted radiation can be directed onto an absorber or a material capable of absorbing the radiation, which can be the initiator composition, or an element on which the initiator composition is disposed. In certain embodiments, the initiator composition can comprise at least one metal such as, but not limited to, zirconium, titanium, or aluminum, and at least one solid oxidizer such as, but not limited to, $MoO_3$, $KClO_4$, CuO, or $WO_3$. The initiator composition can comprise any of those disclosed herein.

As shown in FIG. 10A, thin film drug supply unit 500 can have a spacer 518. Spacer 518 can retain igniter 520. In certain embodiments, spacer 518 can provide a volume or space within the interior of thin film heating unit 500 to collect gases and byproducts generated during the burn of the initiator composition 522 and solid fuel 512. The volume produced by spacer 518 can reduce the internal pressure within thin film drug supply unit 500 upon ignition of the fuel. In certain embodiments, the volume can comprise a porous or fibrous material such as a ceramic, or fiber mat in which the solid matrix component is a small fraction of the unfilled volume. The porous or fibrous material can provide a high surface area on which reaction products generated during the burning of the initiator composition and the solid fuel can be absorbed, adsorbed or reacted. The pressure produced during burn can in part depend on the composition and amount of initiator composition and solid fuel used. In certain embodiments, the spacer can be less than 0.3 inches thick, and in certain embodiments less than 0.2 inches thick. In certain embodiments, the maximum internal pressure during and following burn can be less than 50 psig, in certain embodiments less than 20 psig, in certain embodiments less than 10 psig, and in other certain embodiments less than 6 psig. In certain embodiments, the spacer can be a material capable of maintaining structural and chemical properties at the temperatures produced by the solid fuel burn. In certain embodiments, the spacer can be a material capable of maintaining structure and chemical properties up to a temperature of about 100° C. It can be useful that the material forming the spacer not produce and/or release or produce only a minimal amount of gases and/or reaction products at the temperatures to which it is exposed by the heating unit. In certain embodiments, spacer 518 can comprise a metal, a thermoplastic, such as, for example, but not limitation, a polyimide, fluoropolymer, polyetherimide, polyether ketone, polyether sulfone, polycarbonate, other high temperature resistant thermoplastic polymers, or a thermoset, and which can optionally include a filler.

In certain embodiments, spacer 518 can comprise a thermal insulator such that the spacer does not contribute to the thermal mass of the thin film drug supply unit thereby facilitating heat transfer to the substrate on which drug 514 is disposed. Thermal insulators or impulse absorbing materials such as mats of glass, silica, ceramic, carbon, or high temperature resistant polymer fibers can be used. In certain embodiments, spacer 518 can be a thermal conductor such that the spacer functions as a thermal shunt to control the temperature of the substrate.

Substrates 510, spacer 518 and igniter 520 can be sealed. Sealing can retain any reactants and reaction products released by burning of initiator composition 522 and solid fuel 514, as well as provide a self-contained unit. As shown in FIG. 10A, substrates 510 can be sealed to spacer 518 using an adhesive 516. Adhesive 516 can be a heat sensitive film capable of bonding substrates 510 and spacer 518 upon the application of heat and pressure. In certain embodiments, substrates 510 and spacer 518 can be bonded using an adhesive applied to at least one of the surfaces to be bonded, the parts assembled, and the adhesive cured. The access in spacer 518 into which igniter 520 is inserted can also be sealed using an adhesive. In certain embodiments, other methods for forming a seal can be used such as for example, welding, soldering, or fastening.

In certain embodiments, the elements forming the thin film drug supply unit 500 can be assembled and sealed using thermoplastic or thermoset molding methods such as insert molding and transfer molding.

An appropriate sealing method can, at least in part be determined by the materials forming substrate 510 and spacer 518. In certain embodiments, drug supply unit 500 can be sealed to withstand a maximum pressure of less than 50 psig. In certain embodiments less than 20 psig, and in certain embodiments less than 10 psig. In certain embodiments, the materials used to form the seal can maintain structural integrity at the temperature reached by the article. In certain embodiments, the materials used can exhibit minimal degradation and produce minimal gaseous reaction products at the temperature reached by the heating unit.

Multidose Drug Supply Units In certain embodiments, a drug supply unit can be configured for use in single-use devices or in multi-use devices. FIGS. 9A-9B illustrate certain embodiments of drug supply units configured for use in a drug delivery device designed for multiple uses. As shown in FIG. 9A, a tape 406 in the form of a spool or reel 400 comprises a plurality of drug supply units 402, 404. The plurality of drug supply units 402, 404 can comprise a heating unit on which is disposed a thin film of a drug to be thermally vaporized. Each of the plurality of drug supply units 402, 404 can comprise the same features as those described herein, for example, in FIG. 1A and/or FIG. 1B. In certain embodiments, tape 406 can comprise a plurality of heating units. Each heating unit can comprise a solid fuel, an initiator composition, and a substrate.

Figure 11A:
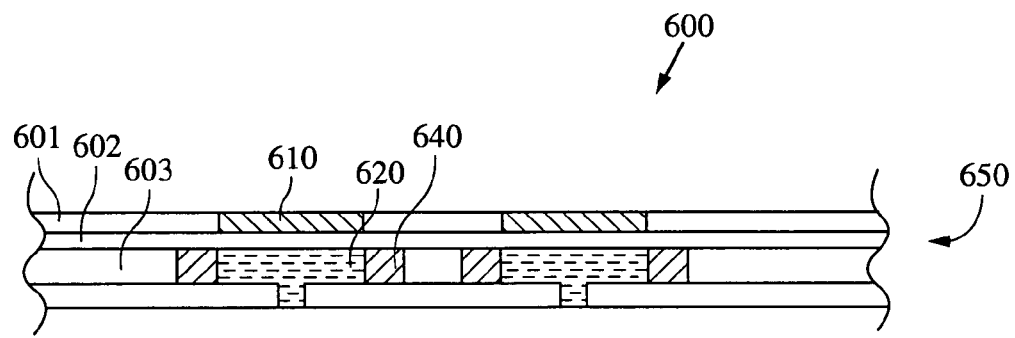
FIGS. 11A-11B show cross-sectional illustrations of thin film drug supply units comprising multiple doses according to certain embodiments.
Figure 11B:
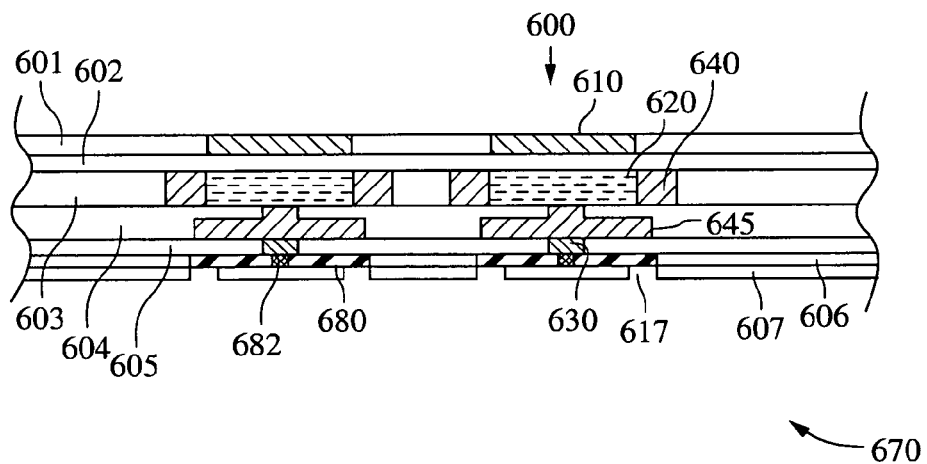
Figure 12:
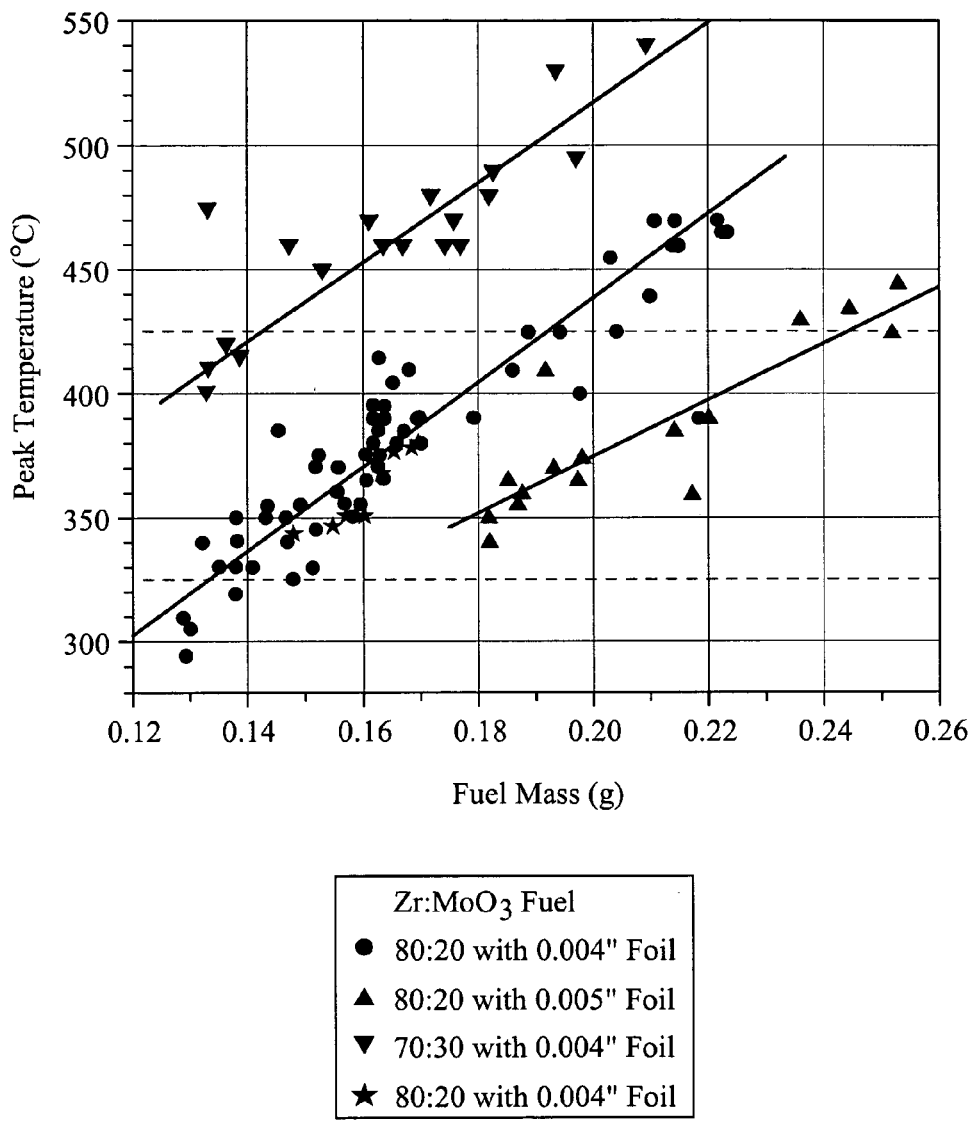
FIG. 12 shows a relationship between the mass of a solid fuel coating and the peak temperature of the exterior surface of a substrate according to certain embodiments.

Embodiments of thin film drug supply units are schematically illustrated in FIGS. 11A-11B. FIGS. 11A-11B illustrate certain embodiments wherein the thin film drug supply units 600 are in the form of a tape 650 comprising multiple layers. As shown in FIG. 11A, tape 650 comprises a first layer 601 having openings in which a drug to be thermally vaporized 610 is disposed. A second layer 602 underlying first layer 601 separates drug 610 from solid fuel 620 disposed within a third layer 603 underlying second layer 602. Second layer 602 can be thermally conductive such that heat can be efficiently transferred from solid fuel 620 to compound 610. In certain embodiments, second layer 602 can be any of the metals described herein. Regions comprising solid fuel 620 underlie regions comprising drug 610. The amount of solid fuel 620 can be an amount sufficient to thermally vaporize drug 610. The dimensions and geometry of the region comprising solid fuel 620 can be any appropriate dimension. In certain embodiments, third layer 603 can comprise a volume 640 to collect reaction products generated during burn of solid fuel 620 and thereby reduce the pressure within thin film drug supply unit 600. In certain embodiments (not shown), volume 640 can comprise a material capable of absorbing, adsorbing or reacting with reaction products produced during burning of the solid, such as a porous ceramic or fibrous material. Third layer 603 can comprise a material in which the mechanical properties are substantially maintained and which will not appreciably chemically degrade up to the temperatures reached by the drug supply unit 600. In certain embodiments, third layer 603 can comprise a metal or a polymer such as polyimide, fluoropolymer, polyetherimide, polyether ketone, polyether sulfone, polycarbonate, or other high temperature resistance polymers.

In certain embodiments, tape 650 can comprise an upper and lower layer (not shown) configured to physically and/or environmentally protect compound 610 and solid fuel 620. The upper and/or lower protective layers can comprise, for example, a metal foil, a polymer, or can comprise a multilayer comprising metal foil and polymers. In certain embodiments, protective layers can exhibit low permeability to oxygen, moisture, and/or corrosive gases. All or portions of a protective layer can be removed prior to use to expose compound 610 and solid fuel 620. To vaporize compound 610, solid fuel 620 can be ignited by energy from an external source (not shown) to generate heat that can be conducted through second layer 602 to thermally vaporize compound 610. Examples of initiators include those discussed herein such as, but not limited to, sparks or electrical resistance heating. Use of a protective layer can facilitate use of drug 610 in the form of a powder or liquid.

FIG. 11B shows a cross-sectional view of a tape 670 comprising thin film drug supply units 600, which in addition to the elements recited for FIG. 11A, further comprise an initiator composition 630. Tape 670 has multiple layers including first layer 601 within which compound 610 is disposed, second layer 602 separating first layer 601 and third layer 603. Layer 603 retains solid fuel 620 and in certain embodiments, a volume 640. Openings in a fourth layer 604 define a gap separating solid fuel 620 disposed in third layer 603, and initiator composition 630 disposed within regions of a fifth layer 605. Initiator composition 630 can comprise any of the initiator compositions disclosed herein. Initiator 630 can adjoin an electrically resistive heating element 682 disposed within a sixth layer 606 and connected to electrical conductors 680 also disposed within sixth layer 606. As shown, a seventh layer 607 overlies sixth layer 606 and comprises openings 617 to facilitate electrical connection between electrical conductors 680 and a power source (not shown).

In an exemplary operation, tape 670 can be advanced to locate at least one region comprising drug 610 within an airway (not shown) and to connect respective electrical contacts 680, with a power source (not shown). Upon activation of the power source, the electrical current can heat resistive element 682 to ignite initiator composition 630 and produce sparks. Sparks directed across gap 645 can ignite solid fuel 620. Heat generated by the ignition of solid fuel 620 can be conducted through second layer 602 thermally vaporizing compound 610 to form an aerosol comprising drug 610 within the airway.

Certain embodiments of another drug supply article configured for the delivery of multiple doses is illustrated in FIG. 9B. FIG. 9B shows a plurality of individual drug-supply units provided on a card 410. Drug supply units 412, 414, 416, each consist of a solid fuel contained between a backing member and a substrate, such as substrate 418 on unit 412. A film of drug can be coated onto substrate 418. Card 410 can be loaded into a suitable device configured to ignite at least one drug supply unit at a time. Ignition can be, for example by sparks, as disclosed herein. To provide a subsequent dose, card 410 can be rotated to advance a fresh drug supply unit.

FIG. 9C shows a cartridge 420 containing a plurality of cylindrically-shaped drug supply units 422, 424, 426, 428. The drug supply units can be as described herein, and comprise a solid fuel contained within an enclosure comprising a substrate. The external surface of the substrate can be coated with a film of drug. Each drug supply unit can be successively advanced into position in a drug delivery device chamber for ignition of the solid fuel, vaporization of the drug, and administration to a user.

Drug Delivery Devices

Certain embodiments include drug delivery devices comprising a housing defining an airway, a heating unit as disclosed herein, a drug disposed on a portion of the exterior surface of a substrate of the heating unit, wherein the portion of the exterior surface comprising the drug is configured to be disposed within the airway, and an initiator configured to ignite the solid fuel. Drug delivery devices can incorporate the heating units and drug supply units disclosed herein. The drug delivery device can comprise a housing defining an airway. The housing can define an airway having any appropriate shape or dimensions and can comprise at least one inlet and at least one outlet. The dimensions of an airway can at least in part be determined by the volume of air that can be inhaled through the mouth or the nostrils by a user in a single inhalation, the intended rate of airflow through the airway, and/or the intended airflow velocity at the surface of the substrate that is coupled to the airway and on which a drug is disposed. In certain embodiments, airflow can be generated by a patient inhaling with the mouth on the outlet of the airway, and/or by inhaling with the nostrils on the outlet of the airway. In certain embodiments, airflow can be generated by injecting air or a gas into the inlet such as for example, by mechanically compressing a flexible container filled with air and/or gas, or by releasing pressurized air and/or gas into the inlet of the airway. Generating an airflow by injecting air and/or gas into the airway can be useful in drug delivery devices intended for topical administration of an aerosol comprising a drug.

In certain embodiments, a housing can be dimensioned to provide an airflow velocity through the airway sufficient to produce an aerosol of a drug during thermal vaporization. In certain embodiments, the airflow velocity can be at least 1 m/sec in the vicinity of the substrate on which the drug is disposed.

In certain embodiments, a housing can be dimensioned to provide a certain airflow rate through the airway. In certain embodiments, the airflow rate through the airway can range from 10 L/min to 120 L/min In certain embodiments, an airflow rate ranging from 10 L/min to 120 L/min can be produced during inhalation by a user when the outlet exhibits a cross-sectional area ranging from 0.1 $cm^2$ to 20 $cm^2$. In certain embodiments, the cross-sectional area of the outlet can range from 0.5 $cm^2$ to 5 $cm^2$, and in certain embodiments, from 1 $cm^2$ to 2 $cm^2$.

In certain embodiments, an airway can comprise one or more airflow control valves to control the airflow rate and airflow velocity in airway. In certain embodiments, an airflow control valve can comprise, but is not limited to, at least one valve such as an umbrella valve, a reed valve, a flapper valve, or a flapping valve that bends in response to a pressure differential, and the like. In certain embodiments, an airflow control valve can be located at the outlet of the airway, at the inlet of the airway, within the airway, and/or can be incorporated into the walls of housing defining the airway. In certain embodiments, an airflow control valve can be actively controlled, for example can be activated electronically such that a signal provided by a transducer located within the airway can control the position of the valve; or passively controlled, such as, for example, by a pressure differential between the airway and the exterior of the device.

Figure 8:
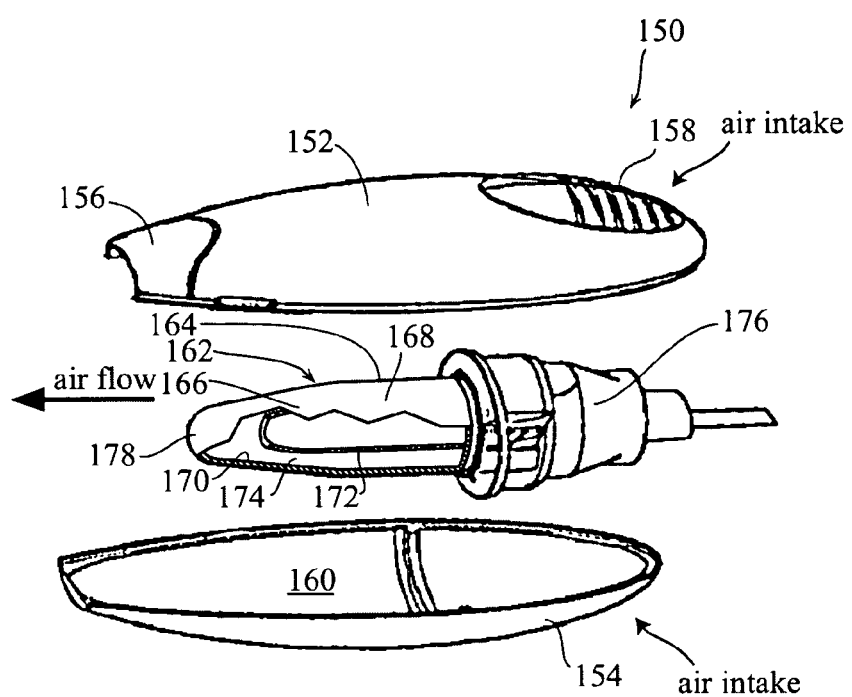

Certain embodiments of drug delivery devices configured for inhalation delivery of thermal vapor generated from a drug supply unit are illustrated in FIG. 8. Inhalation device 150 has an upper external housing member 152 and a lower external housing member 154 that snap fit together. The downstream end of each housing member can be gently tapered for insertion into a user's mouth, as shown on upper housing member 152 at downstream end 156. The upstream end of the upper and lower housing members can be slotted 158, as shown in the upper housing member 152, to provide for air intake when a user inhales. When fitted together, upper and lower housing members 152, 154 define a chamber 160. A drug supply unit 162 can be positioned within chamber 160. Drug supply unit 162 comprises a tapered, substantially cylindrical substrate 164 having an external surface 168 on which is disposed a film 166 of drug. The interior surface 170 of the substrate and a portion of the inner, cylindrical backing member 172 are shown in the cut-away section of drug supply unit 162. Solid fuel 174 is located within the annular shell region defined by backing member 172 and interior substrate surface 170. At least one initiator composition can be provided for the heating unit, and in certain embodiments as shown in FIG. 8, an initiator composition can be positioned (not shown) in the upstream end of the device where the air intake occurs. The initiator composition can be configured to ignite solid fuel 174 by the application of electrical current to an ohmic heating element connected to a battery (not shown) located in end piece 176. Activation of the initiator composition can produce sparks that are confined within a space defined by backing member 172 and thus can be directed toward the downstream end of the drug supply unit indicated at point 178. Sparks reaching the tapered nose portion at downstream end 178 can ignite solid fuel 174. Solid fuel 174 then burns in a downstream-to-upstream direction, i.e. from point 178 toward the air intake end of the device at point 158, generating a wave of heat in the downstream-to-upstream direction that vaporizes drug film 166 disposed on exterior substrate surface 168. Thus, the direction of solid fuel burn and the direction of thermal drug vapor generation are opposite the direction of airflow through chamber 160 of the inhalation device.

Methods for Producing and Using Aerosols

Certain embodiments include methods of producing an aerosol of a compound using the heating units, drug supply units, and drug delivery devices disclosed herein. In certain embodiments, the aerosol produced by an apparatus can comprise a therapeutically effective amount of a drug. The temporal and spatial characteristics of the heat applied to thermally vaporize the compound disposed on the substrate and the air flow rate can be selected to produce an aerosol comprising a drug having certain characteristics. For example, for intrapulmonary delivery it is known that aerosol particles having a mean mass aerodynamic diameter ranging from 0.01 μm to 0.1 μm and ranging from 1 μm to 3.5 μm can facilitate efficient transfer of drugs from alveoli to the systemic circulation. In applications wherein the aerosol is applied topically, the aerosol can have the same or different characteristics.

Certain embodiments include methods for producing an aerosol comprising: (i) providing an airflow over a drug disposed on a portion of an exterior surface of a substrate forming a drug supply unit, wherein the drug supply unit comprises a heating unit as disclosed herein and the drug disposed on a portion of the exterior surface of the substrate, wherein the portion of the exterior surface comprising the drug is disposed within the airway; and an initiator composition configured to ignite the solid chemical fuel; and (ii) thermally vaporizing and condensing the drug to form an aerosol of the drug in the airway. In certain embodiments, the drug is disposed on the surface of the substrate as a thin film.

Certain embodiments include methods of treating a disease in a patient in need of such treatment comprising administering to the patient an aerosol comprising a therapeutically effective amount of a drug, wherein the aerosol is produced by the methods and devices disclosed herein. The aerosol can be administered by inhalation through the mouth, by nasal ingestion, and/or by topical application.

Other embodiments will be apparent to those skilled in the art from consideration and practice of the invention disclosed herein. It is intended that the specification and examples be considered as exemplary only.

EXAMPLES

In the examples below, the following abbreviations have the following meanings. If an abbreviation is not defined, it has its generally accepted meaning.

wt % weight percent
psig pounds per square inch, gauge
DI deionized
mL milliliters
msec milliseconds
L/min liters per minute
μm micrometer

Example 1

Preparation of Solid Fuel with LAPONITE

The following procedure was used to prepare solid fuel coatings comprising 76.16% Zr:19.04% $MoO_3$:4.8% LAPONITE® RDS.

To prepare wet Zirconium (Zr), the as-obtained suspension of Zr in DI water (Chemetall, Germany) was agitated on a roto-mixer for 30 minutes. Ten to 40 mL of the wet Zr was dispensed into a 50 mL centrifuge tube and centrifuged (Sorvall 6200RT) for 30 minutes at 3,200 rpm. The DI water was removed to leave a wet Zr pellet.

To prepare a 15% LAPONITE® RDS solution, 85 grams of DI water was added to a beaker. While stirring, 15 grams of LAPONITE® RDS (Southern Clay Products, Gonzalez, Tex.) was added, and the suspension stirred for 30 minutes.

The reactant slurry was prepared by first removing the wet Zr pellet as previously prepared from the centrifuge tube and placed in a beaker. Upon weighing the wet Zr pellet, the weight of dry Zr was determined from the following equation: Dry Zr (g)=0.8234 (Wet Zr (g))−0.1059.

The amount of molybdenum trioxide to provide a 80:20 ratio of Zr to $MoO_3$ was then determined, e.g, $MoO_3$=Dry Zr (g)/4, and the appropriate amount of $MoO_3$ powder (Accumet, N.Y.) was added to the beaker containing the wet Zr to produce a wet Zr:$MoO_3$ slurry. The amount of LAPONITE® RDS to obtain a final weight percent ratio of dry components of 76.16% Zr:19.04% $MoO_3$:4.80% LAPONITE® RDS was determined Excess water to obtain a reactant slurry comprising 40% DI water was added to the wet Zr and $MoO_3$ slurry. The reactant slurry was mixed for 5 minutes using an IKA Ultra-Turrax mixing motor with a S25N-8G dispersing head (setting 4). The amount of 15% LAPONITE® RDS previously determined was then added to the reactant slurry, and mixed for an additional 5 minutes using the IKA Ultra-Turrax mixer. The reactant slurry was transferred to a syringe and stored for at least 30 minutes prior to coating.

The Zr:$MoO_3$:LAPONITE® RDS reactant slurry was then coated onto stainless steel foils. Stainless steel foils were first cleaned by sonication for 5 minutes in a 3.2% by solution of Ridoline 298 in DI water at 60° C. Stainless steel foils were masked with 0.215 inch wide MYLAR® such that the center portion of each 0.004 inch thick 304 stainless steel foil was exposed. The foils were placed on a vacuum chuck having 0.008 inch thick shims at the edges. Two (2) mL of the reactant slurry was placed at one edge of the foil. Using a Sheen Auto-Draw Automatic Film Applicator 1137 (Sheen Instruments) the reactant slurry was coated onto the foils by drawing a #12 coating rod at an auto-draw coating speed of up to 50 mm/sec across the surface of the foils to deposit approximately an 0.006 inch thick layer of the Zr:$MoO_3$:LAPONITE® RDS reactant slurry. The coated foils were then placed in a 40° C. forced-air convection oven and dried for at least 2 hours. The masks were then removed from the foils to leave a coating of solid fuel on the center section of each foil.

The solid fuel coatings comprising LAPONITE® RDS adhered to the stainless steel foil surface and maintained physical integrity following mechanical and environmental testing including temperature cycling (−25° C.⇋40° C.), accelerated humidity exposure (40° C./75% RH), drop testing, impact testing, and flexure testing.

Example 2

Measurement of Internal Pressure

Thin film heating units were used to measure the peak internal pressure and the peak temperature of the exterior surface of the substrate following ignition of the solid fuel.

The thin film heating units were substantially as described in Example 9 below and as illustrated in FIGS. 10A and 10B. Two, 2×2 square inch, 0.004 inch thick 304 stainless steel foils formed the substrates. A solid fuel comprising 76.16 wt % Zr, 19.04% $MoO_3$, 4.8% LAPONITE® RDS and water was coated onto the interior surface of the stainless steel substrates. The thickness of the solid fuel layer was 0.0018±0.0003 inches. The layer of solid fuel covered an area of 1.69 $in^2$ and after drying, the weight of the solid fuel disposed on the interior surface of each substrate was 0.165 to 0.190 grams. The spacer comprised a 0.24 inch thick section of polycarbonate (Makrolon). The ignition assembly comprised a FR-4 printed circuit board having a 0.03 inch diameter opening at the end to be disposed within an enclosure defined by the spacer and the substrates. A 0.0008 inch diameter Nichrome wire was soldered to electrical conductors on the printed circuit board and positioned across the opening. An initiator composition comprising 26.5% Al, 51.4% $MoO_3$, 7.7% B and 14.3% VITON® A500 weight percent was deposited onto the Nichrome wire and dried.

To assemble the thin film drug supply unit, the Nichrome wire comprising the initiator composition was positioned at one end of the solid fuel area. A bead of epoxy (Epo-Tek 353 ND, Epoxy Technology) was applied to both surfaces of the spacer, and the spacer, substrates and the ignition assembly positioned and compressed. The epoxy was cured at a temperature of 100° C. for 3 hours.

To ignite the solid fuel, a 0.4 amp current was applied to the electrical conductors connected to the Nichrome wire.

The peak internal pressure was measured using a pressure sensor (Motorola, MPXA4250A) The external surface temperature was measured using IR camera (FLIR, Therma CAM SC3000).

Example 3

Thermal Images of Heating Unit

A solid fuel consisting of a mixture of zirconium (40.6 wt %), $MoO_3$ (21.9 wt %), and $KClO_3$ (1.9 wt %), nitrocellulose (0.6 wt %), and diatomaceous earth (35 wt %) was prepared. The solid fuel was placed in a 0.030-inch gap between a stainless steel substrate (0.015 inch wall thickness) and a stainless steel backing member (0.015 inch wall thickness). The diameter of the substrate was 9/16 inch. The fuel was ignited, and thermal images of the heating unit were taken as a function of time after ignition. The results are shown in FIGS. 4A-4F.

Example 4

Thermal Images of Heating Units to Evaluate Surface Temperature Uniformity

A. A solid fuel consisting of a mixture of zirconium (53.8 wt %), $MoO_3$ (23.1 wt %), and $KClO_3$ (2.3 wt %), nitrocellulose (0.8 wt %) and diatomaceous earth (20 wt %), was prepared. The solid fuel mixture was placed in a 0.030-inch gap between a stainless steel substrate (0.015 inch wall thickness) and a stainless steel backing member (0.015 inch wall thickness). The diameter of the substrate was 9/16 inch. The fuel was ignited, and a thermal image of the heating unit was taken 400 milliseconds after ignition. The image is shown in FIG. 5A.

B. A solid fuel consisting of a mixture of zirconium (46.9 wt %), $MoO_3$ (25.2 wt %), $KClO_3$ (2.2 wt %), nitrocellulose (0.7 wt %), and diatomaceous earth (25.0 wt %) was prepared. The solid fuel was placed in a 0.030-inch gap between a stainless steel substrate (0.015 inch wall thickness) and a stainless steel backing member (0.015 inch wall thickness). The diameter of the substrate was 9/16 inch. The fuel was ignited, and a thermal image of the heating unit was taken 400 milliseconds after ignition. The image is shown in FIG. 5B.

Example 5

Exemplary Heating Unit

A solid fuel consisting of a mixture of zirconium (46.9 wt %), $MoO_3$ (25.2 wt %), and $KClO_3$ (2.2 wt %), grain size 100-325 mesh, along with nitrocellulose (0.7 wt %) and diatomaceous earth (25.0 wt %) was prepared. The solid fuel was placed in a 0.030-inch gap between a stainless steel substrate (0.015 inch wall thickness) and a stainless steel backing member (0.015 inch wall thickness). The diameter of the substrate was 9/16 inch. The solid fuel was remotely ignited from the tip of the heating unit. During and after burn, the pressure in the cylindrical substrate was measured as described herein. The burn propagation speed and the surface temperature uniformity were evaluated by infrared imaging.

The internal pressure increased to 150 psig during the reaction period of 0.3 seconds. The residual pressure was under 60 psig. The burn propagation speed was 13 cm/sec. With respect to surface temperature uniformity, no obvious cold spots were observed.

Example 6

Heating Unit Embodiment

A solid fuel consisting of a mixture of zirconium (69.3 wt %) and $MoO_3$ (29.7 wt %), grain size 100-325 mesh, along with nitrocellulose (1.0 wt %) was prepared. The solid fuel mixture was placed in a 0.020-inch gap between a stainless steel substrate (0.020 inch wall thickness) and a stainless steel backing member (0.020 inch wall thickness). The outside of the backing member was coated with initiator to increase burn propagation speed. The primary fuel was remotely ignited from the tip of the heating unit. During and after burn, the pressure in the cylindrical substrate was measured as described herein. The burn propagation speed and the surface temperature uniformity were evaluated by infrared imaging.

The internal pressure increased to 200 psig during the reaction period of 0.25 seconds. The residual pressure was under 60 psig. The burn propagation speed was 15 cm/sec. With respect to surface temperature uniformity, no obvious cold spots were observed.

Example 7

Heating Unit Embodiment

A solid fuel consisting of a mixture of aluminum (49.5 wt %) and $MoO_3$ (49.5 wt %), grain size 100-325 mesh, along with nitrocellulose (1.0 wt %) was prepared. The solid fuel mixture was placed in a 0.020-inch gap between a stainless steel substrate (0.020 inch wall thickness) and a stainless steel backing member (0.020 inch wall thickness). The primary fuel was directly ignited near the plug. During and after burn, the pressure in the cylindrical substrate was measured as described herein. The surface temperature uniformity was evaluated by infrared imaging.

The internal pressure increased to 300 psig during the reaction period of less than 5 milliseconds. The residual pressure was under 60 psig. The exterior surface expanse was uniformly heated, with between 5-10 percent of the surface being 50° C. to 100° C. cooler than the rest of the expanse.

Example 8

Wet Processing for Zirconium Fuel Slurry

The following procedure was used to prepare fuel compositions comprising Zr and $MoO_3$ for a thin film drug supply unit. Wet Zr particles, 46.7 wt %, having a 2 μm to 3 μm particle size were obtained from Chemetall, GmbH, Germany. The Zr particles were rinsed with DI water, following which the excess water was decanted. DI water, 5.1 wt %, was added to the Zr and the mixture centrifuged. Excess water was decanted. Dry $MoO_3$, 20 wt %, (Climax Molybdenum Co., AZ) and DI water was then added to the washed Zr, and the mixture homogenized for 2 minutes with a high shear mixer (IKA, Germany). A 15% aqueous solution of LAPONITE® RDS, 2.5 wt %, (Southern Clay Products, Inc., Texas) was added and the mixture homogenized with a high shear mixer for an additional 5 minutes. The Zr:$MoO_3$ solid fuel slurry was transferred to a syringe or holding vessel for subsequent coating. The wet Zr included 8.5 wt % water and the LAPONITE® RDS gel included 14 wt % water. The weight percents represent the percent weight of the total wet composition.

Example 9

Thin Film Drug Supply Unit Embodiment

A thin film drug supply unit according to FIGS. 10A-10B was fabricated and the performance evaluated. Two, 2×2 square inch, 0.004 inch thick 304 stainless steel foils formed the substrates. A solid fuel comprising 76.16 wt % Zr and 19.04% $MoO_3$ and 4.8% LAPONITE® RDS and water was coated onto the interior surface of the stainless steel substrates. The thickness of the solid fuel layer was 0.0018±0.0003 inches. The layer of solid fuel covered an area of 1.69 $in^2$ and after drying, the weight of the solid fuel disposed on the interior surface of each substrate was 0.165 to 0.190 grams. An ~6 μm thick thin film of a drug was deposited onto a 1.21 $in^2$ area of the exterior substrate surfaces using spray coating. The drug was dissolved in a 15 mg/ml solution of isopropanol or acetone to facilitate processing. The thin film of drug was dried at ambient conditions and 1.5 mg to 3.0 mg of drug was deposited on the exterior surface of each substrate. The spacer comprised a 0.24 inch thick section of polycarbonate (Makronlon). The ignition assembly comprised a FR-4 printed circuit board having a 0.03 inch diameter opening at the end to be disposed within an enclosure defined by the spacer and the substrates. A 0.0008 inch diameter Nichrome wire was soldered to electrical conductors on the printed circuit board and positioned across the opening. An initiator composition comprising 26.5% Al, 51.4% $MoO_3$, 7.7% B and 14.3% VITON® A500 weight percent was deposited onto the Nichrome wire and dried.

To assemble the thin film drug supply unit, the Nichrome wire comprising the initiator composition was positioned at one end of the solid fuel area. A bead of epoxy (Epo-Tek 353

ND, Epoxy Technology) was applied to both surfaces of the spacer, and the spacer, substrates and the ignition assembly positioned and compressed. The epoxy was cured at a temperature of 100° C. for 3 hours.

To ignite the solid fuel, a 0.4 Amp current was applied to the electrical conductors connected to the Nichrome wire.

The airflow in the airway used for the measurements ranged from 14 L/min to 28 L/min corresponding to an airflow velocity of 1.5 m/sec and 3 m/sec, respectively.

Measurements on such drug supply units demonstrated that the exterior surface of the substrate reached temperatures in excess of 400° C. in less than 150 milliseconds following activation of the initiator at which time the drug was completely thermally vaporized. The maximum pressure within the enclosure was less than 10 psig. In separate measurements, it was demonstrated that the enclosure was able to withstand a static pressure in excess of 60 psig at room temperature. The burn propagation speed across the expanse of solid fuel was measured to be 25 cm/sec. The particulates forming the aerosol comprised greater than 95% of the drug, and greater than 90% of the drug originally deposited on the substrates formed the aerosol.

Example 10

Measurement of Aerosol Purity and Yield

Drug supply units substantially as described in Example 9 and illustrated in FIGS. 10A and 10B were used to measure the percent yield and percent purity of aerosols.

Two, 2×2 square inch, 0.004 inch thick 304 stainless steel foils formed the substrates. A solid fuel comprising 76.16 wt % Zr, 19.04% $MoO_3$, 4.8% LAPONITE® RDS and water was coated onto the interior surface of the stainless steel substrates. The thickness of the solid fuel layer was 0.0018±0.0003 inches. The layer of solid fuel covered an area of 1.69 $in^2$ and after drying, the weight of the solid fuel disposed on the interior surface of each substrate was 0.165 to 0.190 grams. An ~6 μm thick thin film of a drug was deposited onto a 1.21 $in^2$ area of the exterior substrate surfaces using spray coating. The drug was dissolved in a 15 mg/ml solution of isopropanol or acetone to facilitate processing. The thin film of drug was dried at ambient conditions and 1.5 mg to 3.0 mg of drug was deposited on the exterior surface of each substrate. The spacer comprised a 0.24 inch section of polycarbonate (Makronlon). The ignition assembly comprised a FR-4 printed circuit board having a 0.03 inch diameter opening at the end to be disposed within an enclosure defined by the spacer and the substrates. A 0.0008 inch diameter Nichrome wire was soldered to electrical conductors on the printed circuit board and positioned across the opening. An initiator composition comprising 26.5% Al, 51.4% $MoO_3$, 7.7% B and 14.3% VITON® A500 weight percent was deposited onto the Nichrome wire and dried.

To assemble the thin film drug supply unit, the Nichrome wire comprising the initiator composition was positioned at one end of the solid fuel area. A bead of epoxy (Epo-Tek 353 ND, Epoxy Technology) was applied to both surfaces of the spacer, and the spacer, substrates and the ignition assembly positioned and compressed. The epoxy was cured at a temperature of 100° C. for 3 hours.

To ignite the solid fuel, a 0.4 Amp current was applied to the electrical conductors connected to the Nichrome wire.

The airflow in the airway used for the measurements ranged from 14 L/min to 28 L/min corresponding to an airflow velocity of 1.5 m/sec and 3 m/sec, respectively.

After volatilization, the aerosol was captured on a mat for quantification of yield and analysis of purity. The quantity of material recovered on the mat was used to determine a percent yield, based on the mass of drug coated onto the substrate. Any material deposited on the housing or the remaining on the substrate was also recovered and quantified to determine a percent total recovery ((mass of drug on the mat+mass of drug remaining on substrate and housing)/mass of drug coated onto substrate). For compounds without UV absorption GC/MS or LC/MS was used to quantify the recovery.

The percent purity was determined using HPLC UV absorption at 250 nm. However, as one of skill in the art recognizes, the purity of a drug-containing aerosol may be determined using a number of different methods. It should be noted that when the term "purity" is used, it refers to the percentage of aerosol minus the percent byproduct produced in its formation. Byproducts for example, are those unwanted products produced during vaporization. For example, byproducts include thermal degradation products as well as any unwanted metabolites of the active compound or compounds. Examples of suitable methods for determining aerosol purity are described in Sekine et al., *Journal of Forensic Science* 32:1271-1280 (1987) and in Martin et al., *Journal of Analytic Toxicology* 13:158-162 (1989).

One suitable method involves the use of a trap. In this method, the aerosol is collected in a trap in order to determine the percent or fraction of byproduct. Any suitable trap may be used. Suitable traps include mats, glass wool, impingers, solvent traps, cold traps, and the like. Mats are often most desirable. The trap is then typically extracted with a solvent, e.g. acetonitrile, and the extract subjected to analysis by any of a variety of analytical methods known in the art, for example, gas, liquid, and high performance liquid chromatography particularly useful.

The gas or liquid chromatography method typically includes a detector system, such as a mass spectrometry detector or an ultraviolet absorption detector. Ideally, the detector system allows determination of the quantity of the components of the drug composition and of the byproduct, by weight. This is achieved in practice by measuring the signal obtained upon analysis of one or more known mass(es) of components of the drug composition or byproduct (standards) and then comparing the signal obtained upon analysis of the aerosol to that obtained upon analysis of the standard(s), an approach well known in the art.

In many cases, the structure of a byproduct may not be known or a standard for it may not be available. In such cases, one may calculate the weight fraction of the byproduct by assuming it has an identical response coefficient (e.g. for ultraviolet absorption detection, identical extinction coefficient) to the drug component or components in the drug composition. When conducting such analysis, byproducts present in less than a very small fraction of the drug compound, e.g. less than 0.1% or 0.03% of the drug compound, are typically excluded. Because of the frequent necessity to assume an identical response coefficient between drug and byproduct in calculating a weight percentage of byproduct, it is often more desirable to use an analytical approach in which such an assumption has a high probability of validity. In this respect, high performance liquid chromatography with detection by absorption of ultraviolet light at 225 nm is typically desirable. UV absorption at 250 nm may be used for detection of compounds in cases where the compound absorbs more strongly at 250 nm or for other reasons one skilled in the art would consider detection at 250 nm the most appropriate means of estimating purity by weight using HPLC analysis.

In certain cases where analysis of the drug by UV are not viable, other analytical tools such as GC/MS or LC/MS may be used to determine purity.

Example 11

Preparation of Heating Unit with Percussion Ignition

The following procedure was used to prepare solid fuel coatings comprising 76.16% Zr:19.04% $MoO_3$:4.8% LAPONITE® RDS.

To prepare wet Zirconium (Zr), the as-obtained suspension of Zr in DI water (Chemetall, Germany) was agitated on a roto-mixer for 30 minutes. Ten to 40 mL of the wet Zr was dispensed into a 50 mL centrifuge tube and centrifuged (Sorvall 6200RT) for 30 minutes at 3,200 rpm. The DI water was removed to leave a wet Zr pellet.

To prepare a 15% LAPONITE® RDS solution, 85 grams of DI water was added to a beaker. While stirring, 15 grams of LAPONITE® RDS (Southern Clay Products, Gonzalez, Tex.) was added, and the suspension stirred for 30 minutes.

The reactant slurry was prepared by first removing the wet Zr pellet as previously prepared from the centrifuge tube and placed in a beaker. Upon weighing the wet Zr pellet, the weight of dry Zr was determined from the following equation: Dry Zr (g)=0.8234 (Wet Zr (g))−0.1059.

The amount of molybdenum trioxide to provide a 80:20 ratio of Zr to $MoO_3$ was then determined, e.g, $MoO_3$=Dry Zr (g)/4, and the appropriate amount of $MoO_3$ powder (Accumet, N.Y.) was added to the beaker containing the wet Zr to produce a wet Zr:$MoO_3$ slurry. The amount of LAPONITE® RDS to obtain a final weight percent ratio of dry components of 76.16% Zr:19.04% $MoO_3$:4.80% LAPONITE® RDS was determined Excess water to obtain a reactant slurry comprising 40% DI water was added to the wet Zr and $MoO_3$ slurry. The reactant slurry was mixed for 5 minutes using an IKA Ultra-Turrax mixing motor with a S25N-8G dispersing head (setting 4). The amount of 15% LAPONITE® RDS previously determined was then added to the reactant slurry, and mixed for an additional 5 minutes using the IKA Ultra-Turrax mixer. The reactant slurry was transferred to a syringe and stored for at least 30 minutes prior to coating.

The Zr:$MoO_3$:LAPONITE® RDS reactant slurry was then coated onto stainless steel foils. Stainless steel foils were first cleaned by sonication for 5 minutes in a 3.2% by solution of Ridoline 298 in DI water at 60° C. Stainless steel foils were masked with 0.215 inch wide MYLAR® such that the center portion of each 0.004 inch thick 304 stainless steel foil was exposed. The foils were placed on a vacuum chuck having 0.008 inch thick shims at the edges. Two (2) mL of the reactant slurry was placed at one edge of the foil. Using a Sheen Auto-Draw Automatic Film Applicator 1137 (Sheen Instruments) the reactant slurry was coated onto the foils by drawing a #12 coating rod at an auto-draw coating speed of up to 50 mm/sec across the surface of the foils to deposit approximately an 0.006 inch thick layer of the Zr:$MoO_3$:LAPONITE® RDS reactant slurry. The coated foils were then placed in a 40° C. forced-air convection oven and dried for at least 2 hours. The masks were then removed from the foils to leave a coating of solid fuel on the center section of each foil.

The ignition assembly comprised a thin stainless steel wire (wire anvil) dip coated ¼ an inch in an initiator composition comprising 620 parts by weight of titanium (size less than 20 μm), 100 part by weight of potassium chlorate, 180 parts by weight red phosphorus, 100 parts by weight sodium chlorate, and 620 parts by weight water with 2% polyvinyl alcohol binder. The coated wire was then dried at about 40-50° C. for 1 hour. The dried coated wire was placed into an ignition tube (soft walled aluminum tube 0.003 inch wall thickness) and one end was crimped to hold the wire in place.

To assemble the heating unit, the ignition tube was place between two fuel coated foil substrates (fuel chips) with the open end of the ignition tube aligned with the edge of the fuel coatings on the fuel chips. The fuel chips were sealed with aluminum adhesive tape.

To ignite the solid fuel, the ignition tube was struck with a brass rod. Both fuel chips in the heating unit readily ignited.

Example 12

An Embodiment of a Device with Multi-Heating Units using Optical Ignition

The following procedure was used to prepare solid fuel coatings comprising 76.16% Zr:19.04% $MoO_3$:4.8% LAPONITE® RDS.

To prepare wet Zirconium (Zr), the as-obtained suspension of Zr in DI water (Chemetall, Germany) was agitated on a roto-mixer for 30 minutes. Ten to 40 mL of the wet Zr was dispensed into a 50 mL centrifuge tube and centrifuged (Sorvall 6200RT) for 30 minutes at 3,200 rpm. The DI water was removed to leave a wet Zr pellet.

To prepare a 15% LAPONITE® RDS solution, 85 grams of DI water was added to a beaker. While stiffing, 15 grams of LAPONITE® RDS (Southern Clay Products, Gonzalez, Tex.) was added, and the suspension stirred for 30 minutes.

The reactant slurry was prepared by first removing the wet Zr pellet as previously prepared from the centrifuge tube and placed in a beaker. Upon weighing the wet Zr pellet, the weight of dry Zr was determined from the following equation: Dry Zr (g)=0.8234 (Wet Zr (g))−0.1059.

The amount of molybdenum trioxide to provide a 80:20 ratio of Zr to $MoO_3$ was then determined, e.g, $MoO_3$=Dry Zr (g)/4, and the appropriate amount of $MoO_3$ powder (Accumet, N.Y.) was added to the beaker containing the wet Zr to produce a wet Zr:$MoO_3$ slurry. The amount of LAPONITE® RDS to obtain a final weight percent ratio of dry components of 76.16% Zr:19.04% $MoO_3$:4.80% LAPONITE® RDS was determined Excess water to obtain a reactant slurry comprising 40% DI water was added to the wet Zr and $MoO_3$ slurry. The reactant slurry was mixed for 5 minutes using an IKA Ultra-Turrax mixing motor with a S25N-8G dispersing head (setting 4). The amount of 15% LAPONITE® RDS previously determined was then added to the reactant slurry, and mixed for an additional 5 minutes using the IKA Ultra-Turrax mixer. The reactant slurry was transferred to a syringe and stored for at least 30 minutes prior to coating.

The Zr:$MoO_3$:LAPONITE® RDS reactant slurry was then coated onto 3 inch circular stainless steel foils. Stainless steel foils were first cleaned by sonication for 5 minutes in a 3.2% by solution of Ridoline 298 in DI water at 60° C. Stainless steel foils 91 were masked with a 3 inch round sheet of MYLAR® with twelve 0.25 inch by 0.5 inch spaces cut into the MYLAR® so that twelve rectangles of 0.25 by 0.5 inches of 0.004 inch thick 304 stainless steel foil was exposed. The foils were placed on a vacuum chuck having 0.008 inch thick shims at the edges. Two (2) mL of the reactant slurry was placed at one edge of the foil. Using a Sheen Auto-Draw Automatic Film Applicator 1137 (Sheen Instruments) the reactant slurry was coated onto the foils by drawing a #12 coating rod at an auto-draw coating speed of up to 50 mm/sec across the surface of the foils to deposit approximately an 0.006 inch thick layer of the Zr:$MoO_3$:LAPONITE® RDS reactant slurry. The coated foils were then placed in a 40° C. forced-air convection oven and dried for at least 2 hours. The masks were then removed from the foils to leave twelve rectangular coatings of solid fuel on each foil.

An initiator composition was prepared by adding 8.6 mL of a 4.25% VITON® A500/amyl acetate solution to a mixture of 0.680 g of Al (40-70 nm), 1.320 g of MoO$_3$ (nano), and 0.200 g of boron (nano) and mixing well. Two liL drops of the initiator composition were placed in a 0.06 inch diameter hole in the center of each of twelve 0.25 inch by 0.5 inch fiberglass mats (0.04 inch thickness, Directed Light). One drop of initiator composition was place in the hole from each side of fiberglass mat.

To assemble the heating unit, on the fuel coated foil (3 inch diameter) was placed four layers of double sided tape (3 inch diameter, Saint-Gobain Performance Plastics) with 12 rectangular holes (0.25 inch by 0.5 inch) cut into each tape such that the holes on the tape aligned with the fuel coatings on the foils. Into each hole in the tape layer was placed one fiberglass mat with the initiator. The tape was then covered with a 3 inch circular window made out of clear plastic (1/16 inch polycarbonate sheet, McMaster-Carr).

Each heating unit of the device was ignited is succession by pulsed flash light from a Xenon lamp powered by one AA battery through the polycarbonate window.

Although the invention has been described with respect to particular embodiments, it will be apparent to those skilled in the art that various changes and modifications can be made without departing from the invention.

What is claimed is:

1. A drug supply unit comprising:
a heating unit comprising:
an enclosure comprising a substrate having an exterior surface and an interior surface; and
a solid fuel comprising a metal, which metal is a reducing agent, and a metal-containing oxidizing agent, wherein the solid fuel is disposed on the interior surface of the substrate as a layer, wherein the thickness of the layer is in the range 0.001 inches to 0.030 inches and
a drug disposed on a portion of the exterior surface of the substrate;
wherein said drug comprises a film and the film has a thickness of less than 20 μm.

2. The drug supply unit of claim 1, wherein the drug supply unit comprises more than one heating unit.

3. A drug delivery device comprising:
a housing defining an airway;
a heating unit comprising:
an enclosure comprising a substrate having an exterior surface and an interior surface; and a solid fuel comprising a metal, which metal is a reducing agent, and a metal-containing oxidizing agent, wherein the solid fuel is disposed on the interior surface of the substrate as a layer, wherein the thickness of the layer is in the range 0.001 inches to 0.030 inches; and
a drug disposed on a portion of the exterior surface of the substrate, wherein the portion of the exterior surface comprising the drug is configured to be disposed within the airway; and
an igniter comprising an initiator composition configured to ignite the solid fuel;
wherein said igniter comprises a resistive heating element and an initiator composition disposed on the resistive heating element.

4. The drug delivery device of claim 3, wherein the initiator composition comprises at least one metal which is a reducing agent and at least one oxidizing agent.

5. The drug delivery device of claim 4, wherein the metal which is a reducing agent of the initiator composition is selected from at least one of: aluminum and zirconium.

6. The drug delivery device of claim 3, wherein the oxidizing agent of the initiator composition is selected from a chlorate of an alkali metal, a chlorate of an alkaline earth metal, a perchlorate of an alkali metal, and a perchlorate of an alkaline earth metal.

7. The drug delivery device of claim 6, wherein the oxidizing agent is selected from potassium chlorate and potassium perchlorate.

8. The drug delivery device of claim 3, wherein the initiator composition comprises an additive material.

9. The drug delivery device of claim 8 wherein the additive material is selected from diatomaceous earth, glass beads, and colloidal silica.

10. The drug delivery device of claim 3, further comprising a mechanism for producing an electric current to activate the igniter.

11. The drug delivery device of claim 3, further comprising a mechanism for producing electromagnetic radiation to activate the igniter.

12. The drug delivery device of claim 3, further comprising a mechanism for producing a percussive force to activate the igniter.

13. The drug delivery device of claim 3, wherein the drug delivery device comprises more than one heating unit.

* * * * *